(12) United States Patent
Varona et al.

(10) Patent No.: US 11,839,533 B2
(45) Date of Patent: Dec. 12, 2023

(54) DISPOSABLE ABSORBENT ARTICLE AND ABSORBENT CORE COMPOSITE OR CONSTRUCTION FOR INCORPORATION THEREWITH, COMPONENTS THEREFOR OR THEREOF, AND SYSTEMS, APPARATUS AND METHODS OF MAKING THE SAME

(71) Applicants: Eugenio Varona, Marietta, GA (US); Andrew Wright, Derbyshire (GB); Dennis Smid, Wolvega (NL)

(72) Inventors: Eugenio Varona, Marietta, GA (US); Andrew Wright, Derbyshire (GB); Dennis Smid, Wolvega (NL)

(73) Assignee: DSG Technology Holdings Ltd., Kwai Chung (HK)

( * ) Notice: Subject to any disclaimer, the term of this patent is extended or adjusted under 35 U.S.C. 154(b) by 1207 days.

(21) Appl. No.: 16/362,536

(22) Filed: Mar. 22, 2019

(65) Prior Publication Data

US 2019/0290505 A1    Sep. 26, 2019

Related U.S. Application Data

(60) Provisional application No. 62/646,880, filed on Mar. 22, 2018, provisional application No. 62/646,875, (Continued)

(51) Int. Cl.
*A61F 13/53* (2006.01)
*B32B 38/00* (2006.01)
(Continued)

(52) U.S. Cl.
CPC ........ *A61F 13/53* (2013.01); *A61F 13/15617* (2013.01); *A61F 13/15707* (2013.01);
(Continued)

(58) Field of Classification Search
CPC .......... A61F 13/15617; A61F 13/15658; A61F 13/15699; A61F 13/15707;
(Continued)

(56) References Cited

U.S. PATENT DOCUMENTS 3,246,378 A * 4/1966 Beckers ................ D06C 11/00
                                                      26/30
4,338,371 A    7/1982 Dawn et al.
(Continued)

FOREIGN PATENT DOCUMENTS

CN        105263455 A      1/2016
CN        105530900 A      4/2016
(Continued)

OTHER PUBLICATIONS

International Search Report and Written Opinion dated Sep. 26, 2019 (issued in PCT Application No. PCT/US2019/023743) [17 pages].

(Continued)

*Primary Examiner* — Michael A Tolin
(74) *Attorney, Agent, or Firm* — Alberto Q Amatong, Jr.; Amatong McCoy LLC

(57) ABSTRACT

Improved absorbent core components including multiple layers configured to enhance fluid handling properties. The layers include absorbent material layers, with or without absorbent material-free lanes. The layers also include nonwoven layers, including air-through nonwovens, bulkified nonwovens, slitted nonwovens, and bulky nonwovens.

33 Claims, 47 Drawing Sheets

Related U.S. Application Data filed on Mar. 22, 2018, provisional application No. 62/646,870, filed on Mar. 22, 2018.

(51) Int. Cl.
  *B32B 5/26* (2006.01)
  *A61F 13/49* (2006.01)
  *A61F 13/15* (2006.01)

(52) U.S. Cl.
  CPC ........ *A61F 13/49058* (2013.01); *B32B 5/266* (2021.05); *B32B 38/0012* (2013.01); *A61F 2013/15934* (2013.01); *A61F 2013/49074* (2013.01)

(58) Field of Classification Search
  CPC .......... A61F 13/15731; A61F 13/49007; A61F 13/49058; A61F 13/53; A61F 13/532; A61F 13/5323; A61F 13/533; A61F 13/534; A61F 13/535; A61F 13/536; A61F 13/537; A61F 13/53708; A61F 13/5376; A61F 2013/15422; A61F 2013/15487; A61F 2013/15495; A61F 2013/1591; A61F 2013/15934; A61F 2013/49074; A61F 2013/530481; A61F 2013/530489; A61F 2013/530562; A61F 2013/530591; A61F 2013/530868; A61F 2013/530897; A61F 2013/53721; A61F 2013/53734; B32B 5/022; B32B 5/14; B32B 5/142; B32B 5/145; B32B 5/147; B32B 5/26; B32B 5/265; B32B 5/266; B32B 38/0012; B32B 38/06; D06C 11/00
  See application file for complete search history.

(56) References Cited

U.S. PATENT DOCUMENTS

| | | | |
|---|---|---|---|
| 5,171,302 A | 12/1992 | Buell | |
| 5,197,959 A | 3/1993 | Buell | |
| 5,350,370 A | 9/1994 | Jackson et al. | |
| 5,458,592 A | 10/1995 | Abuto et al. | |
| 5,466,513 A | 11/1995 | Wanek et al. | |
| 5,486,167 A | 1/1996 | Dragoo et al. | |
| 5,591,150 A | 1/1997 | Olsen et al. | |
| 5,846,230 A | 12/1998 | Osborn et al. | |
| 6,071,549 A | 6/2000 | Hansen | |
| 6,160,197 A | 12/2000 | Lassen et al. | |
| 6,278,037 B1 | 8/2001 | Schmidt et al. | |
| 6,432,094 B1 | 8/2002 | Fujioka et al. | |
| 6,540,853 B1 | 4/2003 | Suzuki et al. | |
| 6,632,209 B1 | 10/2003 | Chmielewski | |
| 6,729,807 B1 | 5/2004 | Spittle | |
| 7,194,789 B2* | 3/2007 | Thomaschefsky | D04H 1/492 28/104 |
| 7,722,590 B2 | 5/2010 | Tsuji et al. | |
| 7,744,576 B2 | 6/2010 | Busam et al. | |
| 7,750,203 B2 | 7/2010 | Becker et al. | |
| 8,148,598 B2 | 4/2012 | Tsang et al. | |
| 8,187,240 B2 | 5/2012 | Busam et al. | |
| 8,268,424 B1 | 9/2012 | Suzuki et al. | |
| 8,361,047 B2 | 1/2013 | Mukai et al. | |
| 8,568,566 B2 | 10/2013 | Jackels et al. | |
| 8,702,671 B2 | 4/2014 | Tsang et al. | |
| 8,979,815 B2 | 3/2015 | Roe et al. | |
| 9,072,634 B2 | 7/2015 | Hundorf et al. | |
| 9,216,116 B2 | 12/2015 | Roe et al. | |
| 9,216,118 B2 | 12/2015 | Roe et al. | |
| 9,295,593 B2 | 3/2016 | Malderen | |
| 9,468,566 B2 | 10/2016 | Rosati et al. | |
| 9,492,328 B2 | 11/2016 | Jackels et al. | |
| 9,532,910 B2 | 1/2017 | Rosati et al. | |
| 9,549,858 B2 | 1/2017 | Yang | |
| 9,566,198 B2* | 2/2017 | Wright | A61F 13/539 |
| 9,603,750 B2 | 3/2017 | Maele | |
| 9,707,135 B2 | 7/2017 | Sheldon et al. | |
| 9,713,556 B2 | 7/2017 | Arizti et al. | |
| 9,713,557 B2 | 7/2017 | Arizti et al. | |
| 9,757,284 B2 | 9/2017 | Tsang et al. | |
| 9,789,009 B2 | 10/2017 | Joseph | |
| 9,789,011 B2 | 10/2017 | Roe et al. | |
| 9,789,014 B2 | 10/2017 | Wright et al. | |
| 9,974,699 B2 | 5/2018 | Kreuzer et al. | |
| 9,987,176 B2 | 6/2018 | Roe et al. | |
| 10,071,002 B2 | 9/2018 | Bianchi et al. | |
| 10,201,462 B2 | 2/2019 | Wright et al. | |
| 10,912,681 B2* | 2/2021 | Nakamura | B32B 29/02 |
| 2003/0129915 A1 | 7/2003 | Harriz | |
| 2004/0054342 A1 | 3/2004 | Newbill et al. | |
| 2004/0204697 A1 | 10/2004 | Litvay | |
| 2009/0112175 A1 | 4/2009 | Bissah et al. | |
| 2011/0111199 A1 | 5/2011 | Takatori et al. | |
| 2011/0276019 A1 | 11/2011 | Kakimoto et al. | |
| 2011/0313384 A1 | 12/2011 | Akiyama | |
| 2012/0029456 A1 | 2/2012 | Takatori et al. | |
| 2012/0089108 A1 | 4/2012 | Ueda et al. | |
| 2012/0095380 A1 | 4/2012 | Gergely et al. | |
| 2012/0203191 A1 | 8/2012 | Maruo et al. | |
| 2012/0308799 A1 | 12/2012 | Yamaguchi et al. | |
| 2012/0328862 A1 | 12/2012 | Fukudome et al. | |
| 2013/0072890 A1 | 3/2013 | Yang | |
| 2014/0276503 A1 | 9/2014 | Sheldon et al. | |
| 2015/0045756 A1 | 2/2015 | Wright et al. | |
| 2015/0080821 A1 | 3/2015 | Peri et al. | |
| 2017/0095379 A1* | 4/2017 | Cipriani | D04H 1/60 |
| 2017/0224548 A1 | 8/2017 | Tsang et al. | |
| 2018/0064583 A1 | 3/2018 | Maele | |

FOREIGN PATENT DOCUMENTS

| | | | |
|---|---|---|---|
| CN | 205515230 U | 8/2016 | |
| CN | 107080620 A | 8/2017 | |
| CN | 107106347 A | 8/2017 | |
| EP | 1800638 A1 | 6/2007 | |
| EP | 2550946 A1 | 1/2013 | |
| EP | 2901992 A1 | 8/2015 | |
| EP | 3037079 A1 | 6/2016 | |
| JP | 2007144101 A | 6/2007 | |
| JP | 2008138340 A | 6/2008 | |
| JP | 2014068813 A | 4/2014 | |
| WO | 1999001095 A1 | 1/1999 | |
| WO | 2011070728 A1 | 6/2011 | |
| WO | 2013099634 A1 | 7/2013 | |
| WO | 2014200794 A1 | 12/2014 | |
| WO | 2014145312 A3 | 1/2015 | |
| WO | 2016106021 A1 | 6/2016 | |
| WO | 2016108039 A1 | 7/2016 | |
| WO | 2016114209 A1 | 7/2016 | |
| WO | WO-2017131014 A1 * | 8/2017 | ....... A61F 13/15585 |
| WO | 2020131961 A1 | 6/2020 | |

OTHER PUBLICATIONS

Supplementary EP Search Report issued in EP Application No. 19771422.3 dated Nov. 29, 2021 [10 pages].

International Preliminary Report on Patentability issued in PCT Application No. PCT/US2019/023743, dated Oct. 1, 2020; 12 pages.

* cited by examiner

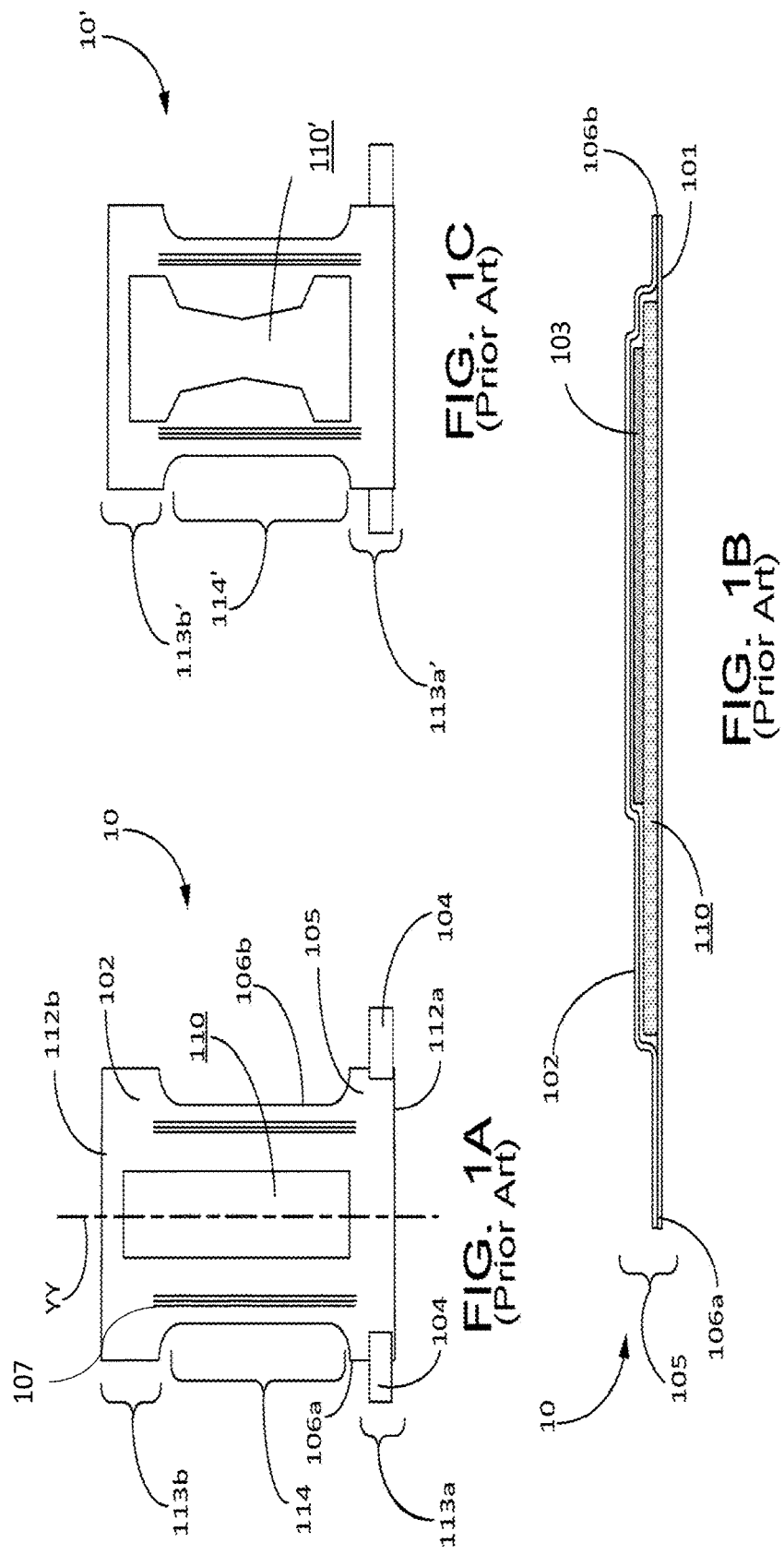

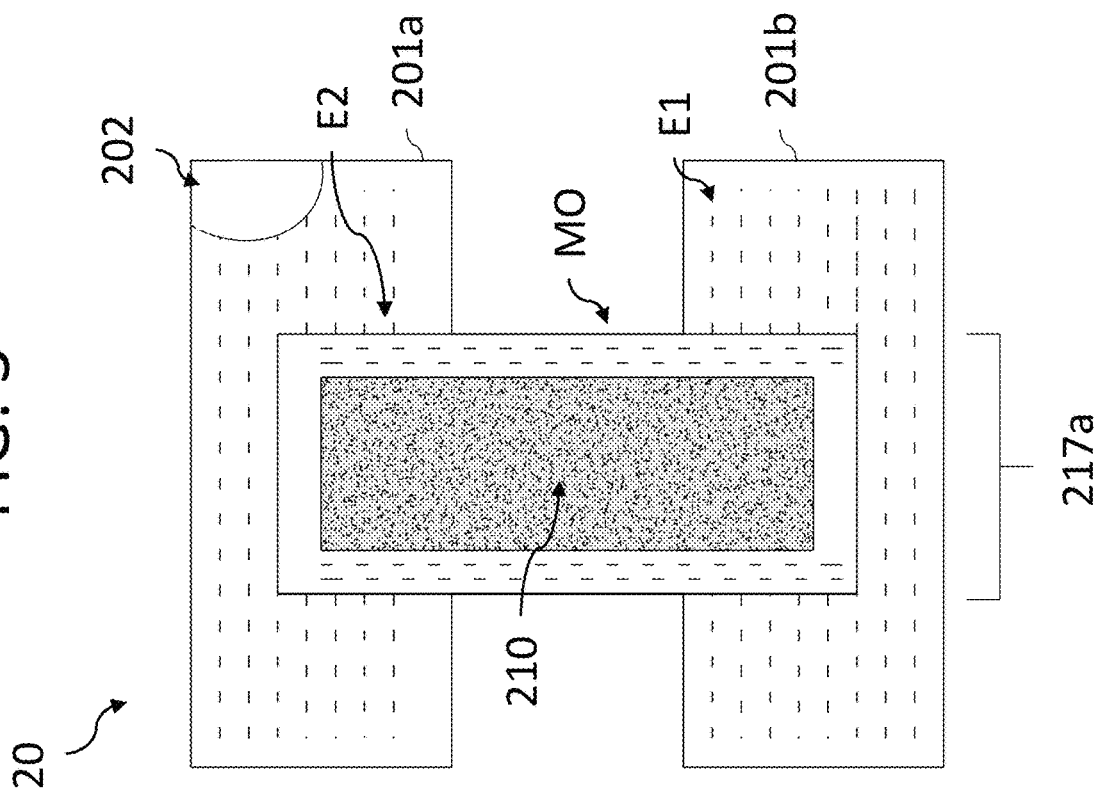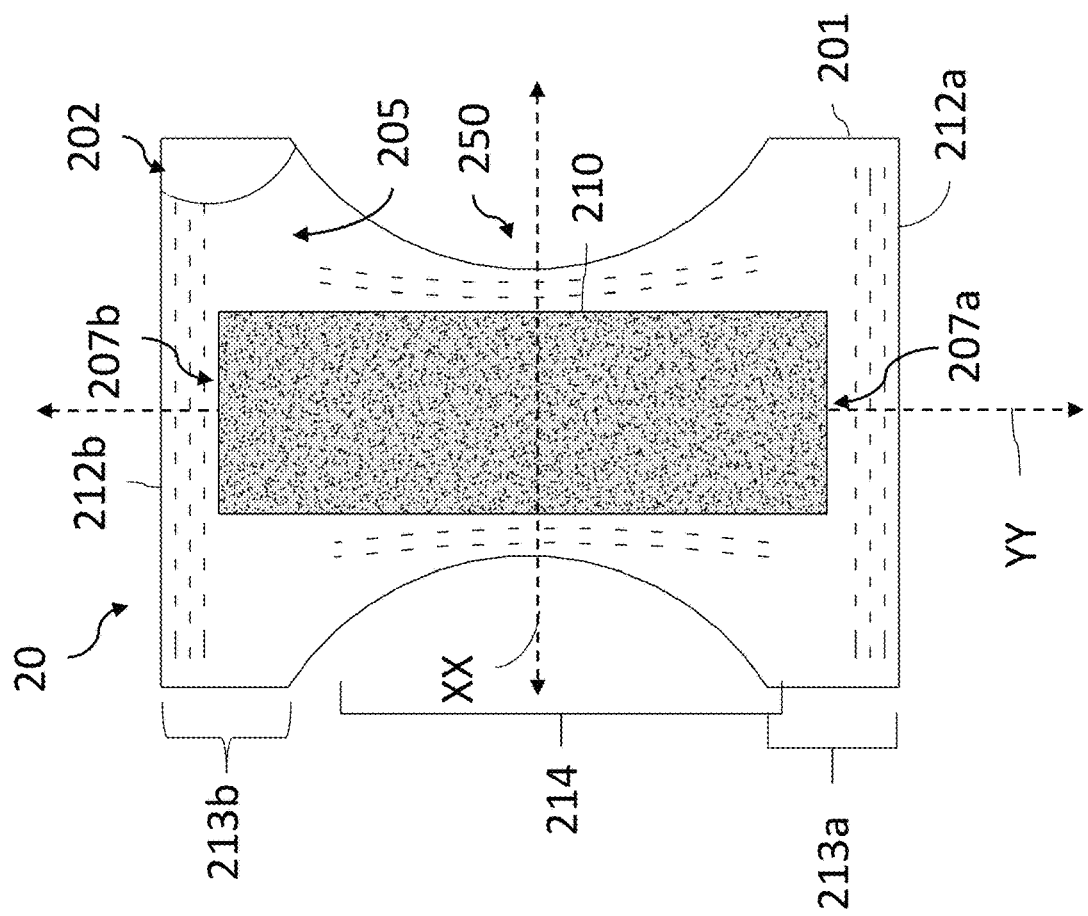

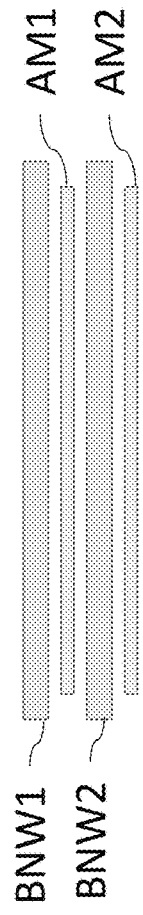
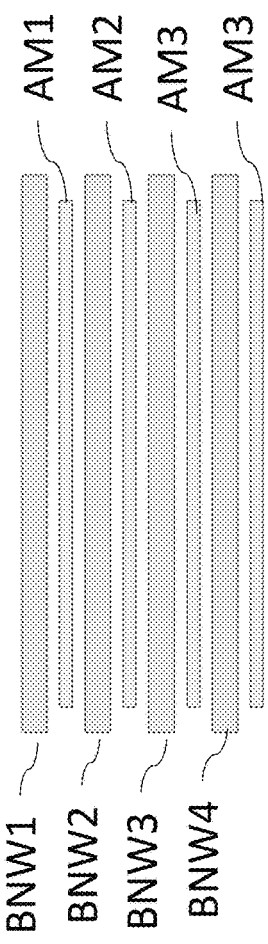
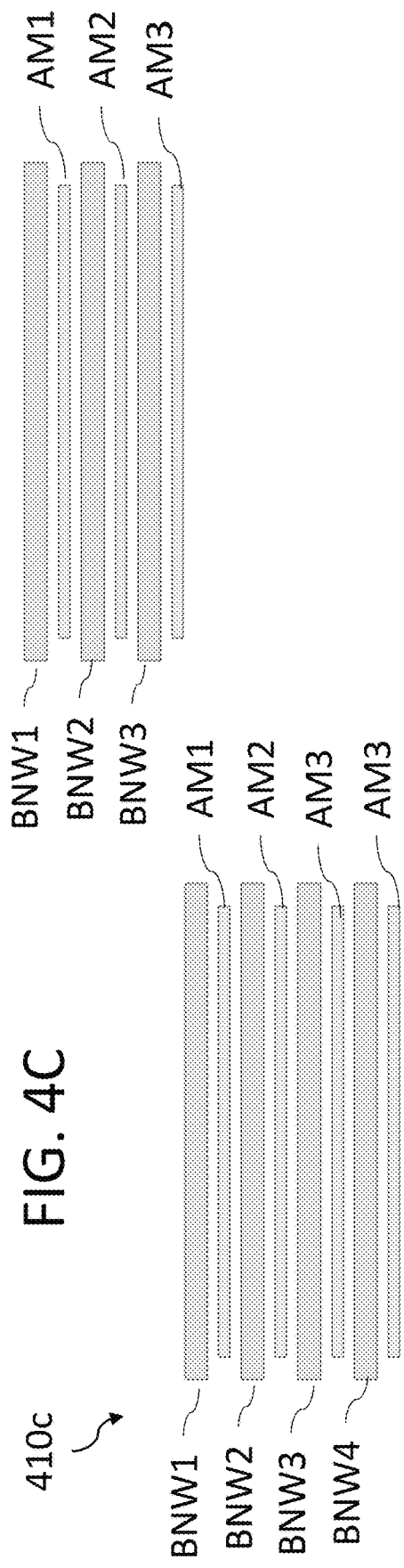
FIG. 4A
FIG. 4B
FIG. 4C

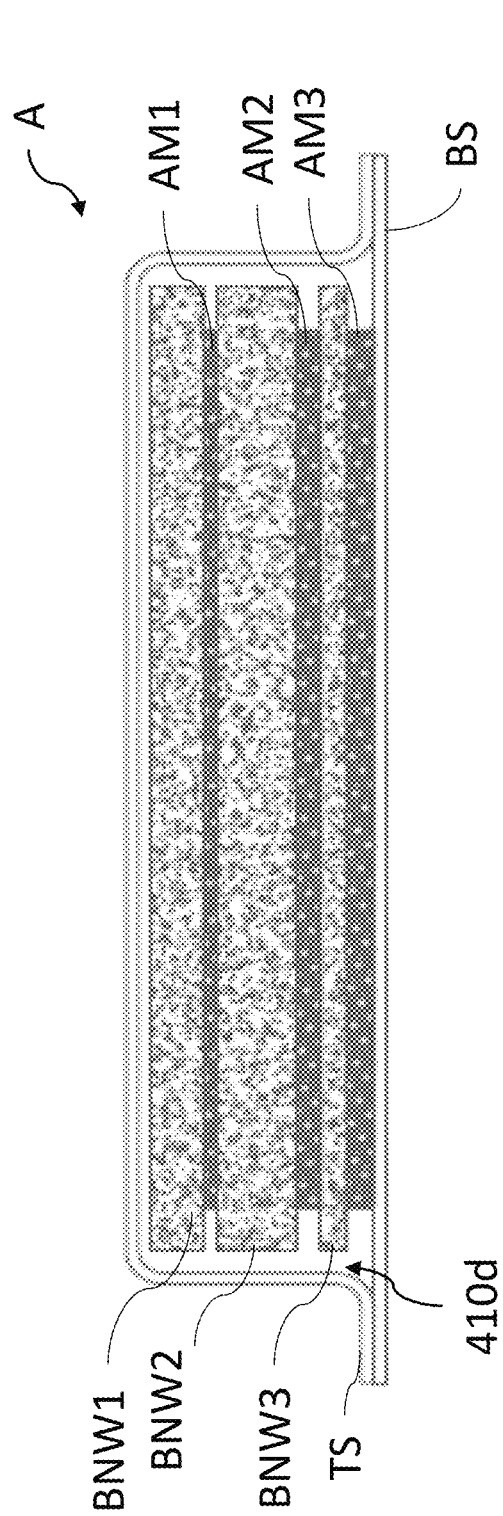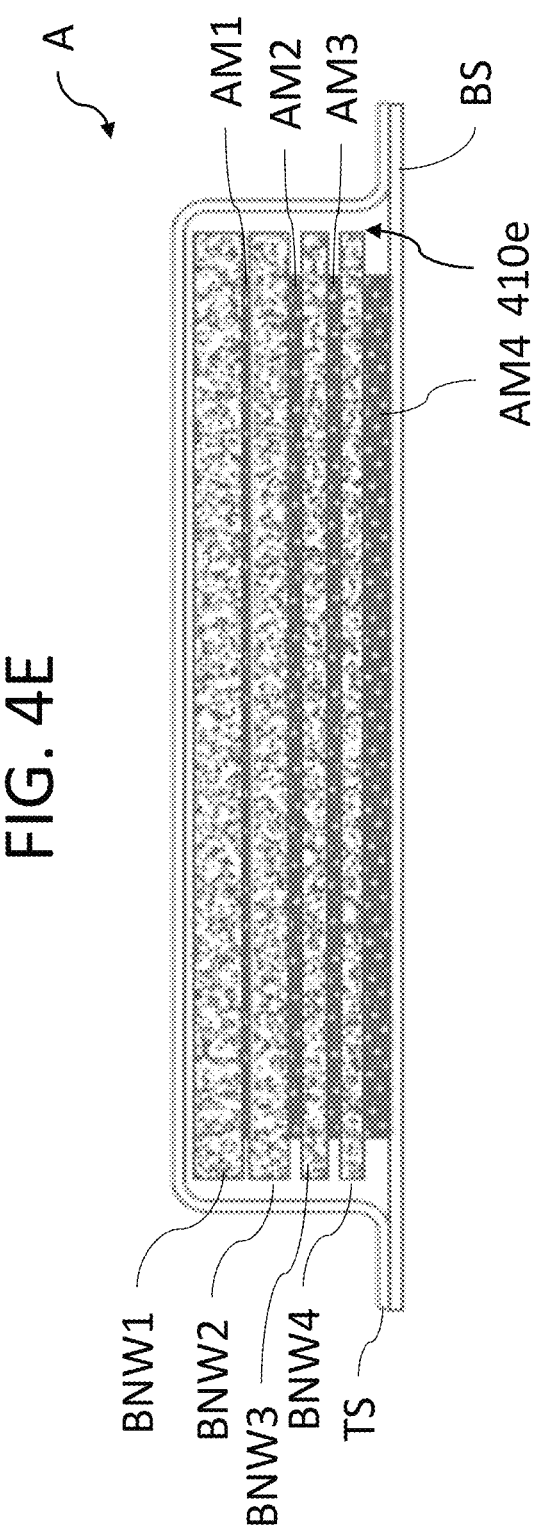

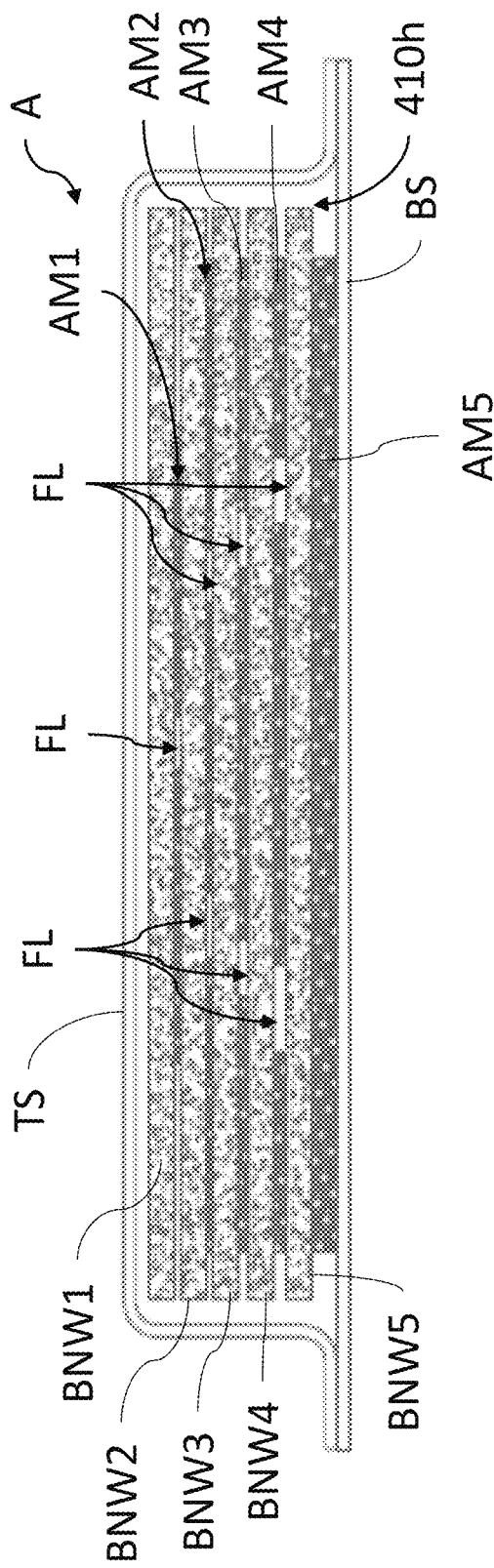
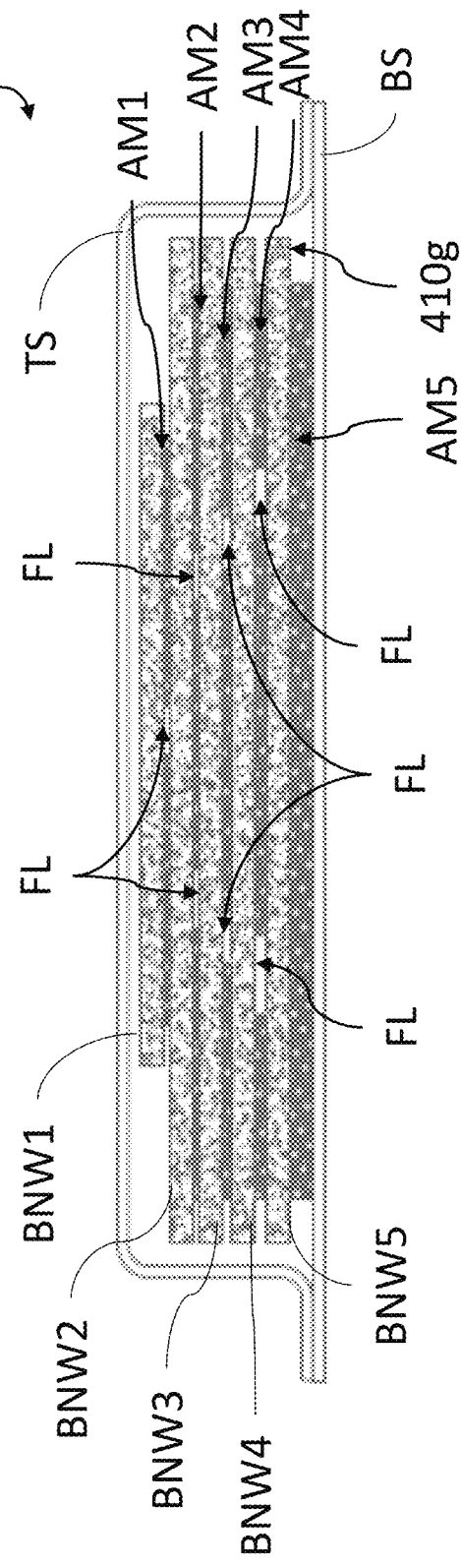
FIG. 4H
FIG. 4I

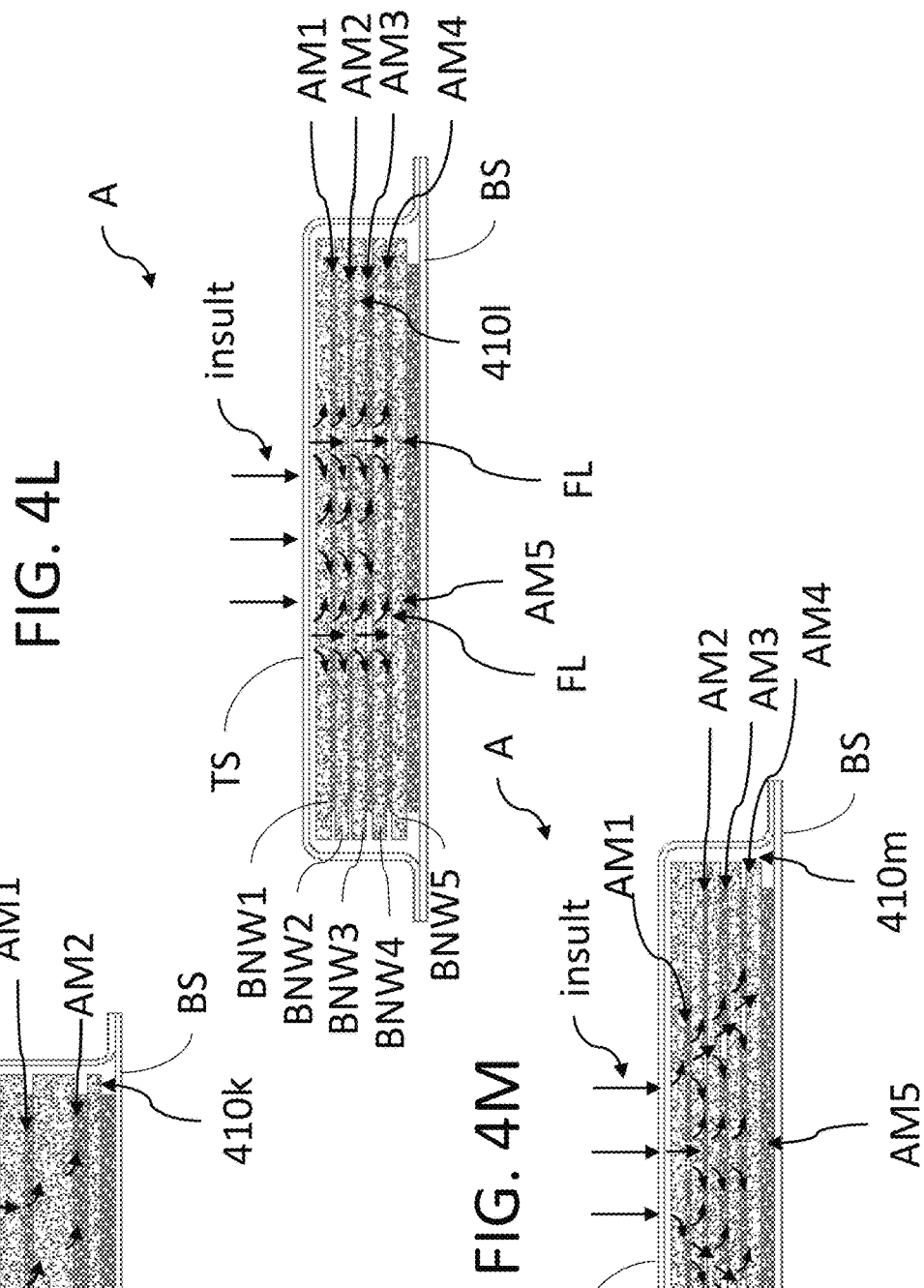

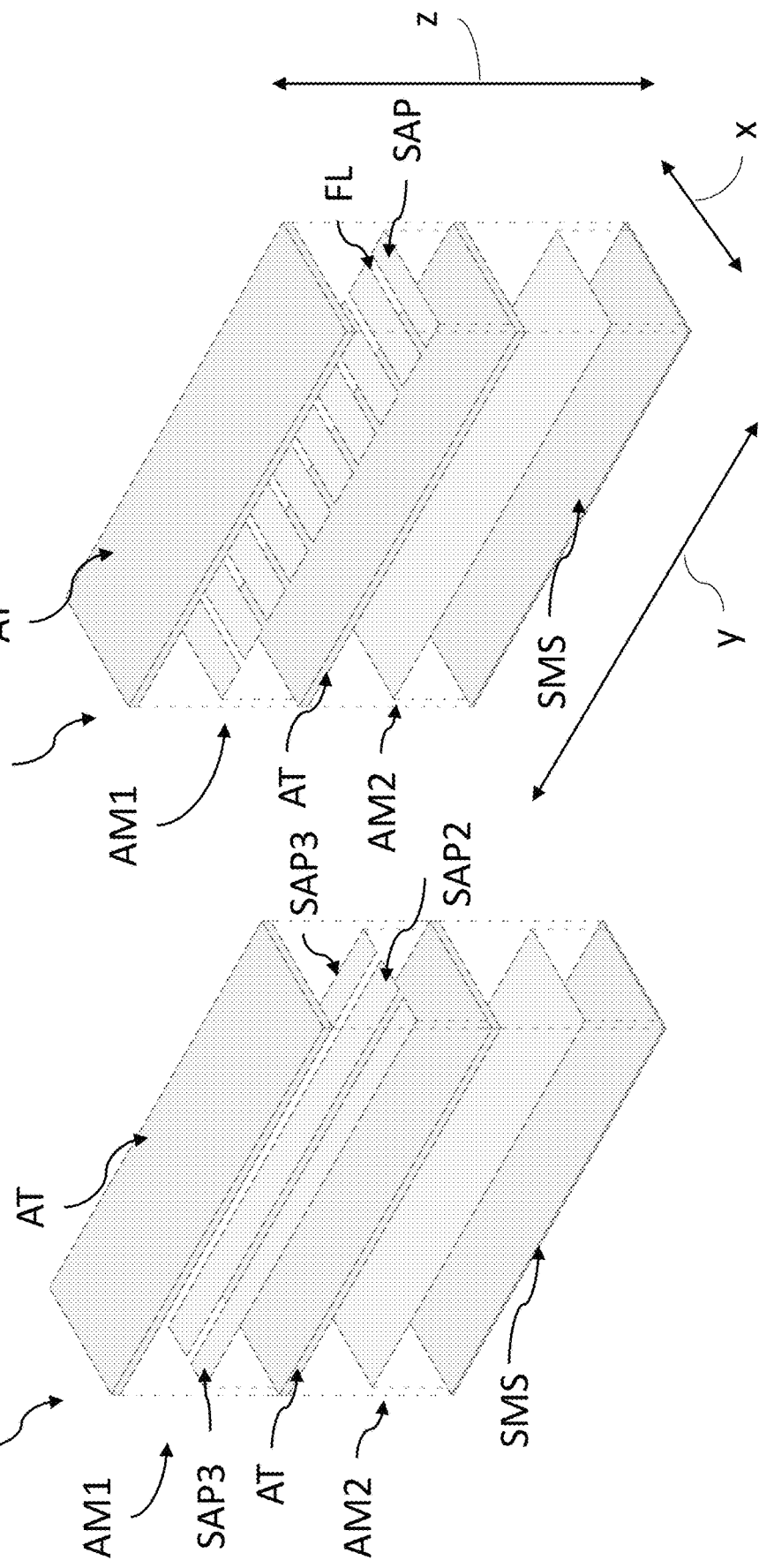

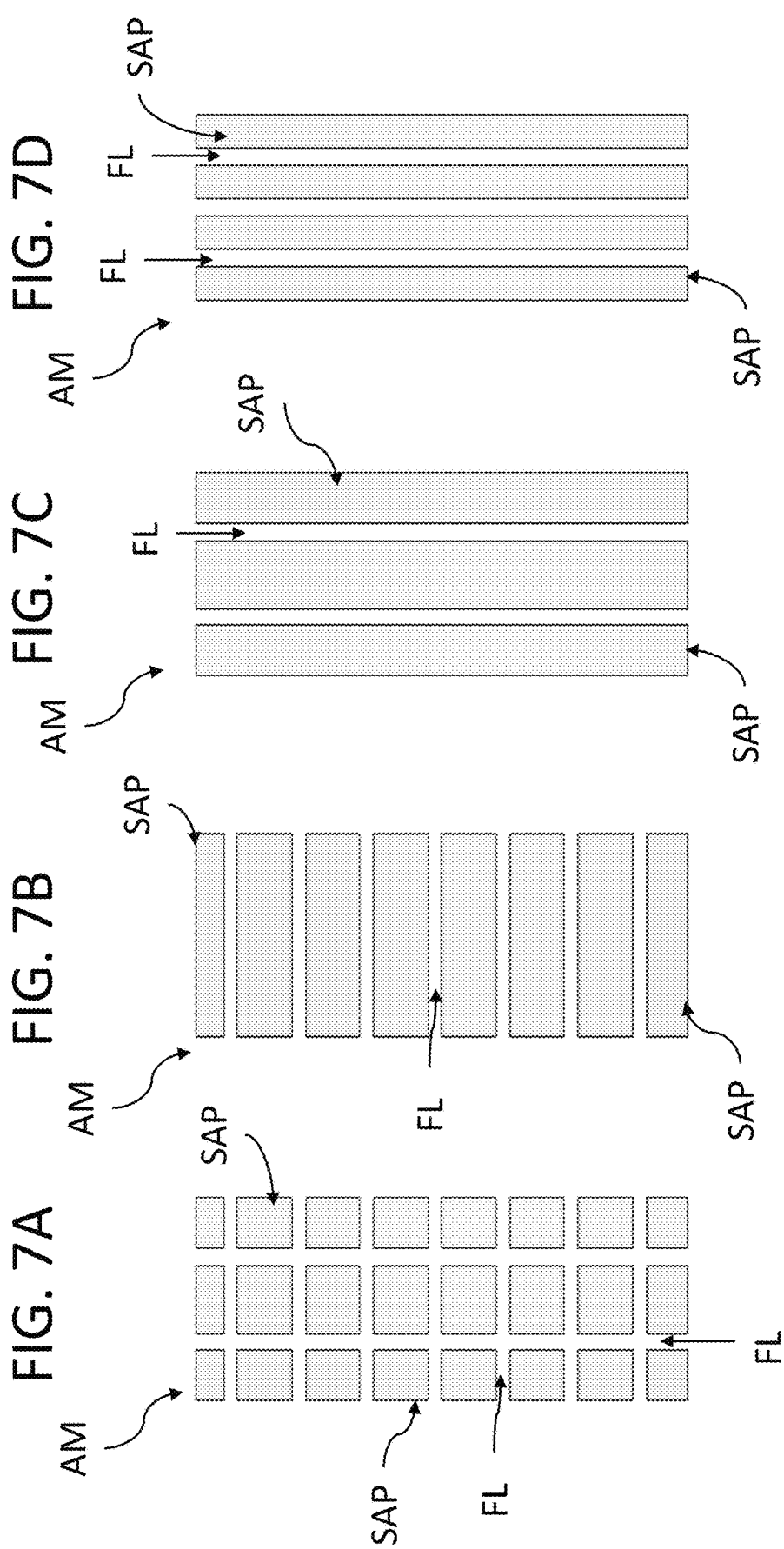

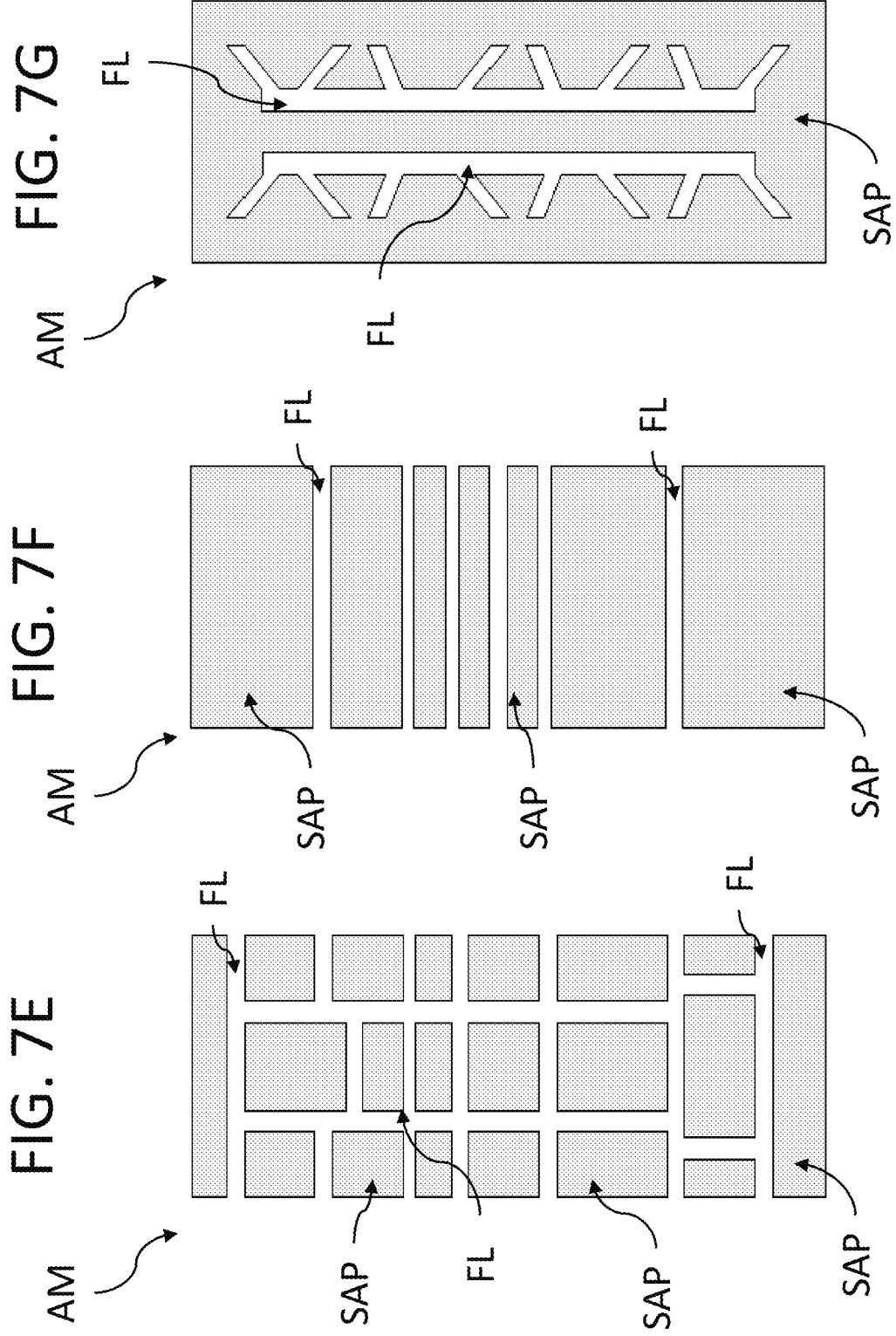

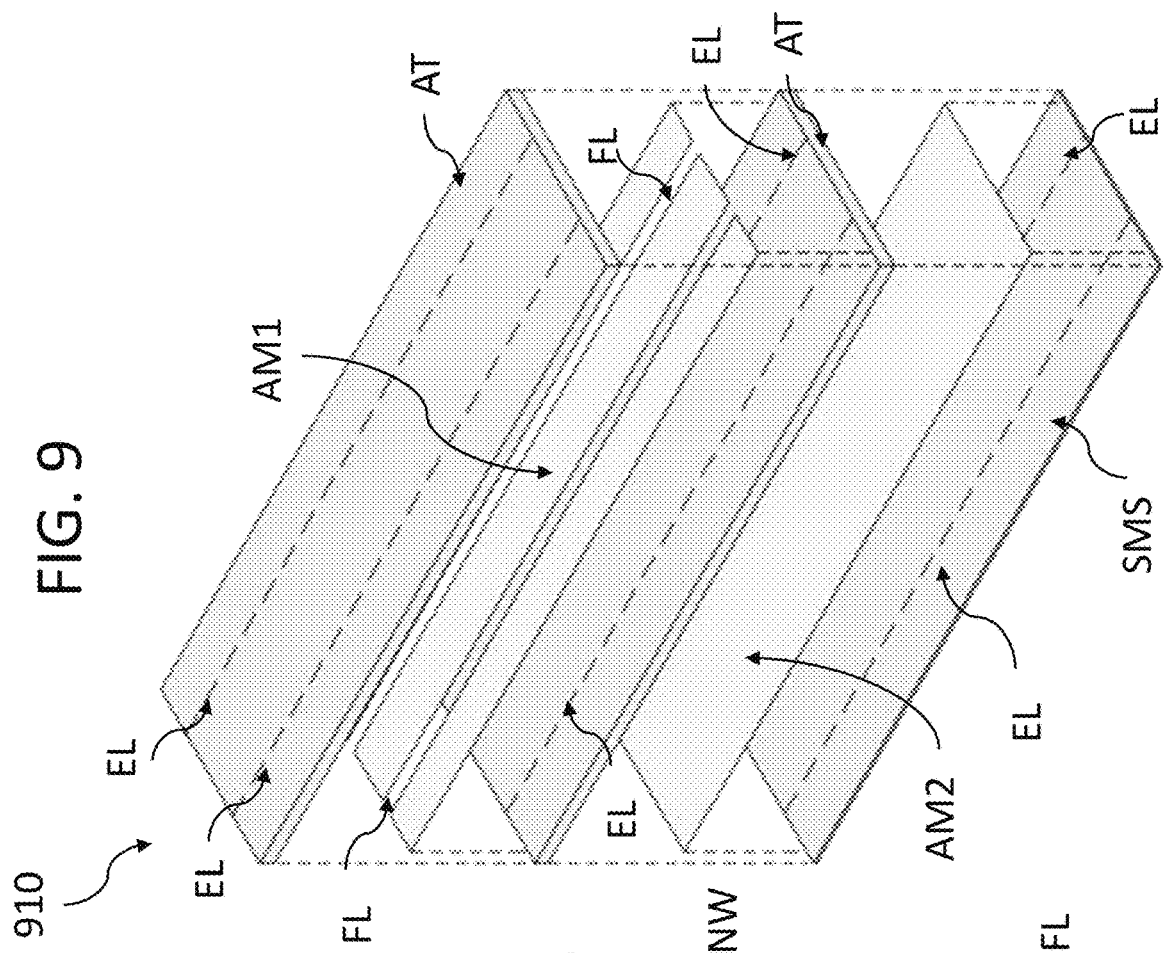
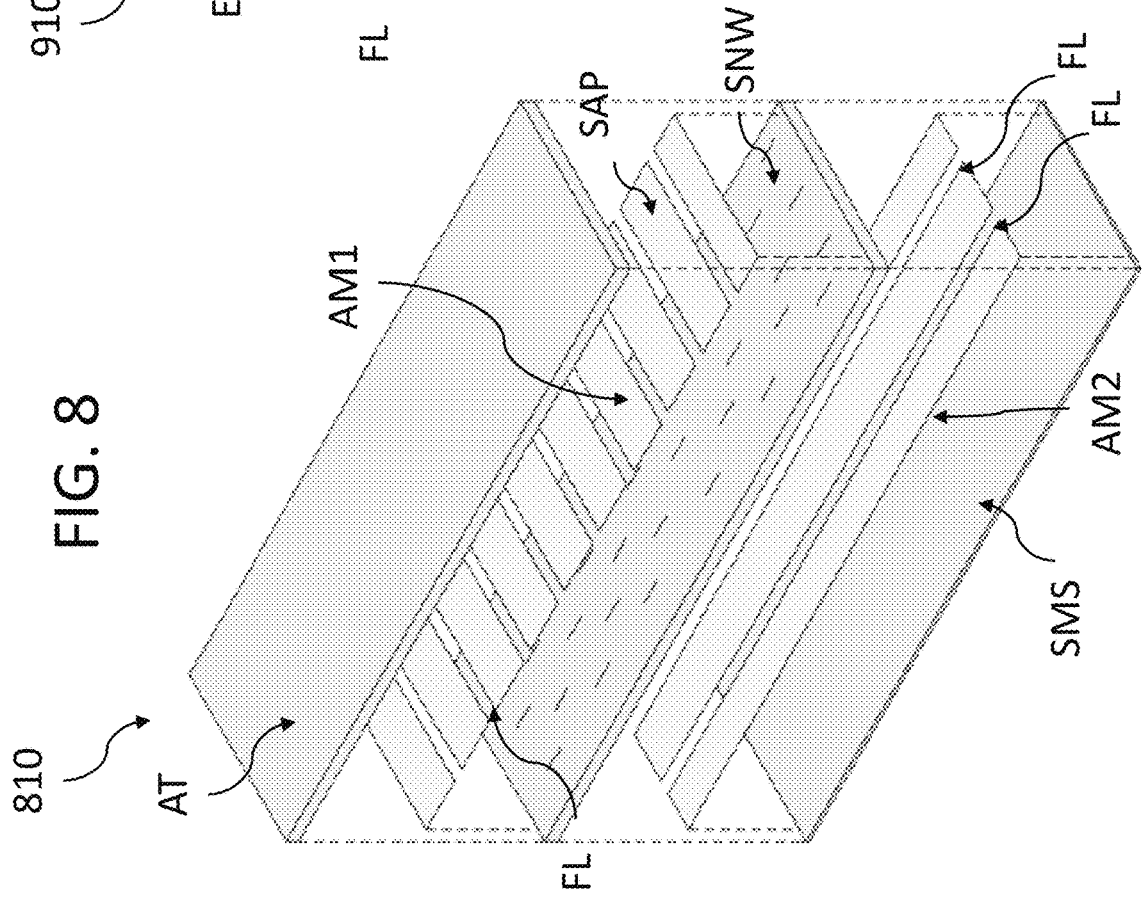

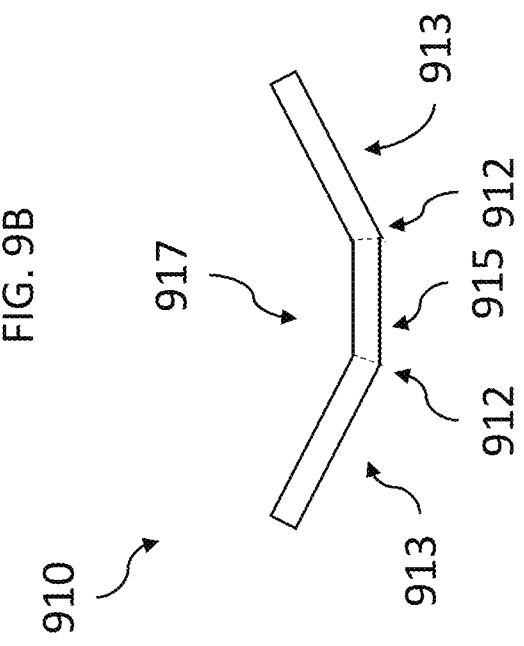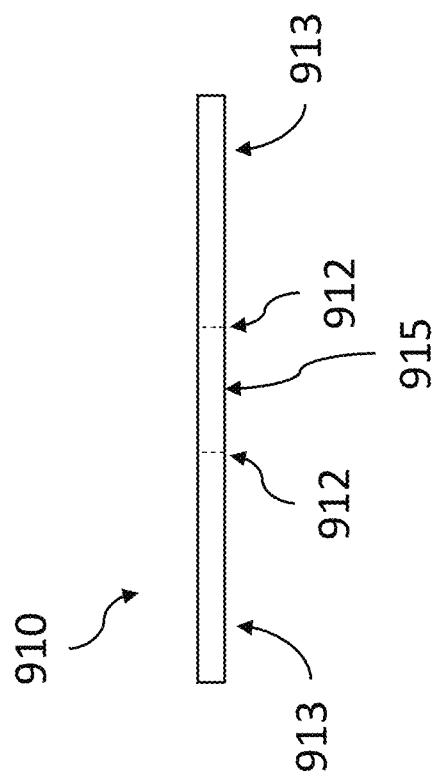

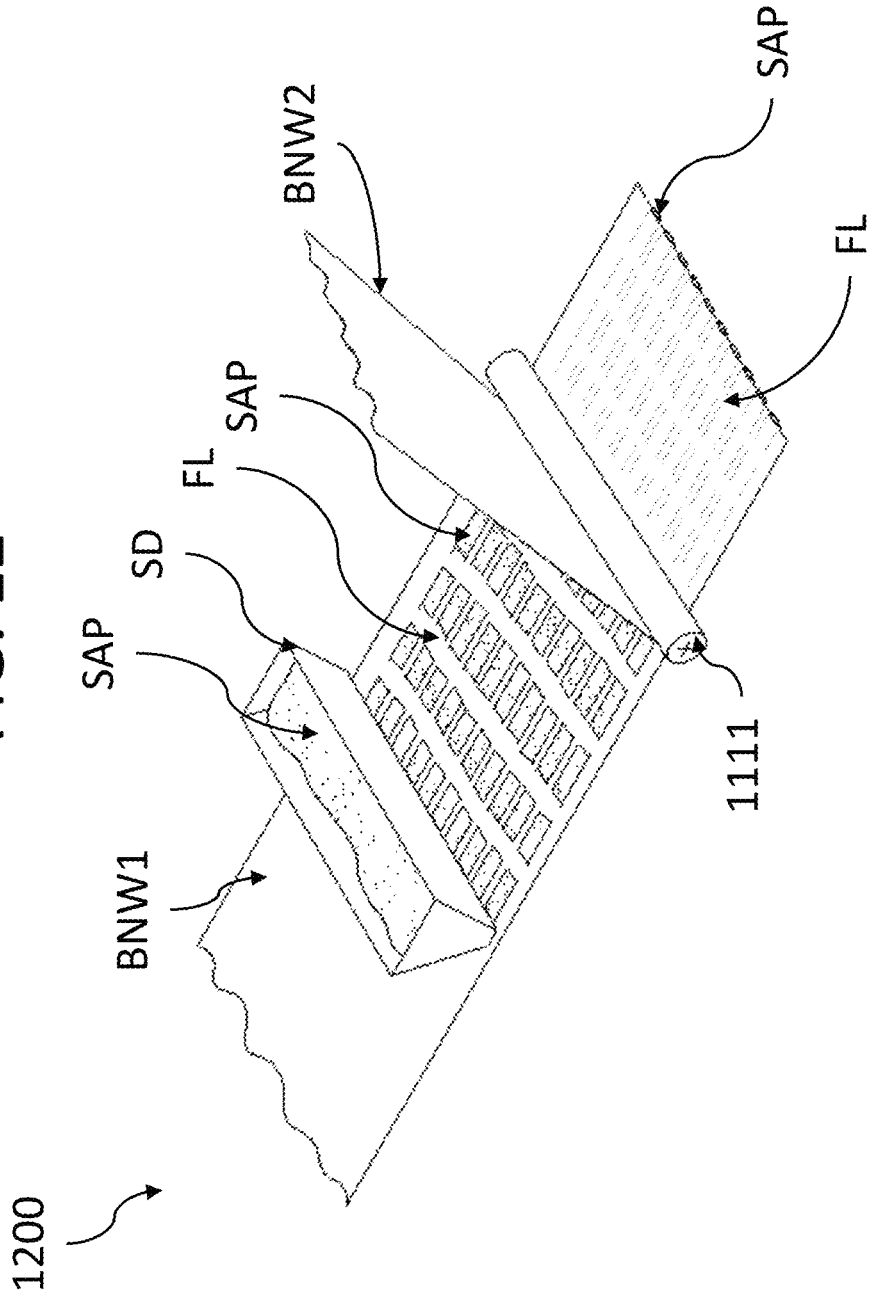

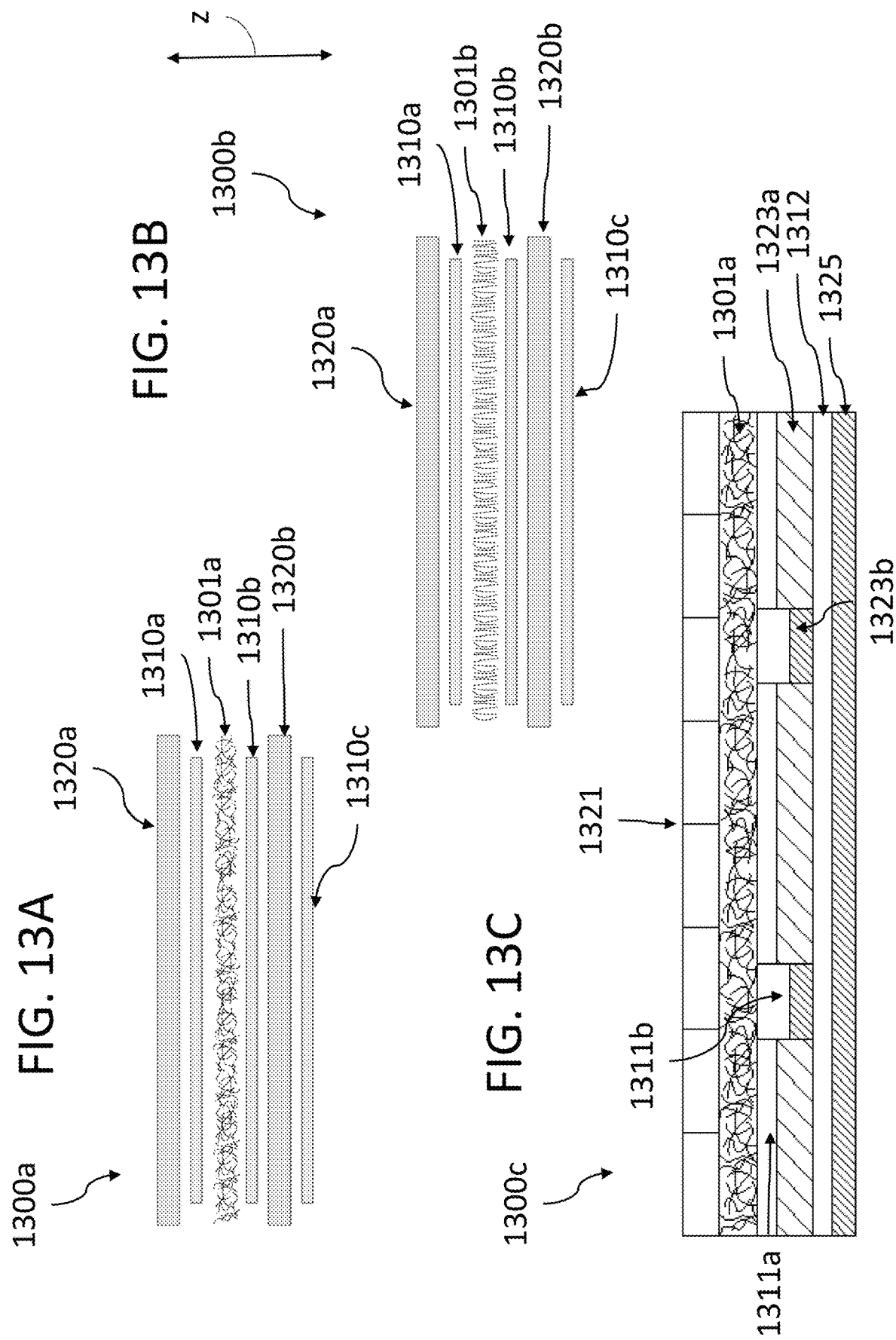

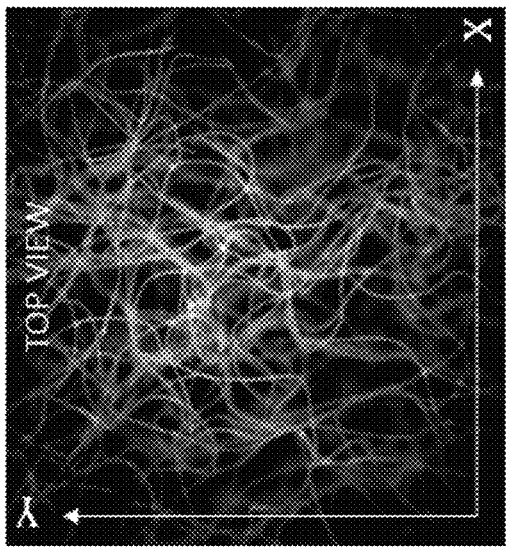
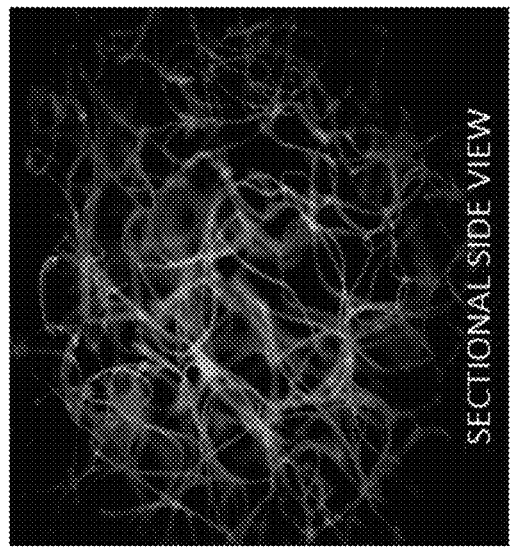
FIG. 15A
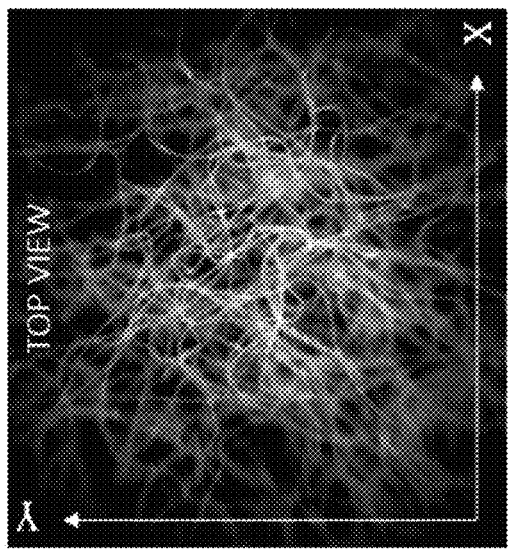
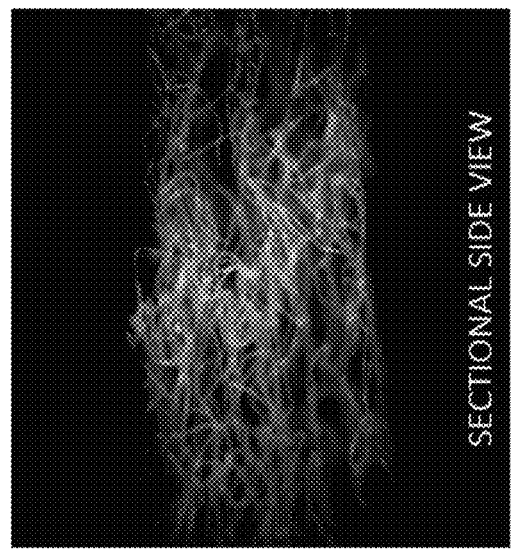
FIG. 15B

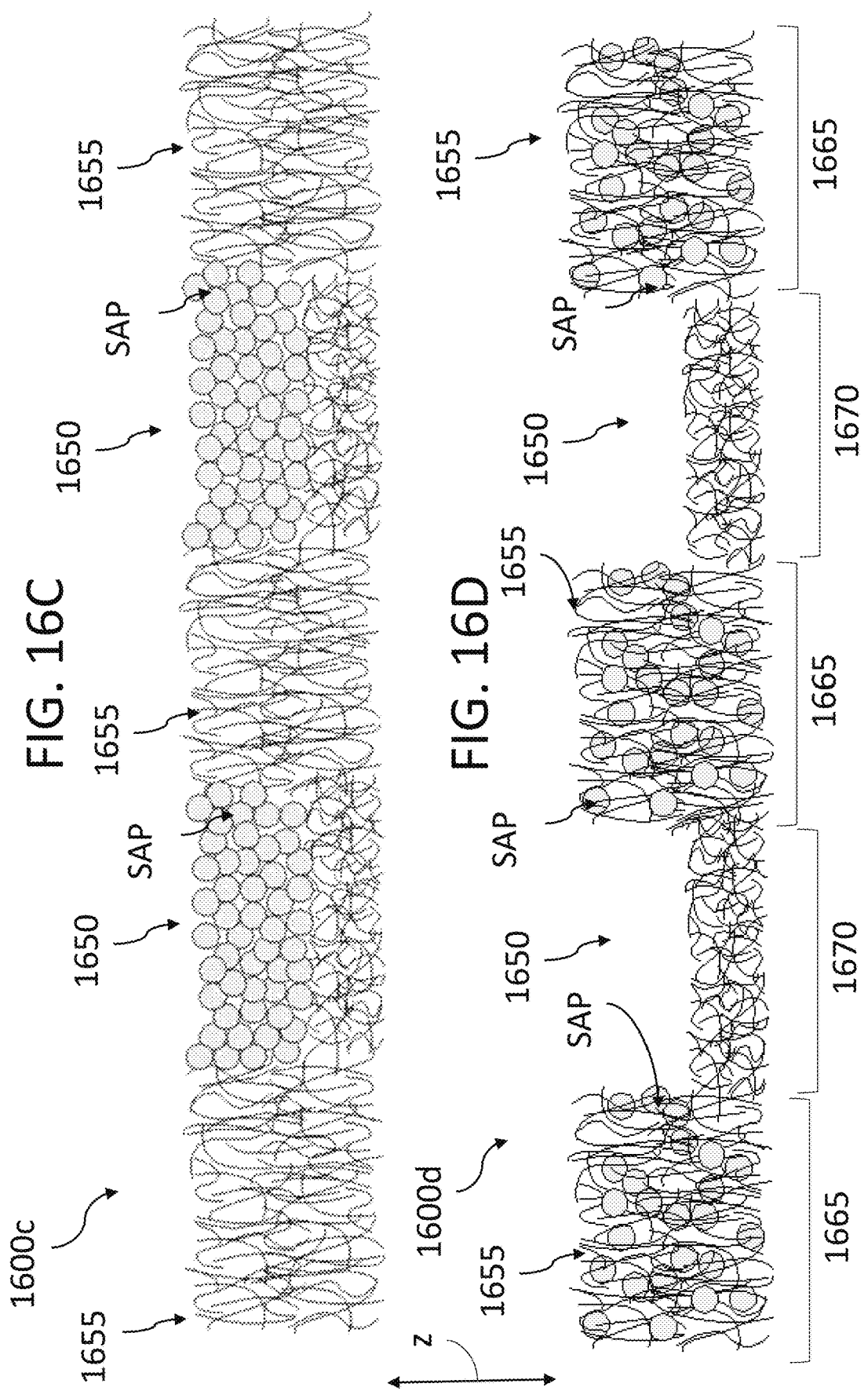

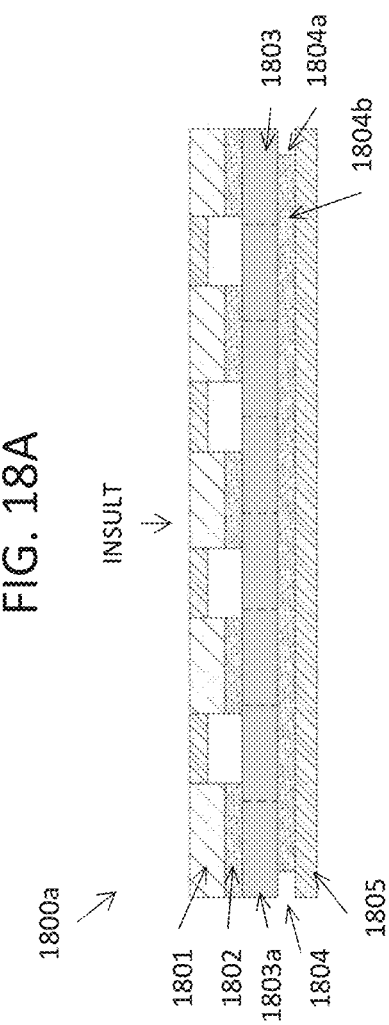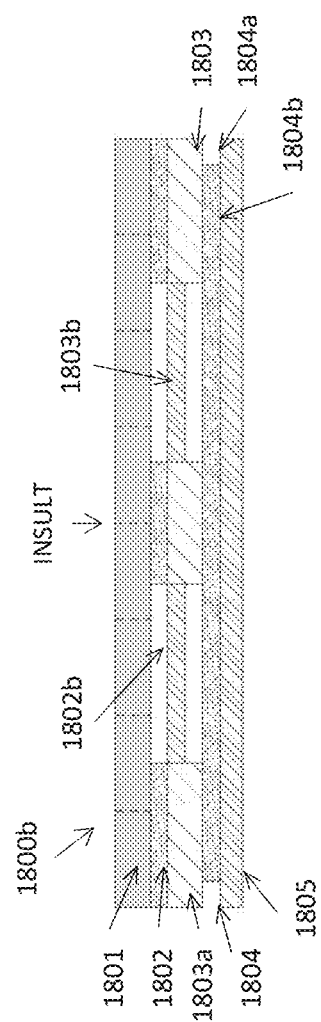

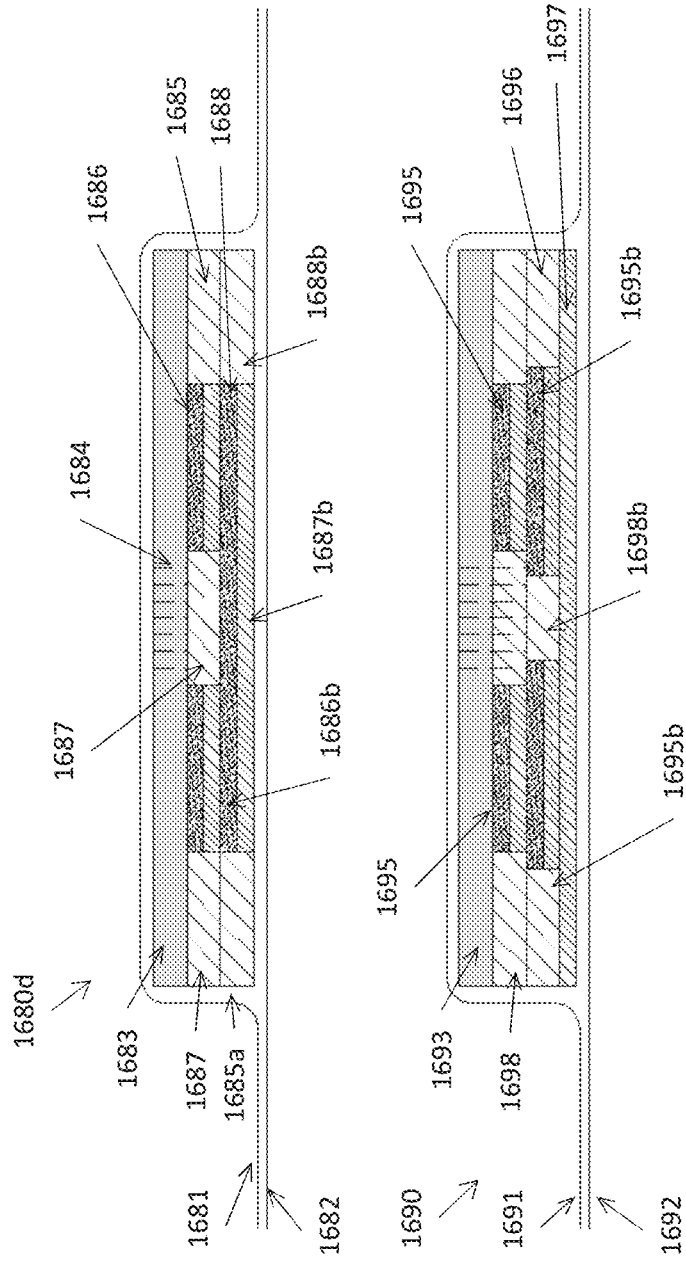

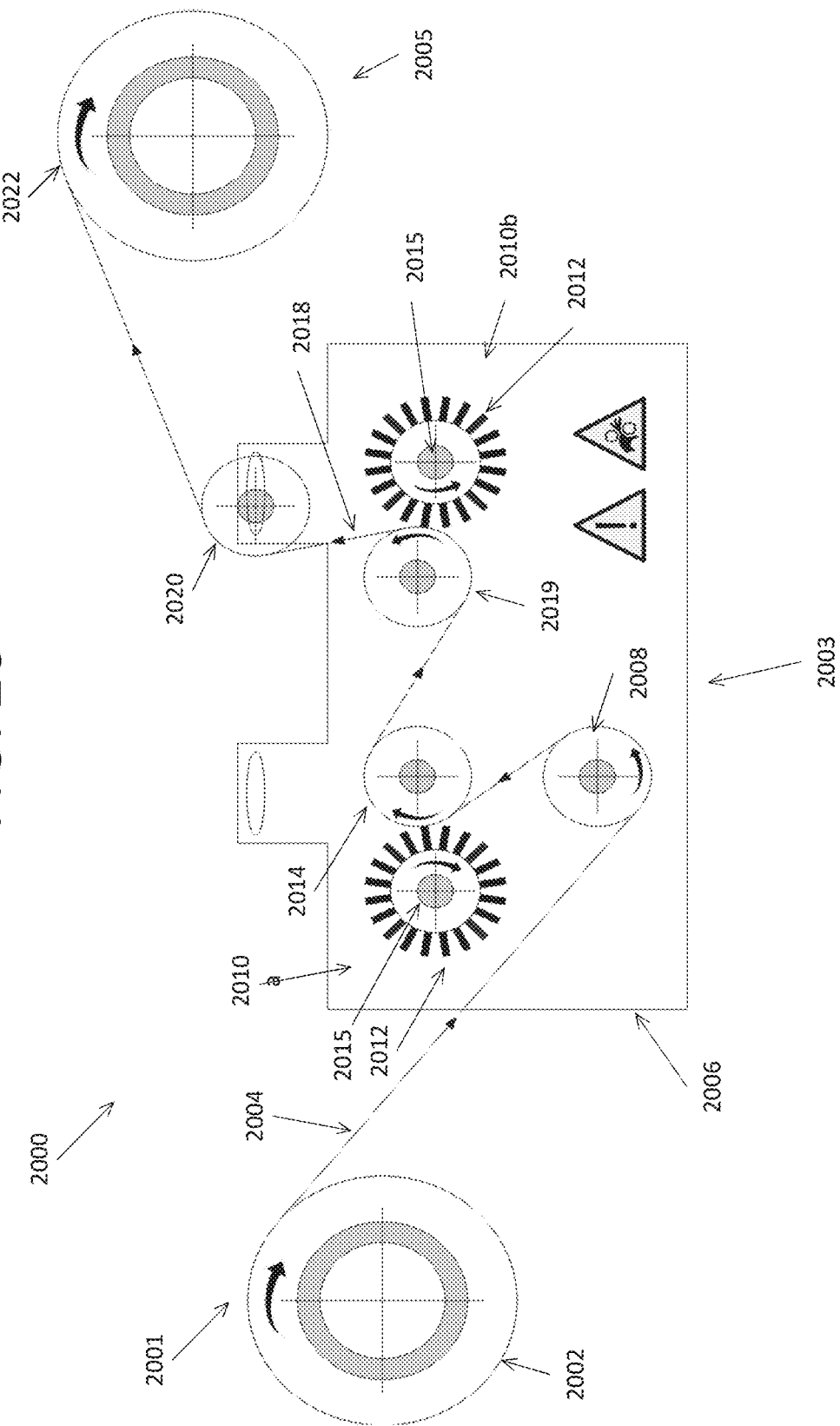

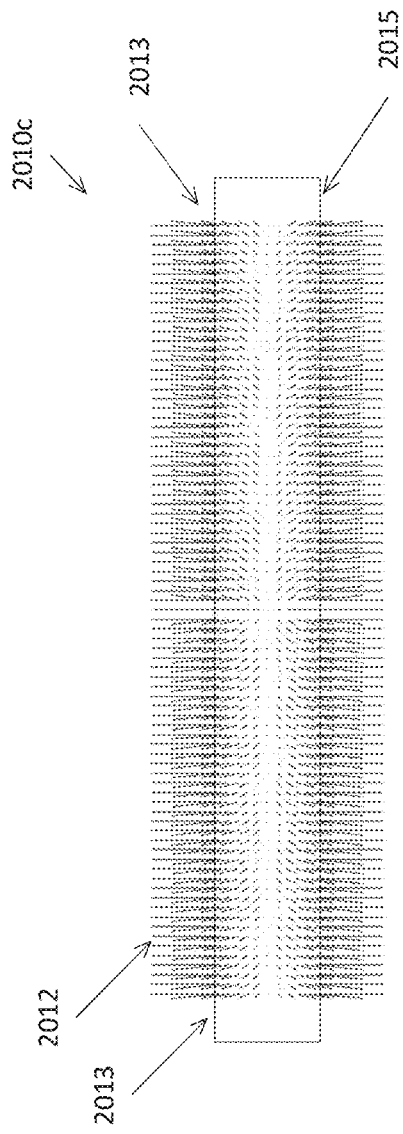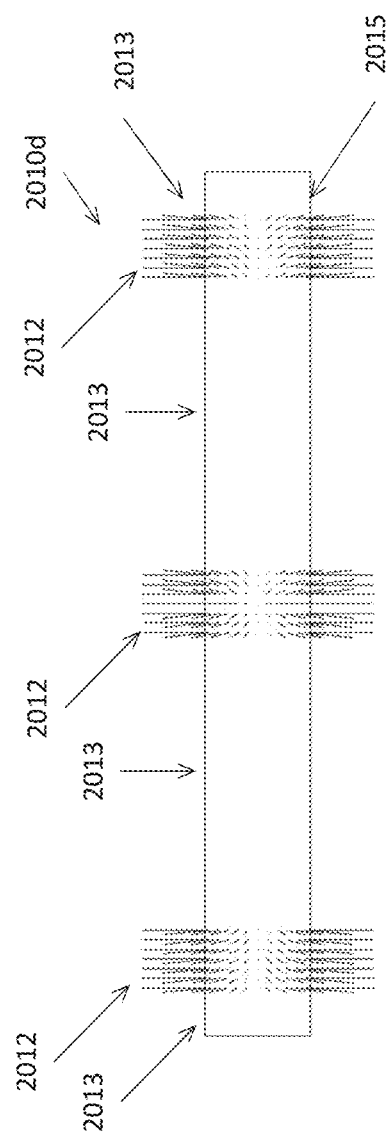
FIG. 20A
FIG. 20B

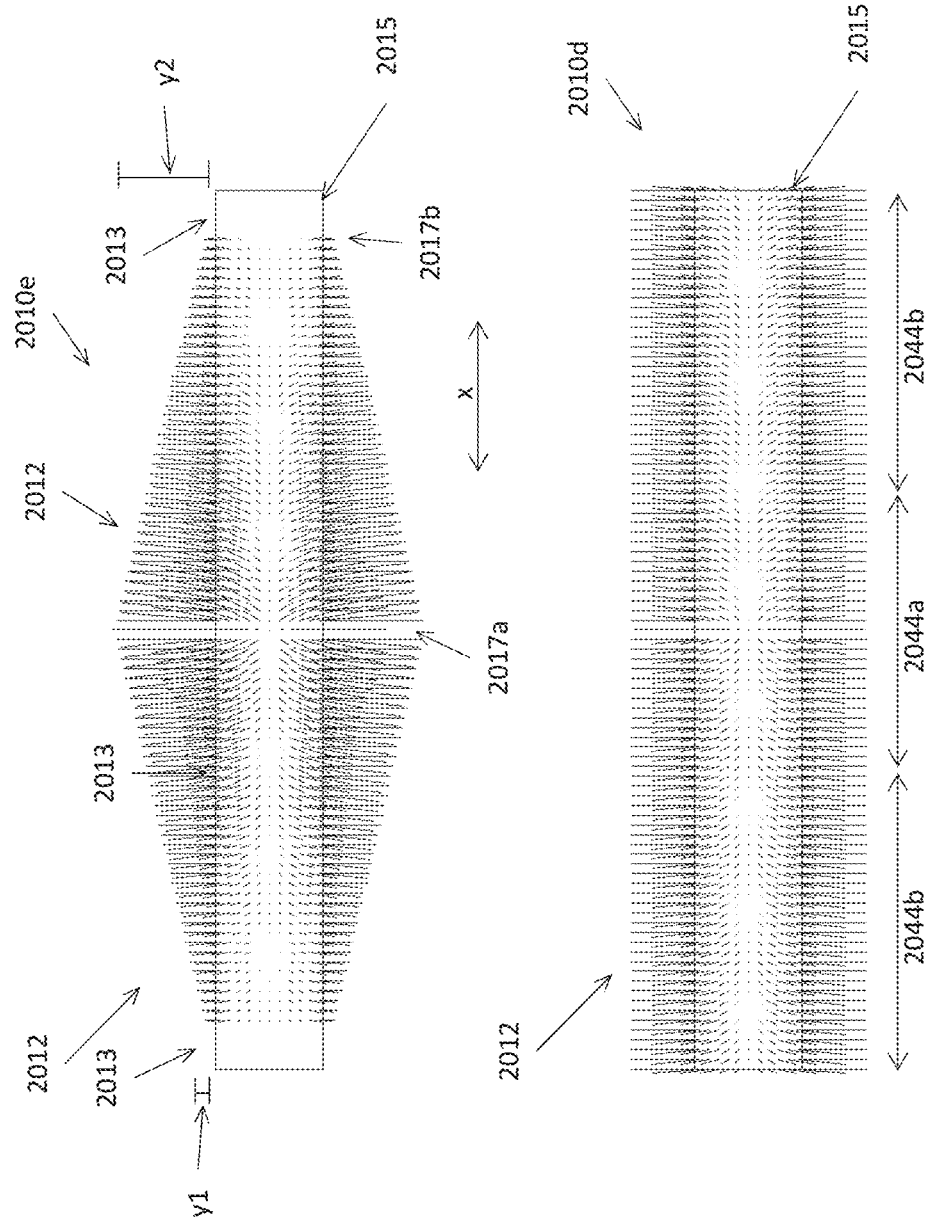

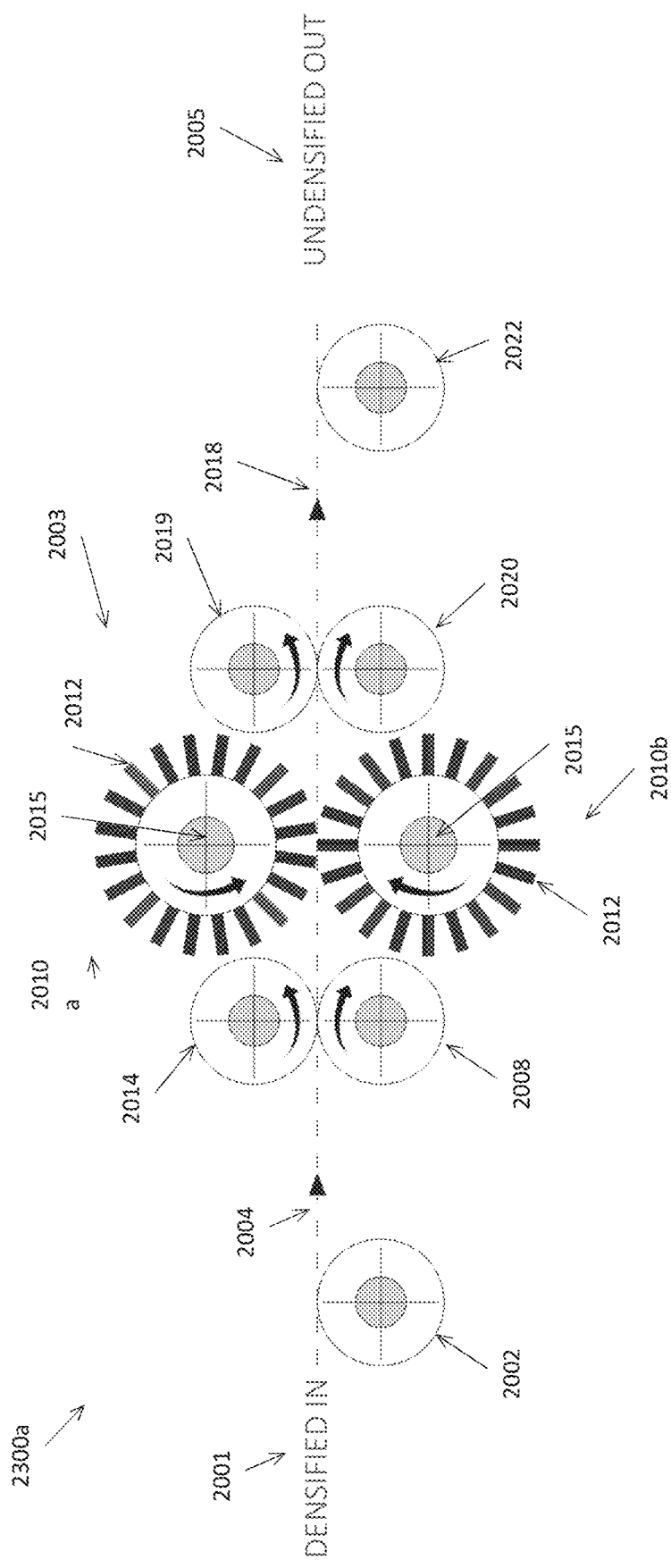

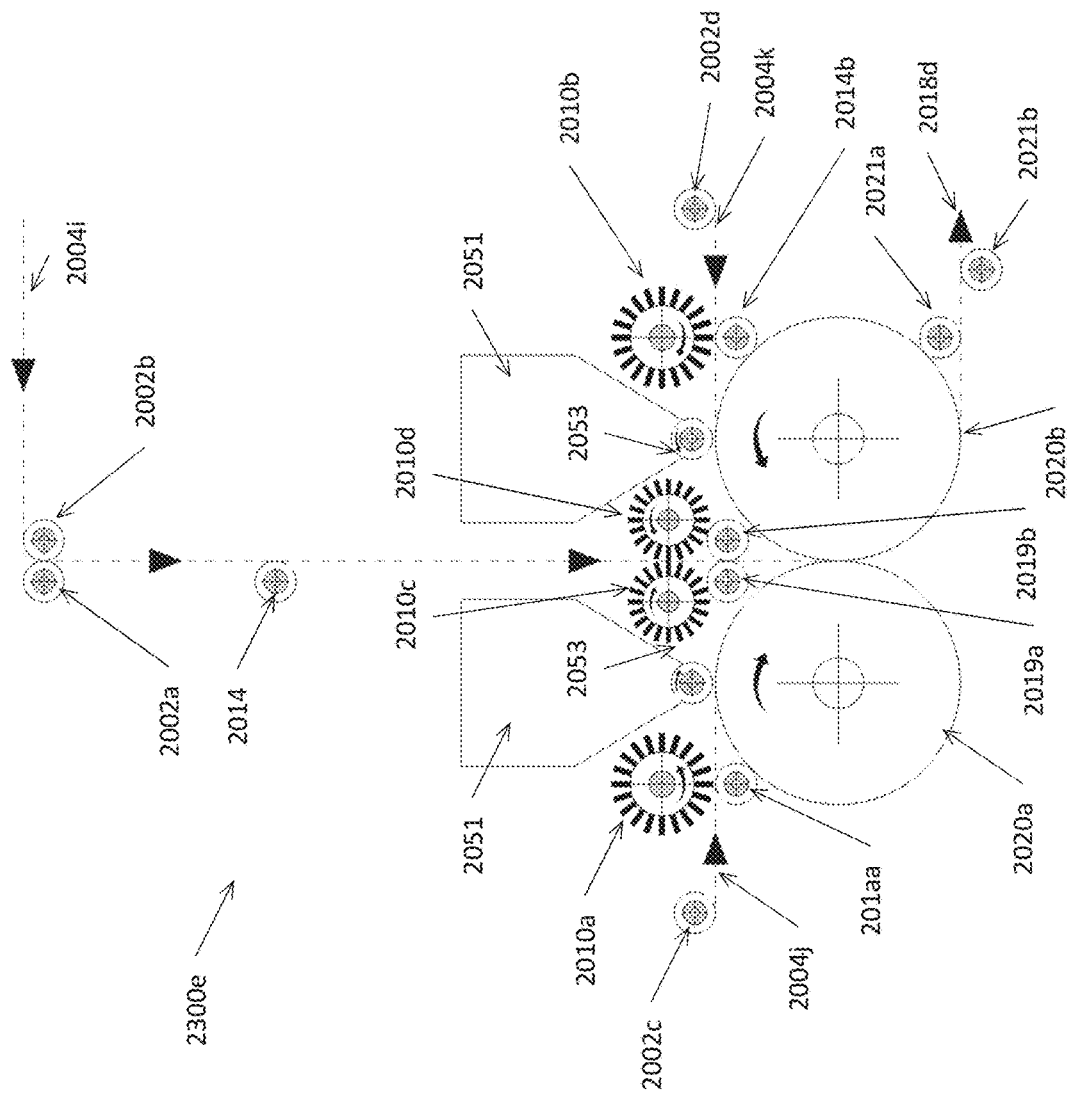

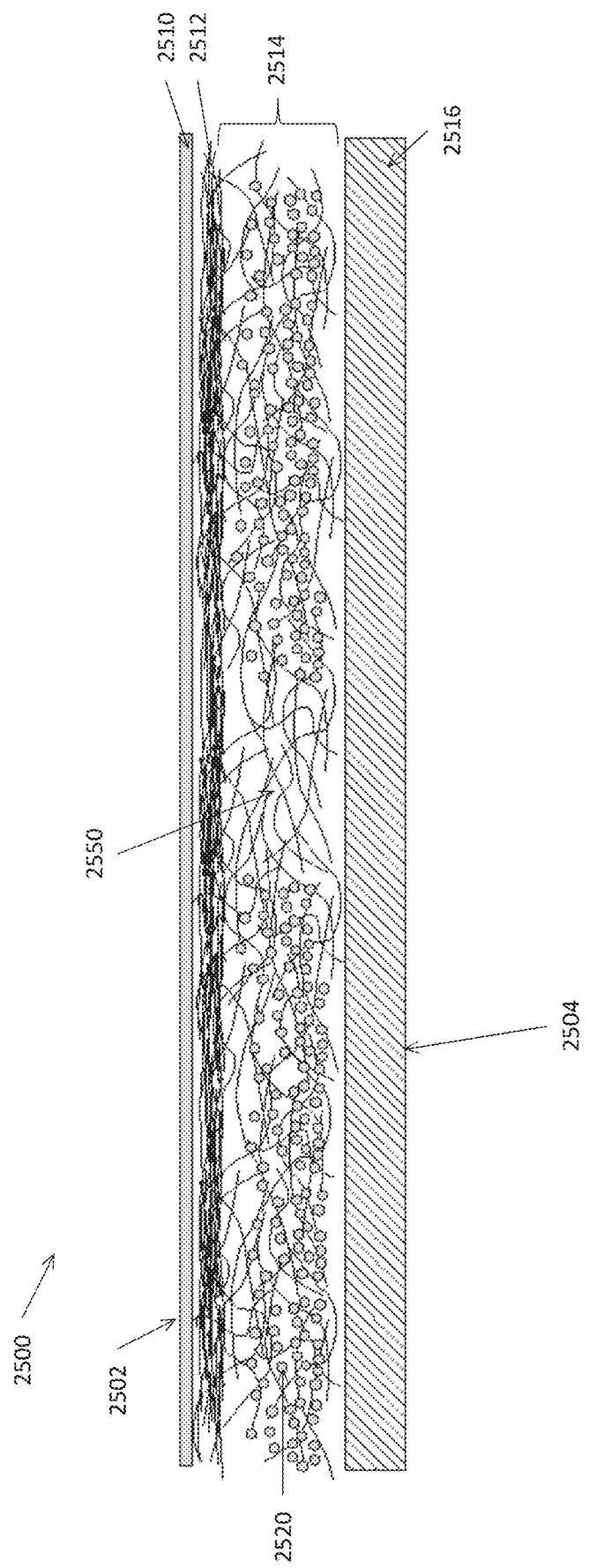

DISPOSABLE ABSORBENT ARTICLE AND ABSORBENT CORE COMPOSITE OR CONSTRUCTION FOR INCORPORATION THEREWITH, COMPONENTS THEREFOR OR THEREOF, AND SYSTEMS, APPARATUS AND METHODS OF MAKING THE SAME

CROSS-REFERENCE TO RELATED APPLICATIONS

The present application claims the benefit of U.S. Provisional Patent Application No. 62/646,870, filed on Mar. 22, 2018, the entirety of which is incorporated herein by reference and made a part of the present disclosure. The present application also claims the benefit of U.S. Provisional Patent Application No. 62/646,875, filed on Mar. 22, 2018, the entirety of which is incorporated herein by reference and made a part of the present disclosure. The present application also claims the benefit of U.S. Provisional Patent Application No. 62/646,880, filed on Mar. 22, 2018, the entirety of which is incorporated herein by reference and made a part of the present disclosure.

FIELD

The present disclosure relates generally to disposable absorbent articles, such as baby diapers, training pants, adult incontinence products, feminine hygiene articles, and the like. More particularly, the present disclosure relates to improved absorbent core components, disposable absorbent articles utilizing such absorbent core components, and methods of making or manufacturing same.

BACKGROUND

Most absorbent articles used today as baby diapers have a configuration similar to absorbent article 10 depicted in FIGS. 1A and 1B. FIGS. 1A, 1B, and 1C are reproduced from U.S. Patent Publication No. 2017/0224548. The conventional absorbent article 10 is shown in a laid out flat position in FIG. 1A, and in cross-sectional view in FIG. 1B. Absorbent article 10 includes outer-side fluid impermeable backsheet 101, a bodyside, fluid permeable nonwoven coverstock or topsheet 102, and absorbent construction 110 positioned between backsheet 101 and topsheet 102. An absorbent core provides the primary component of absorbent construction 110 and is designed and positioned to receive and retain bodily fluids. Absorbent construction 110 may also include at least one fluid management, fluid distribution and/or surge layer 103.

Backsheet 101 and topsheet 102 together form or define a chassis or central body 105 of absorbent article 10. Central body 105 may have first longitudinal end edge 112a, second longitudinal end edge 112b, and longitudinal centerline YY that extends through central body 105, bisecting both the first and second end edges 112a, 112b. Left and right side margins 106a, 106b extend from one end edge 112a to the other end edge 112b. Each end edge 112a, 112b partly defines waist regions 113a, 113b of the central body 105 which are generally characterized as having a lateral width significantly greater than a lateral width of a central region or crotch region 114 of central body 105. Waist regions 113a, 113b are designed to allow absorbent article 10 to be placed about the waist of the user. In this respect, first and second waist regions 113a, 113b may be described as front and rear waist regions 113a, 113b, respectively. The conventional absorbent article 10 further includes fastening means 104 attached to each side of the rear waist region 113a. Fastening means 104 are extendible and thereby, fastenable to a corresponding side of the front waist region 113b. Fastening means 104 helps to retain absorbent article 10 around and on the body of the user. Absorbent article 10 also includes a means for elasticizing 107 absorbent article 10 to maintain closure and sealing around the user's legs. Means of elasticizing 107 (e.g., leg cuffs and/or leg cutters) may be positioned outboard of and along longitudinal side margins 106a and 106b of the absorbent construction 110. Referring to FIG. 1A, the conventional absorbent construction 110 is centrally positioned in and about crotch region 114 of absorbent article 10.

Currently, most diaper cores are made from mixtures of fibers and superabsorbent particles, specifically cellulose based fibers derived from wood pulp and superabsorbent particles (SAP) derived from polyacrylic acid derivatives. An absorbent composite that is particularly suited for application in or with the disposable absorbent articles introduced herein is described in U.S. Pat. No. 6,540,853 (the '853 patent). SAP-nonwoven absorbent composites of the type disclosed in this patent reference are available to the diaper manufacturing process in roll form and allow much greater freedom for the design of absorbent cores. Nevertheless, because fluff pulp-superabsorbent cores are generally provided as a continuous stream or web of absorbent material, the simpler and most cost-efficient processes require the absorbent core to be maintained in a generally rectangular shape. These cores are typically formed into rectangular shapes that are designed for incorporation into an absorbent article. The core shape, particularly its width, is maintained at dimensions that accommodate placement within a diaper corresponding with the crotch area of the user.

Moreover, it is preferred in many applications for the absorbent core to take on a nearly hourglass shape. Such diaper cores are known in the art as providing a narrower crotch region that presents a better fit and comfort for the user. The hourglass shape also provides wider regions at the longitudinal ends of the core, which enhances the absorbency and leakage control capability of the diaper at those regions above the central crotch region. FIG. 1C illustrates another prior art disposable absorbent article 10'. The absorbent article 10' employs a design in which an absorbent core 110' is reduced in width in the crotch region 114', but is wider at the front and rear waist regions 113a', 113b'. The result is an absorbent core 110' having a more hourglass shape. To achieve this desired hourglass shaped core, a rectangular absorbent core section is cut from a continuous web of absorbent material and shaped further, particularly in forming the narrow central region.

As known in the art, the preferred diaper assembly process is a substantially linear and efficient machine directed process that produces a high volume of packaged products. Because of the nature of the consumer product as a disposable, high frequency of use item and the abundance of competing products and alternative products (e.g., reusable cloth diapers), it is imperative to maintain the low cost of the final product. Accordingly, it is also imperative to control the complexity of the manufacturing process and to minimize steps and material waste. This presents a technical challenge to one attempting to create alternative shapes and functionalities in the conventional disposable absorbent article. For example, although an hourglass shaped diaper core is generally desirable or, in some applications, a core having distinct areas of absorbency, additional cutting or forming steps or increased material cost may make the alternative design less effective.

In any event, absorbent core configurations achieving further functionalities and/or improved fit and comfort for the sure are desirable. However, caution must be exercised to minimize material cost and manufacturing complexity.

SUMMARY

Some embodiments include an absorbent core for incorporation into a disposable absorbent article. The absorbent core includes a first nonwoven; a second nonwoven; and absorbent material. The absorbent material is positioned between the first and second nonwovens, embedded within the first nonwoven, embedded within the second nonwoven, or combinations thereof. At least one section of the second nonwoven includes bulkified nonwoven.

Other embodiments include a system for bulkifying a nonwoven. The system includes a nonwoven supply; a nonwoven manipulator positioned to receive a nonwoven from the nonwoven supply and bulkify the nonwoven; and a collector positioned to receive the bulkified nonwoven from the nonwoven manipulator.

Other embodiments include a method of bulkifying a nonwoven. The method includes: mechanically manipulating one or more surfaces of a nonwoven, thermally manipulating the one or more surfaces of the nonwoven, or combinations thereof, forming a bulkified nonwoven; wherein the bulkified nonwoven exhibits a bulk density that is less than the nonwoven, and wherein the bulkified nonwoven exhibits a void volume that is greater than the nonwoven.

Other embodiments include an absorbent core. The core includes a first nonwoven layer; a second nonwoven layer coupled with the first nonwoven layer; a third nonwoven layer engaged with the second nonwoven layer opposite the first nonwoven layer; and absorbent material embedded within the second nonwoven layer.

Other embodiments include a method of making an absorbent core. The method includes depositing bicomponent fibers onto a nonwoven layer, forming a web of fibers. Settling of the fibers forms a higher density region of the bicomponent fibers at a bottom of the deposited web and a lower density population of the bicomponent fibers at a top of the deposited web. The method includes depositing SAP onto the web of fibers.

Other embodiments include an absorbent core. The core includes a first nonwoven; a second nonwoven; absorbent material, wherein the absorbent material is positioned between the first and second nonwovens, embedded within the first nonwoven, embedded within the second nonwoven, or combinations thereof and a loose fiber layer positioned between the first and second nonwovens.

Other embodiments include a method of forming an absorbent core having a fiber layer. The method includes depositing loose fibers onto a first nonwoven layer; and applying a second nonwoven layer over the loose fibers.

Other embodiments include an absorbent core. The core includes a first nonwoven; a second nonwoven; and an absorbent material layer between the first and second nonwoven, wherein the absorbent material layer includes absorbent material-containing lanes and absorbent material-free lanes. Embossing lines bind the first nonwoven with the second nonwoven. The embossing lines are coincident with the absorbent material-free lanes, such that the first nonwoven is embossed to the second nonwoven at locations corresponding to the absorbent material-free lanes.

Other embodiments include a multilayer absorbent core. The core includes a first, bodyside nonwoven; a second nonwoven; a first absorbent material layer positioned between the first and second nonwovens, embedded within the first nonwoven, embedded within the second nonwoven, or combinations thereof; a third nonwoven; and a second absorbent material layer positioned between the second and third nonwovens, embedded within the second nonwoven, embedded within the third nonwoven, or combinations thereof.

These exemplary aspects and other aspects of the disclosure are illustrated through the Figures identified and briefly described below and/or the Detailed Description or the appended claims.

BRIEF DESCRIPTION OF THE DRAWINGS

FIG. 1A is a simplified plan view illustration of a prior art disposable absorbent article suitable for incorporating an absorbent core composite in accordance with the present disclosure therein;

FIG. 1B is a simplified cross-sectional view illustration of a prior art disposable absorbent article suitable for incorporating an absorbent core composite or construction in accordance with the present disclosure therein;

FIG. 1C is a simplified plan view illustration of a prior art disposable absorbent article suitable for incorporating an absorbent core composite in accordance with the present disclosure therein;

FIG. 2 is a flat, laid out, plan view of a diaper with a portion of the top layer removed, revealing the position of a multilayer absorbent core composite in accordance with the present disclosure therein;

FIG. 3 is a flat, laid out, plan view of a diaper with a portion of the top layer removed, revealing the position of a multilayer absorbent core composite in accordance with the present disclosure within a three-part chassis of the diaper;

FIG. 4A is a simplified, cross-sectional view of a multilayer core composite or construction, including two absorbent core material layers, according to the disclosure;

FIG. 4B is a simplified, cross-sectional view of a multilayer core composite or construction, including three absorbent core material layers, according to the disclosure;

FIG. 4C is a simplified, cross-sectional view of a multilayer core composite or construction, including four absorbent core material layers each beneath a non-woven layer, according to the disclosure;

FIG. 4D is a cross-sectional, elevation view of a multilayer core composite or construction, including multiple material layers of varying dimensions;

FIG. 4E is a cross-sectional, elevation view of a multilayer core composite or construction, including multiple material layers of varying dimensions, including thickness and depth;

FIG. 4H is a cross-sectional, elevation view of a multi-layer core composite or construction, including multiple material layers of varying dimensions, including varying thickness, width and/or depth, and including absorbent material layers featuring absorbent material-free zones or lanes;

FIG. 4I is a cross-sectional, elevation view of a multi-layer core composite or construction, including multiple material layers of varying dimensions, including varying thickness, width and/or depth, and including absorbent material layers featuring absorbent material-free zones or lanes;

FIGS. 4K-4M are cross-sectional views of absorbent core composites or constructions with layers of varying content, basis weight, and arrangement, providing varying fluid flow and retention properties within and/or through the absorbent core composites or constructions;

FIG. 6A is a perspective, exploded view of a multi-layer absorbent core composite or construction having multiple absorbent core material layers, which is suitable for incorporation into a disposable absorbent core composite;

FIG. 6B is a perspective, exploded view of a multi-layer absorbent core composite or construction having at least one absorbent core material layers featuring one or more absorbent material-free regions, which is suitable for incorporation into a disposable absorbent core composite;

FIGS. 7A-7G are plan views of non-contiguous absorbent material layers featuring material-free zones;

FIG. 8 is a perspective, exploded view of an absorbent core composite or construction having cross direction (CD) SAP-free lanes in an upper absorbent material layer, and machine direction (MD) SAP-free lanes in a lower absorbent material layer;

FIG. 9 is a perspective, exploded view of an absorbent core composite or construction having embossing lines aligned with SAP-free lanes;

FIGS. 9A and 9B are elevation views of an absorbent core composite or construction having embossing lines aligned with SAP-free lanes, in a flat and folded configuration, respectively;

FIG. 12 is another simplified, perspective view of a system and a process for applying an absorbent material layer featuring absorbent material-free zones;

FIGS. 13A-13C are elevation views of a multi-layer absorbent core composite or construction, including a loose fiber layer;

FIGS. 15A and 15B are photographs of a bulky nonwoven before and after bulkification, respectively;

FIGS. 16A-16D are cross-sectional views of sectionally bulkified bulky nonwovens, with and without SAP;

FIGS. 18A-18F are cross-sectional views of various absorbent core composites or constructions in accordance with the present disclosure;

FIGS. 19A and 19B are cross-sectional views of an absorbent core composite or construction, including bulkified bulky nonwoven;

FIG. 20 is a schematic of a system and process for bulkifying a nonwoven substrate, according to the disclosure;

FIGS. 20A-20D are schematics of various brushes suitable for use in bulkifying a nonwoven substrate;

FIGS. 23A-23E are schematics of systems and processes for bulkifying a nonwoven substrate;

FIG. 25 is an elevation view of an absorbent core composite or construction in accordance with certain aspects of the present disclosure.

DETAILED DESCRIPTION

Figure 1D:
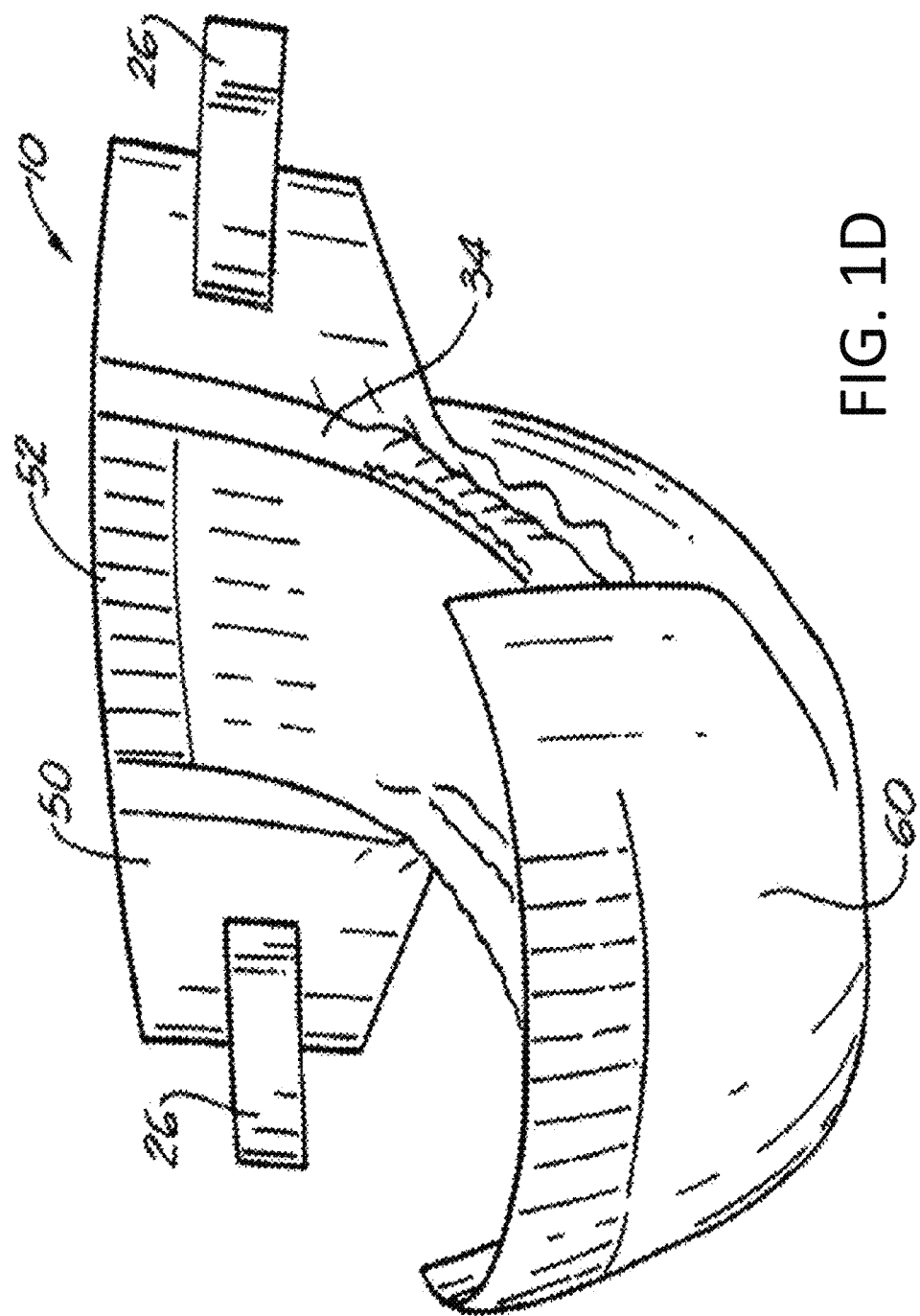
FIG. 1D is a perspective view of a disposable absorbent article within which an absorbent core composite in accordance with the present disclosure may be incorporated.

The present disclosure provides, generally, for disposable absorbent articles, such as baby diapers, training pants, adult incontinence products, and feminine hygiene articles. More particularly, the present disclosure provides for improved absorbent core components, disposable absorbent articles utilizing such absorbent core components, and methods of making or manufacturing same.

Certain embodiments of the present disclosure are particularly directed to achieving absorbent core configurations that easily accommodate the conventional disposable absorbent article and maintain comfort and fit for the user. Such absorbent core configurations, and disposable absorbent articles employing same, may be readily made at high volume without overburdening the manufacturing process with additional steps and material waste. In this respect, the disclosure provides improved hourglass or nearly hourglass shaped core constructions by providing and presenting more usable and flexible core components or core elements and incorporating these components into highly effective diapers and training pants.

In one embodiment, a disposable absorbent article is provided having a central body defining a first waist end region including a first longitudinal end edge, a second waist end region spaced longitudinally from the first waist end region and including a second longitudinal end edge, and a crotch region positioned therebetween. An absorbent core composite is situated between the end edges, and includes at least one nonwoven layer and at least one absorbent material layer, and optionally at least one loose fiber layer. In some aspects, each nonwoven layer of the absorbent core composite is a slitted nonwoven, a bulky nonwoven (e.g., an air-through nonwoven), or a bulkified nonwoven (fully or sectionally bulkified). The absorbent material layers may include SAP-free lanes and SAP-containing lanes.

In certain embodiments, the positions of the components of the absorbent core composites disclosed herein are arranged to provide desired fluid handling properties and capabilities, such as fluid flow, fluid absorption, and fluid dispersion properties and capabilities to the absorbent core composite. The absolute and relative positions of the nonwoven layers and absorbent material layers within the absorbent core composite, the sections within each respective nonwoven layers or absorbent material layer, and the sections within one layer relative to the sections within another layer may be arranged to provide such desired fluid handling properties and capabilities. The position of nonwoven (NW), bulky nonwoven (BNW), bulkified bulky nonwoven (BBNW), slitted NW, SAP-containing layers, SAP-containing lanes, and SAP-free lanes may selectively arranged within the absorbent core composite. Each of the various layers and arrangements thereof disclosed herein may be combined in various combinations to provide various absorbent core composites in accordance with the present disclosure. The absorbent core composites disclosed herein may include: (1) one or more nonwoven layers of various thickness, widths, lengths, SAP contents, and SAP dispersion amongst various layers (e.g., as shown and described with reference to FIGS. 4 and 4A-4S); (2) one or more absorbent material layers, with or without SAP-free lanes (e.g., as shown and described with reference to FIG. 6A-9); (3) one or more nonwoven layers having slits (e.g., as shown and described with reference to FIG. 10); (4) one or more loose fiber layers (e.g., as shown and described with reference to FIGS. 13A-13C); (5) one or more nonwoven layers either fully or sectionally bulkified (e.g., as shown and described with reference to FIG. 15A-19B); (6) one or more bicomponent fiber layers, including high and/or low density bicomponent fiber layers (e.g., as shown in FIGS. 25 and 26); (7) one or more airlaid layers (e.g., as shown in FIGS. 25 and 26); (8) or any combination thereof. Any such absorbent core composites may be incorporated into an absorbent article, such as those shown and describe with reference to FIGS. 1A to 1F.

Some embodiments relate to systems and/or processes for forming any of the absorbent core composites or articles disclosed herein. Such systems and/or processes may incorporate: (1) one or more of the features of the system shown in FIG. 5; (2) one or more of the features of the system shown in FIG. 11; (3) one or more of the features of the system shown in FIG. 12; (4) one or more of the features of the system shown in FIG. 14; (5) one or more of the features of the system shown in FIG. 20; (6) one or more of the features of any of the apparatus shown in FIGS. 20A-20C; (7) one or more of the features of the system shown in FIG. 21; (8) one or more of the features of the system shown in FIG. 23; (9) one or more of the features of any or all of the systems shown in FIGS. 23A-23E; (10) one or more of the features of the system shown in FIG. 24; (11) or any combination thereof.

The absorbent core composites described herein may have increased loftiness (which promotes comfort and softer regions) and increased void space out in an otherwise flat core, without significant void volume. Increased void space or volume serves to provide a temporary fluid holding and fluid transporting space. Such space provides a place for fluid within the confines of the core to temporarily reside during the time (seconds) that it takes for superabsorbent to activate and absorb the fluid. Such voids or spaces also act to channel fluid, and facilitate dispersal of fluid exudates.

An advantageous application of the various concepts and embodiments of the present disclosure is one directed to baby diapers. For this reason, much of the exemplary descriptions provided herein are directed to diapers. The disclosure extends, of course, to applications beyond diapers.

Diaper

Figure 1E:
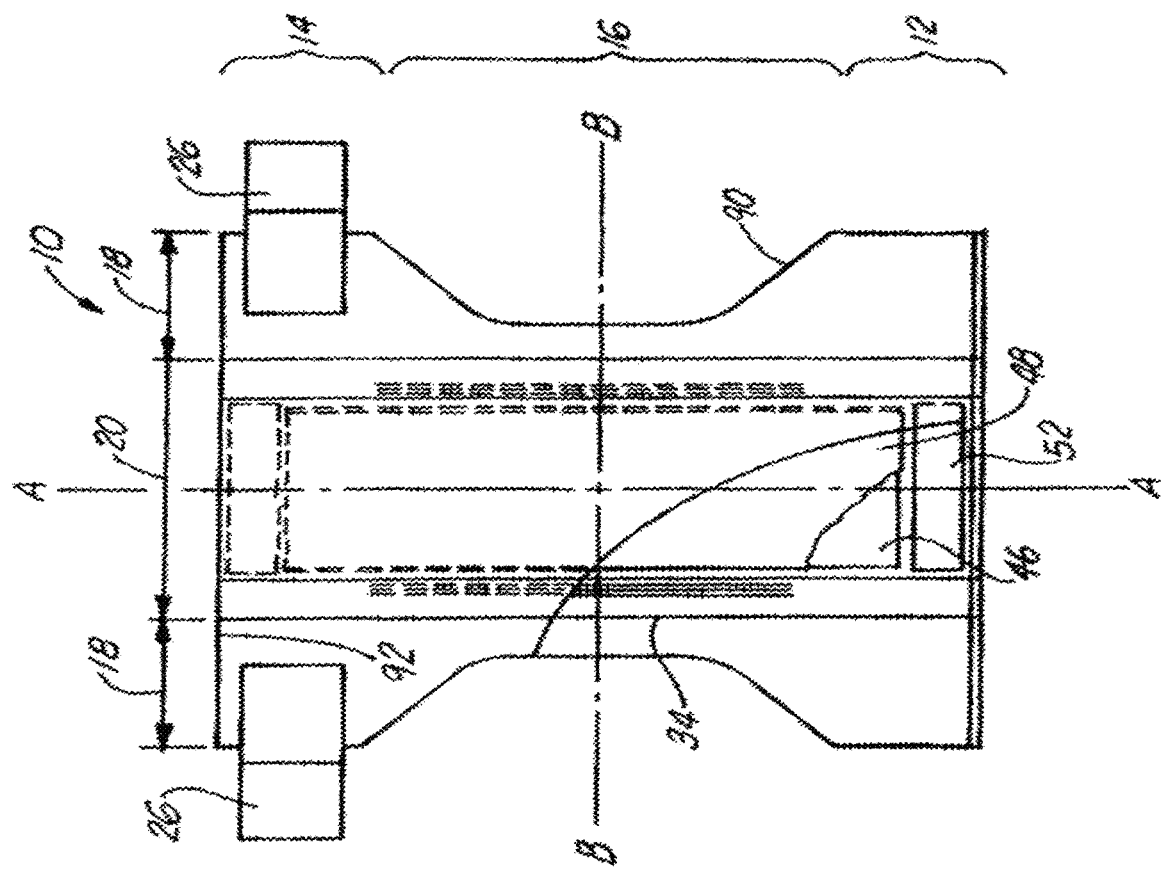
FIG. 1E is a top plan view of the disposable absorbent article of FIG. 1D in a flat and extended condition.
Figure 1F:
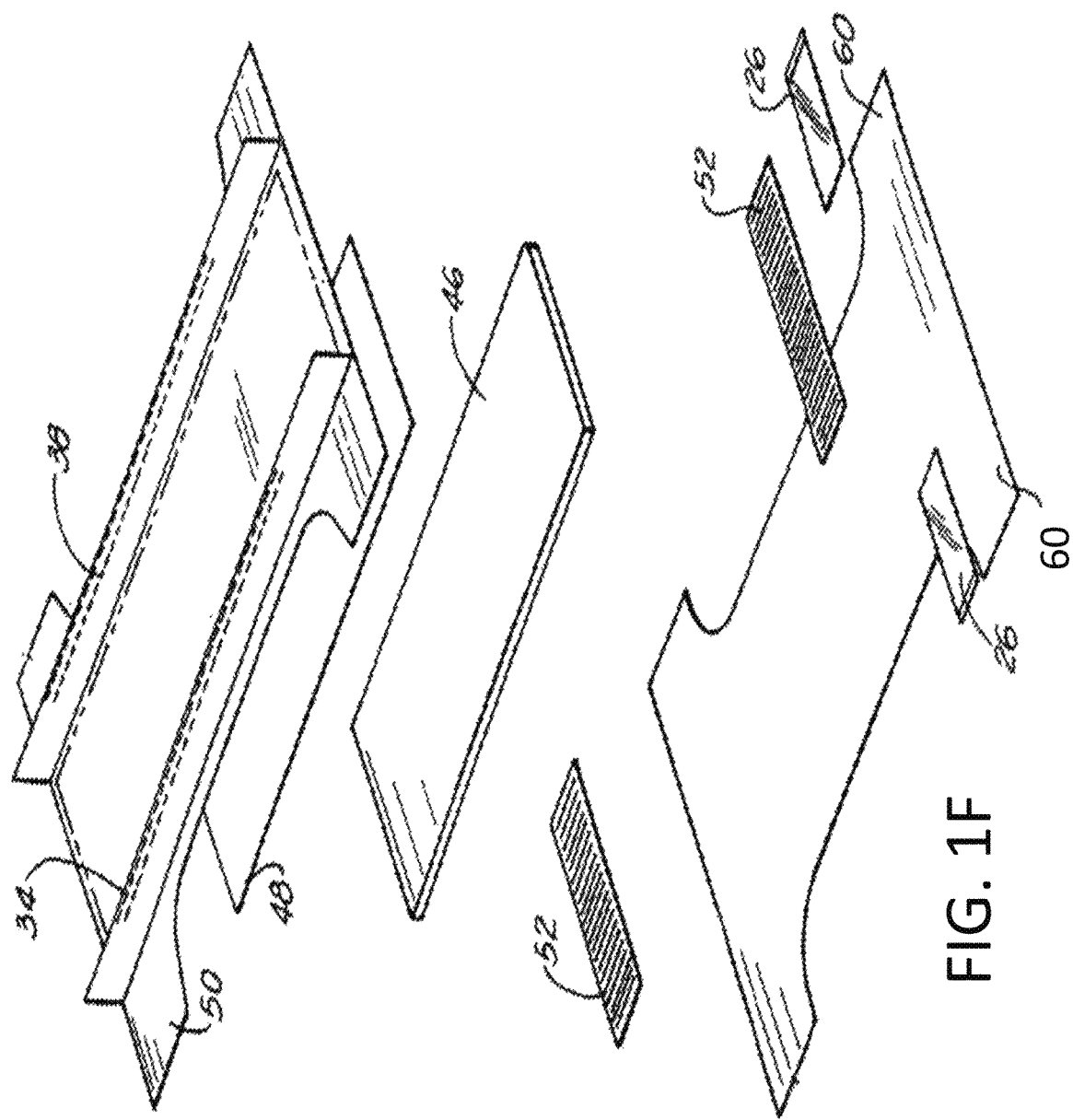
FIG. 1F is an exploded view of the disposable article of FIG. 1D.

FIG. 1D is a perspective view of a disposable absorbent article embodying the absorbent composite; FIG. 1E is a top plan view of the disposable absorbent article of FIG. 1D in a flat and extended condition; and FIG. 1F is an exploded view of the disposable article of FIG. 1D. With reference to FIGS. 1D-1F, a disposable absorbent article in the form of diaper 10 is shown. Diaper 10 includes topsheet 50, backsheet 60, and absorbent core 46. Diaper 10 includes upstanding barrier cuffs 34, which extend longitudinally along diaper 10 and are elasticized to conform to the buttocks of the wearer. Additionally, diaper 10 includes elastic band 52 and fastening elements 26. Elements 26, in use, extend to and engage the corresponding opposing end of diaper 10 to secure diaper 10 about the wearer. The web structure shown in FIG. 1E may be subsequently trimmed, folded, sealed, welded and/or otherwise manipulated to form a disposable diaper 10 in a finished or final form. To facilitate description of diaper 10, the description refers to a longitudinally extending axis A-A, a laterally extending central axis B-B, a pair of longitudinally extending side edges 90, and a pair of end edges 92 which extend between side edges 90. Along the longitudinal axis A-A, diaper 10 includes first end region or front waist region 12, second end region or back waist region 14, and crotch region 16 disposed therebetween. Each of front and back waist regions 12, 14 is characterized by a pair of ear regions or ears 18, which are located on either side of central body portion 20 and extend laterally from side edges 90. Fastening structure 26 (e.g., a conventional tape fastener) is affixed to each of the ears 18 along the back waist region 14 of diaper 10. When diaper 10 is worn about the waist, front waist region 12 is fitted adjacent the front waist area of the wearer, back waist region 14 is fitted adjacent the back waist area, and crotch region 16 fits about and underneath the crotch area. To properly secure diaper 10 to the wearer, ears 18 of back waist region 14 are brought around the waist of the wearer and toward the front and into alignment with ears 18 of front waist region 12. The securing surface may be located on or provided by the interior or exterior surface of front waist region 12. Alternatively, fasteners 26 may be located on ears 18 of front waist region 12 and made securable to ears 18 of back waist region 14. Cuffs 34 may be equipped at least with one or more spaced apart, longitudinally elastic members 38. It will be shown below that any of these diaper elements or a combination of these elements may be constructed with or using any of the absorbent core composites disclosed herein. Additionally, an acquisition layer 48 could be added to improve performance.

The present disclosure is directed, in one respect, to developing and utilizing alternate absorbent core designs that maintain or improve the comfort and fit of the absorbent article while also maintaining or improving the absorbency and sealing capability of the core and the absorbent article. Various embodiments of the disclosure place particular emphasis on selective placement and shaping of commercially available absorbent materials, while maintaining the cost efficiency and manufacturability of the resultant disposable absorbent article. In one aspect, emphasis is directed to selective placement and varying of absorbent materials along the longitudinal and/or lateral direction (i.e., absorbent profile) to achieve a certain functionality and efficiency. Selected absorbent profiles provide regions or expanse within the resultant core construction exhibiting advantageous or optimal absorbent or absorption capacity per unit area (sometimes referred to herein as "absorbent density" or "absorption density"). As mentioned briefly above, various aspects of the disclosure are particularly applicable to baby diapers (and also, training pants). For this reason, much of the description and illustrations herein are provided in the context of diapers. It will become apparent to one skilled in the art provided with the present disclosure, however, that the disclosure, and its various aspects, are also applicable to other disposable absorbent articles and absorbent core constructions. The detailed descriptions and illustrations of inventive embodiments should not, therefore, be construed as limiting the disclosure.

FIGS. 2 and 3 depict disposable absorbent article 20, in the form of a diaper, embodying various aspects of the present disclosure, including an improved absorbent core construction 210. Absorbent article 20 has backsheet 201 (or 201a and 201b in FIG. 3) and topsheet 202 that is shown mostly removed in FIGS. 2 and 3 to reveal absorbent core construction 210. Together, the combination of backsheet 201 and topsheet 202 helps to define a chassis or central body 205 of absorbent article 20. Central body 205 also provides first waist end region 213a, including first longitudinal end edge 212a (or simply, first end edge 212a); second waist end region 213b, including second longitudinal end edge 212b (or second end edge); and longitudinal centerline YY extending the length of central body 205 to bisect first and second end edges 212a, 212b. Waist regions 213a, 213b may be identified with the portions of absorbent article 20 and central body 205 that are generally positioned vertically, and above and about the thighs of the user when absorbent article 20 is worn.

Central body 205 at least partially defines crotch region 214, located generally centrally between first and second waist regions 213a, 213b and about lateral centerline XX. As is readily known to consumers and manufacturers alike, much of crotch region 214 is positioned generally horizontally and/or is curved upwards when article 20 is in use. Absorbent core construction 210 may be centered and supported about crotch region 214 between backsheet 201 and topsheet 202. In such an arrangement, absorbent core construction 210 is placed in a nearly optimal position to receive bodily exudates when absorbent article 20 is in use. Absorbent core construction 210 is also described herein as having first longitudinal end 207a (or simply, first end 207a) and second longitudinal end 207b (or second end 207b) spaced longitudinally from first end 212a and second end 212b of central body 205, respectively. In some embodiments, first and second ends 207a, 207b of absorbent core construction 210 may not be clearly defined, e.g., as an edge, line, or point. In such embodiments, the terms first and second ends are used to identify generally the margins of the absorbent construction or absorbent core spaced furthest along the longitudinal direction from lateral centerline XX. In other embodiments, the first and second ends may not be defined by one core component or element, but by multiple components or elements.

To facilitate description and illustration, absorbent core construction 210 is often illustrated and described as consisting only of layers of absorbent materials, as illustrated in FIGS. 2 and 3. Absorbent core construction 210 is, therefore, simply referred to herein as absorbent core 210. As will also become apparent with the descriptions of various embodiment of the disclosure, absorbent core 210 may be composed of more than one independently applied core component or absorbent core element having significantly enhanced absorbent properties. Absorbent core 210 may be constructed from any of various combinations of nonwoven material, absorbent fibers and/or superabsorbent particles. The absorbent core may have properties or characteristics (e.g., absorbent properties) so as to achieve a particular overall absorbent core design or capability. The absorbent core may also take on very different shapes and configurations, as will be illustrated in other embodiments described in this Detailed Description.

The shape of the core elements may be formed and applied by any number of suitable means, including vacuum forming techniques, cutting with the aid of rotary dies, and cutting using waterjet devices. Referring to FIG. 3, the width of absorbent core element 210 defines first end 217a. As applied on absorbent article 20, each shaped absorbent core 210 may be positioned in alignment (co-incident) with longitudinal centerline YY of absorbent article 20 with end 217a located proximate one of waist regions 213 of central body 205. Absorbent core 210 is positioned at the center of crotch region 214.

Referring to FIG. 2, absorbent core 210 may have a narrow mid-section or central region (not shown) that is positioned proximate lateral centerline XX in crotch region 214. This narrowing of the central region translates to improved user comfort as well as compatibility with the leg sealing components of absorbent article 20. A greater amount of absorbent material per unit of area may be in the narrower central region to provide for greater or increased absorbency in the portion of absorbent core 210 that has the greatest need for it, forming a primary absorbent region 250. The resultant absorbent core 210 may be wider upward from crotch region 214 (not shown) toward the front and rear longitudinal ends 207a, 207b (i.e., the upper absorbent regions). This increased expanse of core material increases the absorbent coverage in these upper regions of absorbent core 210. The extra core material also helps to seal and prevent leakage in and from waist regions 213 of article 20.

With reference to FIG. 3, to facilitate the present description, absorbent core 20 may be described as having a narrow central region or midsection M0, and a pair of end regions E1, E2 on opposite sides of midsection M0. The locations or bordering of these regions are only generally defined (for purposes of the present description). In various embodiments, primary absorbent region 250 may be situated substantially in central region M0, but may extend longitudinally into end regions E1, E2. End regions E1, E2 may also be referred to as upper absorbent regions as these regions are generally positioned above midsection M0 when absorbent article 20 is in use.

In some embodiments, there is an increase and decrease in the concentration of absorbent material in absorbent article 20 along longitudinal centerline YY from one waist end region 213a to the other waist end region 213b. Therefore, the longitudinal absorbency profile of article 20 from one end 212a to the other end 212b may vary. Thus, the absorbent construction may have marked variations in absorbency (absorbent capacity per unit area (e.g., square inch) or absorbent densities) along specified directions or at specified locations on central body 205. As explained above, greater concentrations of absorbent material provide high absorbency at crotch region 214 of absorbent article 20. Absorbent article 20 may also exhibit absorbency per unit area near the waist regions 213a, 213b as imparted by the end regions E1, E2 of the core 210, although it may be significantly decreased from that which characterizes the primary absorbent region 250. Nevertheless, absorbent core 210 may extend sufficiently upward into the waist regions 213a, 213b to expand and extend the absorbent coverage of article 20. Beyond absorbent core 210, the absorbency (and absorbency per unit area) of disposable absorbent article 20 drops off significantly as expected.

In the descriptions provided herein, the absorbent core may be described as a profiled core. In the present context, this description relates to the varying absorbency imparted upon the absorbent article along specific directions or at specified locations on the central body. It also refers to the varying physical contour of the resultant absorbent core, which is illustrated by the absorbent core profiles. It should be noted that in some applications, variations in absorbent densities may be achieved by using core materials of different absorbent properties in lieu of, or in addition to core materials of substantially similar absorbent properties.

In developing the various configurations provided herein, optimal use of absorbent materials is an important design consideration. A balance is often struck between achieving high absorbency in the article and maintaining low material cost. This also requires controlling over use and over concentration of absorbent material so as to prevent lumps from forming or cause components to impinge upon the user's skin, thereby compromising the comfort of the user. Without care, an irregular core profile may also negatively impact the shape of the absorbent core when worn and lead to stressing the leakage prevention mechanisms of the article (e.g., elasticized leg cuffs and leg gathers). Thus, aside from cost considerations, the absorbent profiles proposed are not simply the result of laying out as much absorbent material as possible.

As discussed above, the design considerations accounted for manufacturability and ease of assembly. Very often these attributes translate to cost efficiency in the resultant product, as well as increased quality of construction. In this respect, the present disclosure achieves improved product designs, including configurations that achieve specific absorbent properties and/or specific shapes without sacrificing or burdening manufacturability. One feature of the disclosure that helps achieve these objectives is the use of substantially identical core elements to create various core shapes, including irregular shapes (e.g., non-rectangular), and absorbent profiles. The selection of core elements also provides design and manufacturing flexibility.

As an example, the configuration and selection of the absorbent core composite, and the constituent layers thereof, allows the manufacturer of absorbent article 20 to readily vary or fine tune the shape of absorbent core 210 and disposable absorbent article 20 by adjusting the position and size of core 210. In this way, the overall length of absorbent core 210 may be adjusted to accommodate different size absorbent articles. Such a linear adjustment may be easily made in a substantially linear assembly process of the absorbent core. This adjustment also allows desired lateral or longitudinal absorbent profiles to be achieved, including enlarging or reducing the primary absorbent region. The manufacturer can also make further modifications to the absorbent profile and the overall dimensions of the core by adjusting the length and widths of the individual absorbent core elements.

Definitions

For purposes of the present description of various aspects of the disclosure, an "absorbent core composite or construction" refers to a cohesive arrangement of multiple components or sections, including one or more sections or components composed of or populated by an absorbent material. As with the term "composite", the term "construction" may, in one respect, refer to such a cohesive arrangement of multiple sections or components that together define an absorbent body or portion thereof. Such an absorbent body may then be incorporated into a disposable absorbent article or garment and provide an absorbent core for the article. In some diaper or training pants applications, a cover layer (e.g., a nonwoven or nonwoven tissue) may encase or lay above the absorbent core (and may be included in defining the absorbent core of the article). Further, the absorbent article may provide one or more impermeable back sheets, one or more topsheets, one or more acquisition distribution layers (ADLs), and/or one or more tissue layers about or adjacent the absorbent core. The "absorbent core composite" disclosed herein includes composites of at least one nonwoven layer and at least one absorbent material layer. The "absorbent core composites" is also referred to herein as an "absorbent core" or an "absorbent composite" or a "core composite" or an "absorbent core construction" or an "absorbent construction" or a "core construction" or a "core" or an "absorbent core composite or construction".

As used herein, "NW" refers to a nonwoven fabric. Each nonwoven layer of any of the absorbent core composites disclosed herein, including, but not limited to, those which are subjected to bulkification, may be a bulky nonwoven (also referred to as a high loft nonwoven), such as an air-through nonwoven. At least some of the nonwoven layers disclosed herein may be a meltblown nonwoven, a spunbound nonwoven, or any combination thereof (e.g., such as a spunbound-meltblown-spunbound (SMS) nonwoven). The nonwovens disclosed herein may be airlaid nonwovens. Furthermore, each nonwoven layer disclosed herein may be a "tissue" or "tissue layer", which is a cellulose-based (paper) nonwoven as opposed to a synthetic nonwoven. Fibers of any of the nonwovens disclosed herein may include, but are not limited to, fibers composed of polypropylene (PP), polyethylene (PE), polyethylene terephthalate (PET), polylactic acid (PLA), other polyolefins, copolymers thereof and any combination thereof, including bicomponent fibers. The fibers may be treated with a surface-active agent, surfactant, to modify the surface tension of the fibers so that they are hydrophilic. In some aspects, the NW layers used in the absorbent core composites disclosed herein are selected based upon pore size of the fabric, fiber wettability of the fabric, or combinations thereof.

As used herein, the density of a nonwoven, including of a bulky nonwoven, is determined in accordance with the following Equation 1: Density($\rho$)=mass(m)/volume(v)=mass/(length(l)×width(w)×thickness(t)). The International Nonwovens and Disposables Association (INDA) and the European Disposables and Nonwovens Association (EDANA) provide test methods that, although do not include a specific method for density, provide tests that allow one skilled in the art to arrive at the density value using the above Equation 1. Test method NWSP 120.2.R0 (15), set forth by INDA and EDANA, provides a means to measure the thickness (t) of a bulky nonwoven, also referred to as a high loft nonwoven. Test method NWSP 130.1.R0 (15), set forth by INDA and EDANA, provides means to measure the mass per unit area or basis weight (bw). Once thickness of the bulky nonwoven and the mass per unit area of the bulky nonwoven is determined in accordance with NWSP 120.2.R0 (15) and NWSP 130.1.R0 (15), the density may be determined:

$$\text{Density}(\rho)=m/v=m/(l\times w\times t) \quad \text{(Equation 1)}$$

$$\text{Mass per unit area (bw)}=m/(l\times w) \quad \text{(Equation 2); therefore,}$$

$$\rho=bw/t \quad \text{(Equation 3)}$$

As used herein "BNW" refers to a "bulky nonwoven". Bulky nonwovens, in comparison to non-bulky nonwovens, are thicker at low to medium basis weights. Air-through nonwoven is a type of bulky nonwoven, and denotes the manufacturing method for production of nonwoven where hot air is blown through a carded nonwoven to thermally bond the fibers. Other bulky nonwoven types include resin bonded nonwovens, and other carded nonwovens. The "bulky nonwoven" referred to herein may be and provides, an open, fibrous network or web of hydrophilic but non-absorbent fibers. Furthermore, as used herein, a bulky nonwovens is a fibrous web material having a thickness of between 100 μm and 10,000 μm (preferably 1,000 μm to 5,000 μm), basis weight between 15 g/m² and 200 g/m² (preferably, between 20 g/m² and 80 g/m²), and density between 0.01 g/cc and 0.3 g/cc (preferably between 0.01-0.08 g/cc). Moreover, the bulky nonwoven will have an effective pore diameter between 300 μm to 2000 μm. The effective pore diameter is estimated from web density, fiber diameter and fiber density values following the method of Dunstan & White, J. Colloid Interface Sci, 111 (1986), 60 wherein effective pore diameter=4*(1−solid volume fraction)/(solid volume fraction*solid density*solid specific surface area).

As used herein, "bulkifying" refers to a treatment and/or process that results in a decrease of the bulk density and an increase of the void volume (porosity of the nonwoven web) and specific volume (i.e., the inverse of density) of a nonwoven relative to the bulk density and void volume of the nonwoven prior to "bulkifying". After being subjected to "bulkifying", such a nonwoven is sometimes referred to herein as a "bulkified nonwoven".

As used herein, "BBNW" refers to a nonwoven, optionally a bulky nonwoven, that has been at least partially bulkified.

Any of the nonwovens disclosed herein may form a top sheet or cover layer of the absorbent core composites, a base layer or substrate or back sheet of the absorbent composite, an intermediate layer of the absorbent core composite (positioned between the top sheet and back sheet), or any combination thereof.

As used herein, "nonwoven substrate" refers to any of the nonwovens disclosed herein that supports at least some absorbent material thereon and/or therein.

As used herein, "SAP-free" and "absorbent material-free" refers to surface area on a nonwoven substrate that lacks absorbent material.

As used herein, "absorbent layer" and "absorbent material layer" and "AML" refer to a layer of a core that is composed of at least one absorbent material capable of absorbing and retaining at least some liquid. Any of the absorbent materials disclosed herein may be or include SAP (high or super absorbent polymer), which may be composed of polyvinyl alcohol, polyacrylate, any of various grafted starches, or cross-linked sodium polyacrylate, for example. While described as particles herein, the SAP may be in the form of particles, fibers, foams, web, spheres, agglomerates of regular or irregular shapes, and film. In some aspects, the SAP is combined with an absorbent matrix, which may be a de-fiberized wood pulp or similar material. In other aspects the SAP, and the absorbent core composite as a whole, lacks an absorbent matrix. In some aspects, at least one set of the plurality of SAP particles are mixed with at least one other particle. Such other, non-SAP particles may include, but are not limited to, hot melt adhesive particles, binder particles, spacer particles, or other particles. While "SAP" is used to refer to the absorbent material used in many of the specific embodiments shown and/or described in the present disclosure, it is understood that the "SAP" in any such embodiments may be replaced with another absorbent material. For example, the "SAP-free lanes" disclosed herein may be "absorbent material-free lanes". In some aspects, the absorbent materials used herein are selected based upon the intrinsic superabsorbent properties, including gel bed permeability, absorption speed (vortex), absorbent capacity (CRC), and particle size.

As used herein, "bodyside" or "body side" refers to a surface and/or side that faces the body of a user when the absorbent core composite is worn by a user (e.g., when the absorbent core composite is incorporated into a diaper or other absorbent article that is worn by a user).

As used herein, "upstream" in reference to a process step refers to a step in a process that occurs temporally before another step. For example, in a process where a nonwoven is bulkified and then SAP is applied to the bulkified nonwoven, the bulkfification step would be described as being "upstream" of the SAP application step.

As used herein, "upstream" in reference to fluid flow within an absorbent core composite refers to a spatial and/or temporal position along a flow path of the fluid. For example, if a liquid insult first flows through a bulkified region of a nonwoven layer, and then flows into a SAP-containing lane of an absorbent layer, the bulkified region of the nonwoven layer would be described as being "upstream" of the SAP-containing lane of the absorbent layer, at least with respect to that particular flow path.

Multilayer Core

Certain embodiments of the present disclosure include multilayer absorbent cores that include one or more nonwoven layers and one or more absorbent layers. In some such embodiments, the multilayer absorbent cores include layers of varying: length, width, thickness, basis weight, SAP loading, material composition, density, presence or absence of SAP-free lanes, wettability, capillarity, SAP permeability, SAP absorption rate, SAP absorption capacity, NW void volume, NW capillarity, and/or the presence or absence of slitting. In some embodiments, these same properties may be varied within a single layer. The absolute and relative arrangement of and properties of the layers may be selected to provide desired fluid flow and retention properties. For example, the absolute and relative arrangement of and properties of the layers may be selected such that fluid quickly enters the bodyside of the core and flows into the interior of the core, such that the bodyside of the core is maintained in a relatively dry, comfortable state.

Figure 4:
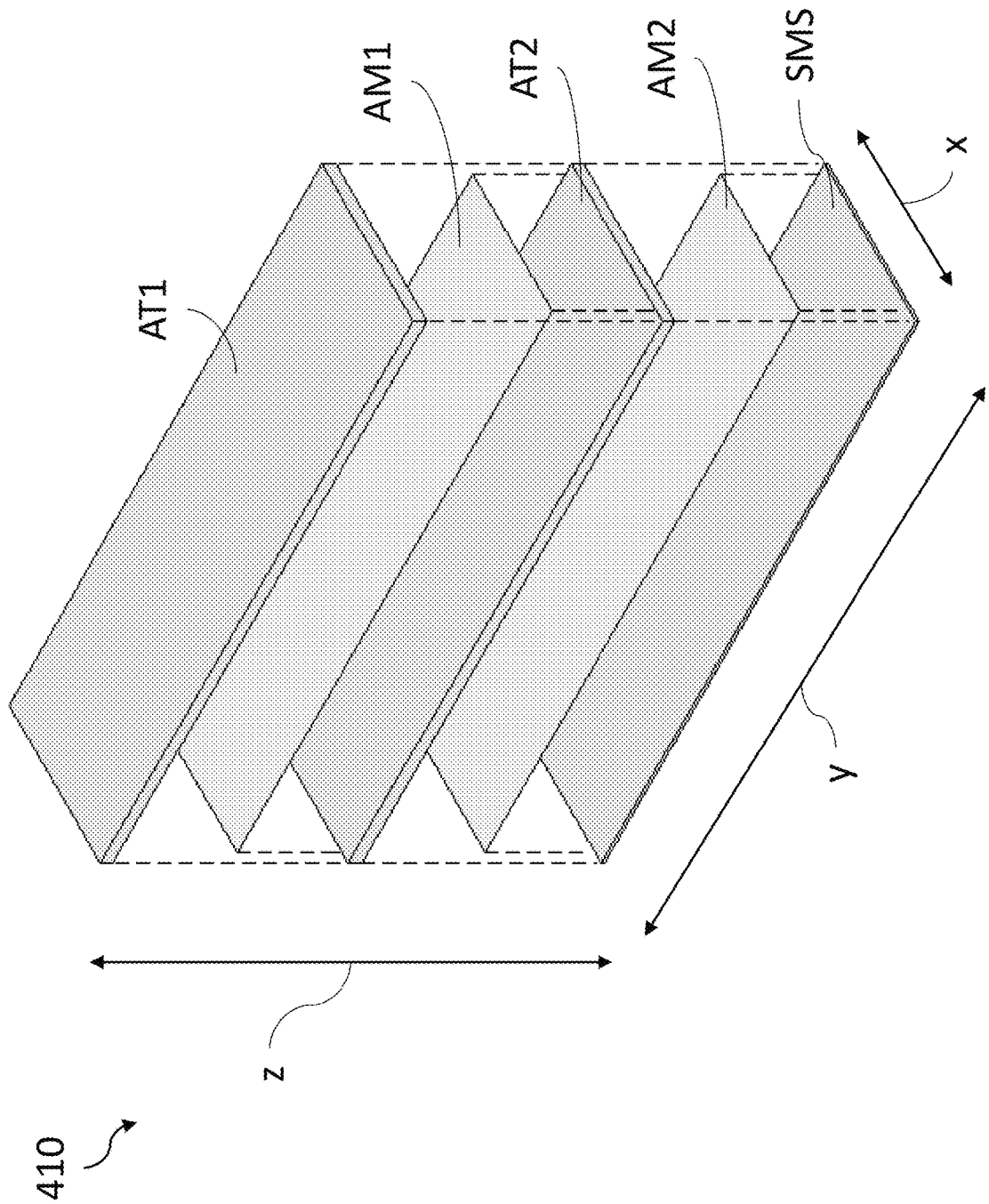
FIG. 4 is a perspective, exploded view of a multilayer absorbent core composite according to the disclosure and suitable for incorporation into a disposable absorbent core composite also according to the disclosure.

The exploded view of FIG. 4 depicts a multi-layer absorbent core composite or construction 410 according to the disclosure and suitable for incorporation into a disposable absorbent core composite also according to the disclosure. Such a composite or construction may be referred to herein by the acronym MLC. As will become evident (to one of ordinary skill in the art), a multi-layer composite or construction, according to the present disclosure, includes at least one fiber network layer (FNL or NW) and at least one absorbent material layer where an absorbent material is disposed. In some applications, an absorbent material layer may include two or more discrete, often spaced-apart, deposits or aggregation of absorbent material situated between two nonwoven or fibrous network layers. The discrete deposits or aggregations may not be necessarily identical. The deposits or aggregates may not necessarily be at the same depth and thickness (in the z-direction) but may be generally found between two distinct layers or components and will generally be found in or about the same approximate depth.

Accordingly, various applications and aspects of the disclosure are defined by the basic construction described above in combination with one or more material or structural features described or illustrated in this disclosure, including this Detail Description, the Summary, the Figures, and the accompanying claims. Thus, this Description, the Summary, the individual Figures or the claims should not be construed as limiting these aspects and applications. Instead, each of these portions of the present disclosure reveal one or more structural or material feature that may be combined or incorporated with the basic construction described above to define a unique aspect or application. Furthermore, the basic construction may be applied to or incorporated with a variety of disposable absorbent articles, each of which being in accordance with an aspect of the disclosure. The same applies to the systems, apparatus, and methods of making the absorbent composite and the disposable absorbent article incorporating the composite. That is systems, apparatus, and methods (including sub-systems and sub-processes applied to making or configuring a component) of making different absorbent composites, as described above, are also revealed herein, and provided in accordance with aspects and applications of the present disclosure.

Returning to the multi-layer composite, MLC, of FIG. 4, two absorbent material (AM) layers utilized, each preferably including or consisting of superabsorbent particles (SAP) (sometimes referred to herein simply as SAP layers or in the Figures, as "SAP"). The two AM layers are bounded and at least partly supported by nonwoven layers, including two air-through layers (AT) and one SMS layer. In FIG. 4, and in the remaining Figures in cross-section (unless indicated otherwise), the top layer (here the top AT layer) is positioned atop the first SAP layer and may be referred to as bodyside, body-facing, or upstream of the other components because it serves to receive, first, any fluid discharge or insult. The first or top SAP layer may feature SAP-free (or absorbent material-free, AM-free, or simply "free lanes") directed in the longitudinal or y direction of the diaper or core plane. This direction coincides with the direction from one waist region or end region to an opposite (positioned) waist or end region. When the article or the core is laid out in the planar condition, i.e., prior to being worn or late in the manufacturing process, this y-direction also describes a plane. It is important to understand, however, that when the article is worn, the article, including such a core surface or plane, is curved to conform to the wearer's body. Thus, the waist regions, and the longitudinal ends or regions of the core are elevated from point of insult, the crotch region of the article, and the central portion of the absorbent core (which are all co-located at or about the low point of the core's curvature). See, e.g., FIGS. 1D-1F, 2 and 3 for reference.

In the construction of FIG. 4, the uppermost body side AM layer underlies the uppermost bodyside NW or AT layer. The body side AT layer acts to assist in the acquisition and distribution of initial fluid intake. A second AT layer is position between the uppermost body side AM layer and a lower AM layer, and a bottom SMS layer is positioned below the lowermost AM layer. In use, the absorbent core 410 concentrates distribution functions and mechanisms upstream to the top layers, or early during fluid insult and receipt. In one aspect, the top and/or bottom AM layers are single, uniform constructions (i.e., with no AM-free lanes). The bottom AM layer receives fluid traveling through upper layers and fluid escaping from SAP filled regions or saturated SAP regions of the uppermost AM layer.

While each AM, AT, and SMS layer in FIG. 4 is shown as a discrete layer, the absorbent core composites or constructions disclosed herein are not limited to such an arrangement, and some layers may at least partially overlap in the z-direction. For example, AM1 may be at least partially or fully embedded within AT1, at least partially or fully embedded within AT2, or at least partially embedded within AT1 and within AT2 (optionally, fully embedded within a combination of AT1 and AT2). When an AM layer is fully embedded within an AT layer (or other nonwoven layer), then the AM and AT layers are full overlapped within the z-direction. AM2 may be at least partially or fully embedded within AT2, at least partially or fully embedded within SMS, or at least partially embedded within AT2 and within SMS (optionally, fully embedded within a combination of AT2 and SMS).

Multilayer Core—Two Concentrated SAP Layers

Similar to the core described with reference to FIG. 4, each AM layer of FIGS. 4A-4S may be at least partially or fully embedded within one or more adjacent nonwoven layers (e.g., NW or BNW).

FIG. 4A is a simplified, cross-sectional view of a multi-layer core composite or construction 410a, including two absorbent core material layers AM1, AM2 and two bulky nonwoven layers, BNW1 and BNW2. In some aspects, AM1 and AM2 are uniform SAP layer constructions without AM-free lanes. In one aspect, each of AM1 and AM2 has a basis weight 150 gsm, and each of BNW1 and BNW2 has a basis weight of 50 gsm. Thus, 150 gsm of SAP is concentrated within two layers of MLC 410a.

Multilayer Core—Three Distributed Layers of SAP

FIG. 4B is a simplified, cross-sectional view of a multi-layer core composite or construction, MLC 410b, having three absorbent core material layers (each may have a loading of 100 gsm) AM1, AM2, and AM3, and having three bulky nonwoven layers BNW1, BNW2, and BNW3 (each may have a loading of 50 gsm). Thus, the total basis weight (and raw material cost) of the components between constructions 410a and 410b are the same, but the SAP is distributed into thinner layers between more bulky nonwoven layers. The BNW layers provide more surface area to distribute fluid in the Y and X directions, and there is more SAP to receive fluid (as opposed to concentrations of SAP that may saturate more quickly); thereby improving the effectiveness and efficiency of the absorbent core.

Multilayer Core—Four Distributed Layers of SAP

FIG. 4C provides a further illustration of the benefits of spreading the same amount of SAP within thinner layers, sandwiched between more BNW layers. Here, MLC 410c employs four AM layers (each which may have a loading of 75 gsm), including AM1, AM2, AM3, and AM4; and four BNW layers (each which may have a loading of 25 gsm), including BNW1, BNW2, BNW3, and BNW4. This arrangement provides the same total basis weight of components as in cores 410a and 410b at the same raw material cost. However, MLC 410c has more BNW surface area, which acts to acquire and distribute liquid more readily than having less BNW surface area. Also, in MLC 410c, the SAP is spread out more, relative to the spread of SAP in MLCs 410a and 410b, allowing the SAP in MLC 410c to more readily receive and absorb fluid intake. Being more spread out, the SAP may present more surface area to fluid insult for more efficient absorption thereof. Also, the additional bulky nonwoven surface area receives, entangles and/or embeds SAP particles more efficiently; thereby, inhibiting migration of such particles more efficiently, such as during manufacturing, packaging and in use (see further discussion of entanglement of SAP within bulky nonwoven in U.S. Pat. No. 9,789,014 and U.S. Patent Publication No 2015/0045756, which are hereby incorporated by reference and made a part of the disclosure, for all purposes).

Thus, in some aspects, the present disclosure relates to methods of distributing a set quantity of SAP and BNW into multiple layers within an absorbent core composite, as opposed to incorporating additional SAP and BNW into the absorbent core composite. Thus, enhanced fluid handling capabilities may be achieved without increasing the basis weight of the core composite, and without increasing the raw material costs associated with forming the core composite.

Multilayer Core—Varying Dimensions

In some aspects, the lengths, widths, heights, or combinations thereof of each layer of the absorbent core composite may be varied. FIG. 4D is a cross-sectional, elevation view of a multi-layer core composite or construction, MLC 410d, including multiple material layers of varying dimensions. In this exemplary configuration, three bulky nonwoven layers BNW1, BNW2, and BNW3 of varying thickness; and three AM layers AM1, AM2, and AM3 of varying thickness are employed. The BNW layers of greater thickness are the top layer (BNW1) and the middle layer (BNW2), with the bottommost BNW layer (BNW3) being the thinnest. Conversely, the topmost AM layer (AM1) is the thinnest of the AM layers in MLC 410d, while the middle (AM2) and bottom most layers (AM3) are thicker and of the same general thickness. Thus, the thicker BNW layers, BNW1 and BNW2, are well positioned to act on fluid intake near the point of insult, including the distributing the fluid in the x and y directions (e.g., via wicking action of the fiber network). See the directional arrows, in FIGS. 4J, 4Q, 4R, and 4S showing initial intake or point or region of initial insult, and showing the distribution of fluid via the fiber network within the cores 410j, 410q, 410r, and 410s. FIG. 4D also illustrates other components commonly incorporated in an absorbent core composite (and an absorbent core or crotch region of a disposable absorbent article) of the type as that of the present disclosure. The article A may include a cover layer CL and base layer BL (not shown) generally encasing the absorbent core composite MLC 410d and forming parts of the absorbent core. Also shown are the topsheet TS and impermeable backsheet BS. An ADL layer atop the absorbent core composite MLC 410d may be included (not shown).

Figure 4F:
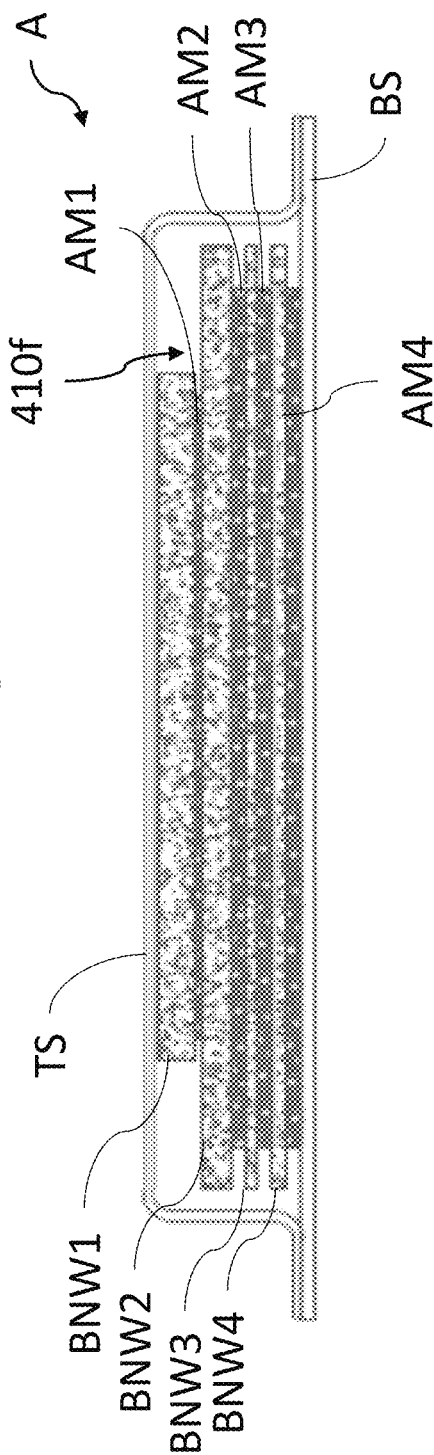
FIG. 4F is a cross-sectional, elevation view of a multilayer core composite or construction, including multiple material layers of varying dimensions, including varying thickness, width and/or depth.

FIGS. 4E and 4F are cross-sectional, elevation views illustrating variations in a multi-layer core composites or constructions MLC 410e and MLC 410f, respectively, according to the disclosure. MLCs 410e and MLC 410f each include multiple material layers of varying dimensions, including varying thickness and depth (height in the z direction). MLC 410e in FIG. 4E contains four BNW layers and four AM layers. The BNW layers gradually decrease in thickness from the top layer to the bottommost layer. Conversely, the AM layers increase in thickness from the topmost layer to the bottommost layer. The thicker BNW layer, BNW1, serving as the top layer presents a softer surface to the user, while also utilizing and maximizing the ADL capabilities of the BNW. The BNW layers are wider than the AM layers in the x-direction. Thus, the gradient thickness of the BNW layers of MLC 410e is inverse to the gradient thickness of the AM layers of MLC 410e. MLC 410f of FIG. 4F features a topmost BNW layer, BNW1, and AM layer, AM1, of a reduced width (and length) relative to the lower BNW layers. Positioned centrally in the crotch region of the disposable absorbent article A, the top two layers serve as the initial receipt or target zone for fluid intake. The reduced dimensions reduce raw material usage, while presenting a more conforming profile for the wearer and increasing flexibility (about the longitudinal direction) due to material reduction along the lateral margins.

Multilayer Core with Vertically Aligned SAP-Free Lanes

Figure 4G:
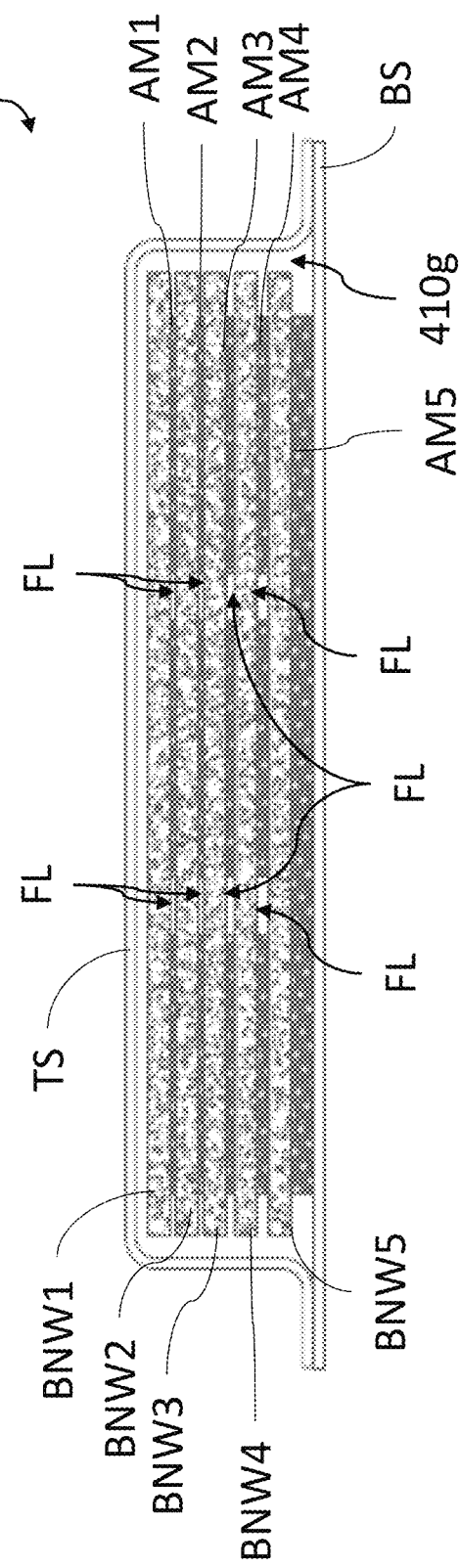
FIG. 4G is a cross-sectional, elevation view of a multi-layer core composite or construction, including multiple material layers of varying dimensions, including varying thickness, width and/or depth, and including absorbent material layers featuring absorbent material-free zones or lanes.

FIG. 4G is a cross-sectional, elevation view of a multi-layer core composite or construction, MLC 410g, including multiple material layers of varying dimensions, including thickness, width and depth. MLC 410g includes five absorbent material layers, with the top four AM layers, AM1-AM4, equipped with absorbent material-free zones or lanes, FL, (in the MD). As discussed previously, in respect to FIG. 4, the free lanes are located close to the center and a central AM layer or deposit. The free lanes facilitate transport of fluid intake along the y-direction, where the larger extent of absorbent material is located. The free lanes also facilitate transport of fluid to lower levels of MLC 410g (and to absorbent material) in the absorbent core composite 410g. FL are also positioned on the margins. With the free lanes vertically aligned, fluid can easily and quickly flow from the bodyside, at or near TS, towards the backside, BS, by flowing from one FL, through the adjacent BNW layer, and into the downstream FL there-below.

Multilayer Core with Staggered SAP-Free Lanes

The multi-layer core composite or construction, MLC 410h, of FIG. 4H is similar to that of FIG. 4G. However, the AM-free lanes, FL, are not vertically aligned between the various layers of MLC 410h. Rather, with each successive AM-layer further down in MLC 410h, with the exception of the bottommost AM layer, the free lanes are positioned more laterally outward. Positioning the free lanes in this way corresponds with the further distribution of fluid intake outward with each successive downstream layer in the composite 410h.

FIG. 4I is a cross-sectional, elevation view of a multi-layer core composite or construction 410i, including multiple material layers of varying dimensions, including thickness, width and depth, including absorbent material layers featuring absorbent material-free zones or lanes FL. The composite 410i of FIG. 4I employs several of the features in previous multi-layer core constructions, including staggered AM-free lanes, FL.

Multilayer Core—Directing Fluid Flow

Figure 4J:
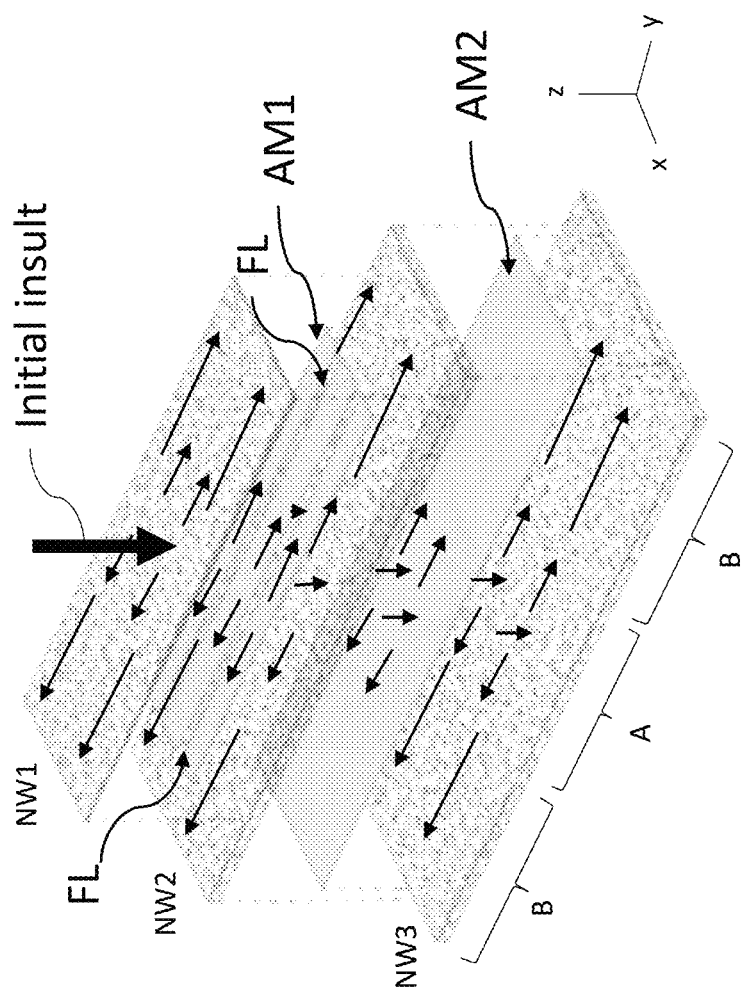
FIG. 4J is a perspective, exploded view of a multi-layer absorbent core composite or construction, including an absorbent material layer having absorbent material-free lanes in the machine direction.

FIG. 4J is a perspective, exploded view of a multi-layer absorbent core composite or construction, MLC 410j, including an absorbent material layer having absorbent material-free lanes in the machine direction, according to the disclosure. The fiber network layers in this exemplar composite, MLC 410j, are provided by bulky non-woven, with a top BNW (NW1), an intermediate layer (NW2), and a base layer (NW3). AM1 layer, including SAP-free lanes FL, has a reduced length relative to the NW layers and to AM2. AM1 is positioned in the central or target region of the absorbent article, and is supported on, within, and/or between NW1 and NW2. The arrows in FIG. 4J show the X-Y directional spreading of fluid flow MLC 410$j$, including in the SAP layers, AM1 and AM2. Such fluid flow directionality is at least partially controlled by the SAP permeability and absorbency rates, which are typically arranged to be slower than corresponding fluid flows in the NW layers and SAP-free lanes. In some aspects, all nonwoven layers within the area indicated as "B" of MLC 410$j$ in FIG. 4J are designed to be higher capillarity regions relative to the portions of the nonwoven layers within the area of MLC 410$b$ indicated as "A" to support fluid wicking when in use.

When in use, the absorbent core composite may have a U-shaped configuration. In some aspects, the absorbent core composite layers are arranged and configured such that high permeability and/or slower absorbency rate SAP is positioned within the uppermost, bodyside top layer; and faster SAP is positioned within higher-capacity lower, bottom layers. As such, when worn by a user, the lower capillarity region A is positioned at the crotch region, and is lower on the body relative to the higher capillarity regions B, which are positioned higher on the waist of the user. As such, the higher capillarity of regions B promotes wicking via capillary action of fluids from the region A to the regions B, even in opposition gravitational forces. The flow patterns shown by the arrows in FIG. 4J account for flow in the product longitudinal direction (y-direction) and refers to the embodiments having a capillarity gradient (higher capillarity towards the ends of the absorbent product) to support wicking of the fluid against gravity (required due to the in-use product configuration that is U-shaped). The arrows show that fluid spreading in the SAP layers is typically slower than fluid spreading in NW and SAP-free lanes.

Multilayer Core—Variations in Basis Weight

With further reference to FIGS. 4D-4I each article A includes topsheet TS and backsheet BS. Topsheet TS may be a hydrophilic, water-permeable layer (e.g., a spunbound nonwoven), and may have a basis weight of 15 g/m$^2$, or from 5 to 20 g/m$^2$. Such a topsheet may be used with any of the embodiments of absorbent core composites disclosed herein. Backsheet BS may be a water-permeable layer (e.g., a polyethylene film or multilayer laminate of nonwoven and polyethylene film). Such a backsheet may be used with any of the embodiments of absorbent core composites disclosed herein. The basis weight of each nonwoven layer and loading (basis weight) of each absorbent layer may be varied, with the layers and basis weights thereof selected and arranged to provide for desired fluid intake, distribution, and absorption properties (collectively "fluid handling properties"). For example, in some embodiments, the basis weight of the nonwovens decreases, on average, moving downward into the core in the z-direction, and the basis weight (loading) of the absorbent material increases moving downward into the core in the z-direction. Referring to FIGS. 4D-4I, various exemplary arrangements of nonwoven and absorbent layers with selected basis weights will now be described.

MLC 410$d$ of FIG. 4D is encased within topsheet TS and backsheet BS, and includes: uppermost BNW1 layer that is an air-through nonwoven having a basis weight that may range from 30 to 60 g/m$^2$; intermediate BNW2 layer that is an air-through nonwoven having a basis weight that may range from 30 to 80 g/m$^2$; and lowermost BNW3 layer is an air-through nonwoven having a basis weight that may range from 20 to 50 g/m$^2$. MLC 410$d$ also includes: AM1 layer that is sandwiched between BNW1 and BNW2, and has a basis weight of from 50 to 150 g/m$^2$; AM2 layer that is sandwiched between BNW2 and BNW3, and has a basis weight of from 75 to 200 g/m$^2$; and AM3 layer that is below BNW3, and has a basis weight of from 75 to 200 g/m$^2$. Each of AM layer may include or consist of SAP. As is evident from FIG. 4D, the nonwoven layers, BNW1, BNW2, and BNW3 are wider in the x-direction than the width of the absorbent material layers, AM1, AM2, and AM3.

FIG. 4E depicts article A having topsheet TS and backsheet BS, with absorbent core composite, MLC 410$e$, encased therein. MLC 410$e$ includes: uppermost BNW1 layer that is an air-through nonwoven having a basis weight that may range from 30 to 60 g/m$^2$; first intermediate BNW2 layer that is an air-through nonwoven having a basis weight that may range from 30 to 50 g/m$^2$; second intermediate BNW3 layer that is an carded nonwoven having a basis weight that may range from 20 to 40 g/m2; and lowermost BNW4 layer is an carded nonwoven having a basis weight that may range from 20 to 40 g/m$^2$. MLC 410$e$ also includes: AM1 layer that is sandwiched between BNW1 and BNW2, and has a basis weight of from 30 to 100 g/m$^2$; AM2 layer that is sandwiched between BNW2 and BNW3, and has a basis weight of from 50 to 150 g/m$^2$; AM3 layer that is sandwiched between BNW3 and BNW4, and has a basis weight of from 50 to 150 g/m2; and AM4 layer that is below BNW4, and has a basis weight of from 75 to 200 g/m$^2$. Each AM layer may include or consist of SAP. As is evident from FIG. 4E, the nonwoven layers, BNW1, BNW2, and BNW3 are wider in the x-direction than the width of the absorbent material layers, AM1, AM2, and AM3. Also, the thickness of the nonwoven layers exhibit a gradience, such that the thickness decreases from proximate TS towards BS; whereas, the thickness of the absorbent layers exhibit a gradience, such that the thickness increase from proximate TS towards BS (i.e., the thickness gradients are of the nonwoven and absorbent material layers are inverse).

FIG. 4F depicts an article A having topsheet TS and backsheet BS, with absorbent core composite, MLC 410$f$ encased therein. MLC 410$f$ includes: uppermost BNW1 layer that is an air-through nonwoven having a basis weight that may range from 30 to 60 g/m$^2$ and a narrowed width relative to the other layers of 80 mm; first intermediate BNW2 layer that is an air-through nonwoven having a basis weight that may range from 30 to 50 g/m$^2$ and a width of 105 mm; a second intermediate BNW3 layer that is an air-through nonwoven having a basis weight that may range from 20 to 40 g/m$^2$ and a width of 105 mm; and lowermost BNW4 layer is an airthrough nonwoven having a basis weight that may range from 20 to 40 g/m$^2$ and a width of 105 mm. MLC 410$f$ also includes: AM1 layer that is sandwiched between BNW1 and BNW2, and has a basis weight of from 30 to 100 g/m$^2$; AM2 layer that is sandwiched between BNW2 and BNW3, and has a basis weight of from 50 to 150 g/m$^2$; AM3 layer that is sandwiched between BNW3 and BNW4, and has a basis weight of from 50 to 150 g/m2; and AM4 layer that is below BNW4, and has a basis weight of from 50 to 100 g/m$^2$. The uppermost nonwoven layer, BNW1, is narrower than the remaining nonwoven layers, and the uppermost absorbent material layer, AM1, is narrower than the remaining absorbent material layers. Each AM layer may include or consist of SAP.

FIG. 4G depicts article A having topsheet TS and backsheet BS, with absorbent core composite, MLC 410$g$ encased therein. MLC 410$g$ includes: uppermost BNW1 layer that is an air-through nonwoven having a basis weight that may range from 20 to 50 g/m$^2$; first intermediate BNW2 layer that is an air-through nonwoven having a basis weight that may range from 20 to 50 g/m²; second intermediate BNW3 layer that is an air-through nonwoven having a basis weight that may range from 20 to 50 g/m2; third intermediate BNW4 layer is an air-through nonwoven having a basis weight that may range from 20 to 50 g/m²; and a lowermost BNW5 that is an airlaid nonwoven having a basis weight of 30 to 80 g/m². MLC 410g also includes: AM1 layer that is sandwiched between BNW1 and BNW2, and has a basis weight of from 30 to 100 g/m²; AM2 layer that is sandwiched between BNW2 and BNW3, and has a basis weight of from 30 to 100 g/m²; AM3 layer that is sandwiched between BNW3 and BNW4, and has a basis weight of from 50 to 150 g/m²; AM4 layer that is sandwiched between BNW4 and BNW5, and has a basis weight of from 50 to 150 g/m²; and AM5 layer that is below BNW5, and has a basis weight of from 50 to 150 g/m². Each AM layer may include or consist of SAP. The nonwoven layers of MLC 410g each have the same or substantially the same thickness, while the AM layers exhibit a gradient thickness, such that the AM layers are thicker toward BS.

FIG. 4H depicts article A having topsheet TS and backsheet BS, with absorbent core composite, MLC 410h encased therein. MLC 410h includes: uppermost BNW1 layer that is an air-through nonwoven having a basis weight that may range from 20 to 50 g/m²; first intermediate BNW2 layer that is an air-through nonwoven having a basis weight that may range from 20 to 50 g/m²; second intermediate BNW3 layer that is an air-through nonwoven having a basis weight that may range from 20 to 50 g/m²; third intermediate BNW4 layer is an air-through nonwoven having a basis weight that may range from 20 to 50 g/m²; and a lowermost BNW5 that is an air-through nonwoven having a basis weight of 20 to 50 g/m². MLC 410h also includes: AM1 layer that is sandwiched between BNW1 and BNW2, and has a basis weight of from 30 to 100 g/m²; AM2 layer that is sandwiched between BNW2 and BNW3, and has a basis weight of from 30 to 100 g/m²; AM3 layer that is sandwiched between BNW3 and BNW4, and has a basis weight of from 50 to 150 g/m²; AM4 layer that is sandwiched between BNW4 and BNW5, and has a basis weight of from 50 to 150 g/m²; and AM5 layer that is below BNW5, and has a basis weight of from 50 to 150 g/m². Each AM layer may include or consist of SAP. The nonwoven layers of MLC 410g each have the same or substantially the same thickness, while the AM layers exhibit a gradient thickness, such that the AM layers are thicker toward BS.

FIG. 4I depicts article A having topsheet TS and backsheet BS, with absorbent core composite, MLC 410i encased therein. MLC 410i includes: uppermost BNW1 layer that is an air-through nonwoven having a basis weight that may range from 20 to 50 g/m² and a narrowed width of 70 mm (with the remainder of the BNWs having widths of 95 mm); a first intermediate BNW2 layer that is an air-through nonwoven having a basis weight that may range from 20 to 50 g/m²; second intermediate BNW3 layer that is an air-through nonwoven having a basis weight that may range from 20 to 50 g/m²; third intermediate BNW4 layer is an air-through nonwoven having a basis weight that may range from 20 to 50 g/m²; and a lowermost BNW5 that is an air-through nonwoven having a basis weight of 20 to 50 g/m². MLC 410i also includes: AM1 layer that is sandwiched between BNW1 and BNW2, and has a basis weight of from 30 to 100 g/m²; AM2 layer that is sandwiched between BNW2 and BNW3, and has a basis weight of from 30 to 100 g/m²; AM3 layer that is sandwiched between BNW3 and BNW4, and has a basis weight of from 50 to 150 g/m²; AM4 layer that is sandwiched between BNW4 and BNW5, and has a basis weight of from 50 to 150 g/m²; and AM5 layer that is below BNW5, and has a basis weight of from 50 to 150 g/m².

In FIGS. 4 and 4A-4I (as well as any other core composite disclosed herein), the absorbent material within each of AM layer may be composed of the same or a different polymer (e.g., SAP), imparting the same or different, configurable, layerable fluid handling characteristics to each layer. Also, AM-free lanes (FL) may be provided in any of the AM layers of the composites disclosed herein. Furthermore, the positioning of AM-free lanes, if any, may be aligned to encourage fluid flow towards selected regions of the core, such as towards the lower and outer regions of the core. In FIGS. 4H and 4I, the AM-free lanes, FL, are arranged with less overlap between AM-free lanes in adjacent layers; thereby, encouraging fluid flow to the side margins of the core and to the lower regions of the core. While FIGS. 4 and 4A-4I do not show adhesive, adhesive may be used to adhere the nonwoven layers together and/or to adhere absorbent material to the nonwoven layers.

In some embodiments, the nonwoven layers disclosed herein have a basis weight ranging from 20 to 80 g/m², or from 30 to 60 g/m², or from 30 to 80 g/m², or from 20 to 50 g/m², or from 20 to 40 g/m², or from 30 to 50 g/m². In some embodiments, the absorbent material layers disclosed herein have a basis weight of from 30 to 200 g/m², or from 50 to 150 g/m², or from 75 to 200 g/m², or from 30 to 100 g/m².

In one particular embodiment, the absorbent core composite includes three nonwoven layers, including an uppermost bulky nonwoven layer having a basis weight of 75 g/m², a lowermost airlaid nonwoven layer having a basis weight of 150 g/m², and a single intermediate bulky nonwoven layer having a basis weight of 30 g/m². The uppermost and intermediate bulky nonwoven layers may be composed of the same or substantially the same material, but with a different loading (e.g., having a different thickness). In this particular embodiment, the absorbent core composite includes two absorbent material layers, including an uppermost absorbent material layer sandwiched between the uppermost bulky nonwoven layer and the intermediate bulky nonwoven layer (optionally embedded in one or both of these nonwoven layers); and a lowermost absorbent material layer sandwiched between the lowermost airlaid nonwoven layer and the intermediate bulky nonwoven layer (optionally embedded in one or both of these nonwoven layers). Each of the two absorbent material layers may have a loading of 150 g/m², and may include or consist of SAP. Applicants have found that nonwovens having relatively high basis weight at the bodyside of the core composite encourage fluid intake and distribution into the lower portions of the core; thereby, promoting dryness on the bodyside of the core.

Multilayer Core—Directing Fluid Flow

FIGS. 4K-4M illustrate fluid flow direction and pathways within or through composites 410k, 410l, and 410m. Fluid is distributed increasingly towards the margins and the bottom of the core, with AM-free lanes encouraging and directing fluid flow within the core, as shown.

General Core Construction Formulary

To achieve certain desired or enhanced fluid or waste handling (flow and retention) capabilities in many of the core constructions described herein, attention may be directed to the selection and then strategic placement of the absorbent material, including the use of additives to impact target properties (see, e.g., FIGS. 18E and 18F), and/or the fibrous network or nonwoven. In this respect, intrinsic superabsorbent properties of interest include gel bed permeability, absorption speed (vortex), absorbent capacity (CRC), particle size, particle packing density, stiffness, among other properties. Furthermore, intrinsic fiber network layer (nonwoven) properties of interest include density (i.e., void volume (=1/density)), permeability, and capillarity (pore size and fiber wettability).

As for material placement in the core composite, certain general principles may apply in the more common applications. Generally, SAP positioned in the path of insult of fluid flow in the z-direction (thickness) has the following properties: (1) gradient permeability, with the highest permeability at or near the top of the core and with the permeability reducing to the lowest at or near the bottom of the core; (2) gradient absorption rate, with slower absorbing SAP positioned at or near the top of the core and progressively faster SAP placed at or near the bottom of the core; and (3) gradient absorption capacity, with higher absorbent capacity SAP positioned at or near the bottom of the core for maximum absorbent efficiency, and lower absorbent capacity SAP positioned at or near the top of the core.

Fiber network layers (e.g., nonwoven layers) in the path of insult of flow fluid in the z-direction (thickness) generally exhibit a gradient void volume, with higher void volume nonwovens at or near the top of the core for handling the initial fluid insult gush and distributing the fluid within the NW layer, and with lower void volume nonwovens at or near the bottom of the core. Also, the cores may exhibit a profiled or gradient capillarity within the fiber network layers in the x-y plane, such that higher capillarity (relative to the fluid target area) is constructed towards the ends of the absorbent core. Such a capillarity profiled construction allows the fluid to continually spread towards the ends of the core for full utilization.

Variations in capillarity between layers and within a layer may be achieved by selective densification, wettability enhancement by plasma or corona treatment (of regions in the X-Y plane), bulkification, or by selective arrangement of existing bulky and less bulky layers. Fiber network layers in the z-direction may be selected and designed so as to exhibit and present higher capillarity layers towards the bottom (downstream), and lower capillarity layers towards the bodyside. Such a gradient in capillarity encourages and/or facilitates wicking of fluid flow downstream, toward the bottom AM layer, and promotes fluid spreading against gravity (i.e., when the article is worn and is positioned in a U-shape); thereby, increasing absorbent material and core utilization during product use. It should be noted that more absorbent material and absorbent surfaces are found in the y-direction and that during wear, the absorbent article is curved generally upward toward the waist regions or longitudinal ends of the article. And thus, fluid travel toward the waist regions may be resisted by gravity as well.

System for Forming Multilayer Cores

Figure 5:
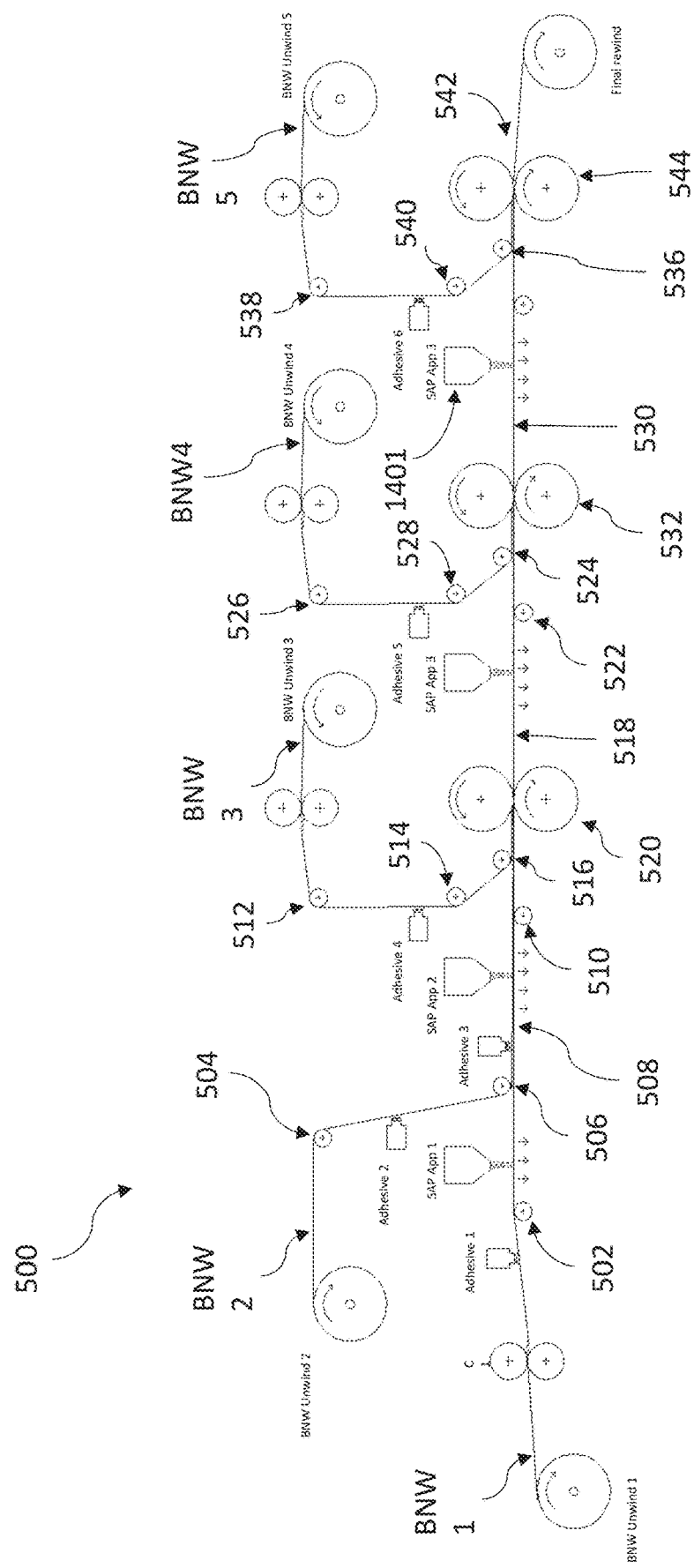
FIG. 5 is a schematic of a system and process for making an absorbent core composite or construction, according to the disclosure.

FIG. 5 is a schematic of a system and process for making an absorbent core composite or construction, according to the disclosure. In FIG. 5: "BNW unwind" refers to a machine roller or spool from which a BNW fabric web is unwound for combining with other elements to form the absorbent core composite; "C1" refers to a compressing apparatus, such as a pair of opposing machine rollers that apply a compressive force to fabrics passing therethrough; "Adhesive" refers to an applicator that applies adhesive to the layer of fabric and/or absorbent material passing thereunder; "SAP App" refers to an applicator that applies SAP to the layer of fabric and/or absorbent material passing thereunder; and "final rewind" refers to a collection spool upon which the formed absorbent core composite is collected after production.

System 500 includes BNW unwind 1, from which BNW1 is unwound, and passes through C1 for compression thereof. From C1, BNW1 passes under Adhesive 1, where an adhesive is applied to BNW1. From Adhesive 1, BNW1 passes over roller 502, and then SAP is applied thereto from SAP App 1. In some embodiments, at least some of the SAP filters through BNW1.

System 500 includes BNW unwind 2, from which BNW2 is unwound, and passes over roller 504 and under Adhesive 2, where an adhesive is applied to BNW2. From Adhesive 2, BNW2 passes over roller 506. Also, from SAP App 1, BNW1 passes over roller 506, such that BNW1 and BNW2 are laminated together at or after roller 506, forming laminate 508.

From roller 506, laminate 508 passes under SAP App 2, where SAP is applied thereto. In some embodiments, at least some of the SAP filters through laminate 508. From SAP App 2, laminate 508 passed over roller 510.

System 500 includes BNW unwind 3, from which BNW3 is unwound, and passes through C1 for compression thereof. From C1, BNW3 passes over roller 512 and under Adhesive 4, where an adhesive is applied to BNW3. From Adhesive 4, BNW3 passes over roller 514, and over roller 516. Laminate 508 also passes over roller 516, such that BNW3 and laminate 508 are laminated together at or after roller 516, forming laminate 518.

Laminate 518 then passes through rollers 520 and under SAP App 3, where SAP is applied thereto, and where some of the SAP may filter therethrough. Laminate 518 then passes over roller 522 and roller 524.

System 500 includes BNW unwind 4, from which BNW4 is unwound, and passes through C1 for compression thereof. From C1, BNW4 passes over roller 526 and under Adhesive 5, where an adhesive is applied to BNW3. From Adhesive 5, BNW4 passes over roller 528, and over roller 524. BNW4 and laminate 518 are laminated together at or after roller 524, forming laminate 530.

Laminate 530 passes through rollers 532 and under SAP App 4, where SAP is applied thereto, and where some of the SAP may filter therethrough. Laminate 530 then passes over roller 534 and roller 536.

System 500 includes BNW unwind 5, from which BNW5 is unwound, and passes through C1 for compression thereof. From C1, BNW5 passes over roller 538 and under Adhesive 6, where an adhesive is applied to BNW5. From Adhesive 6, BNW5 passes over roller 540, and over roller 536. BNW5 and laminate 530 are laminated together at or after roller 536, forming laminate 542.

Laminate 542 passes through rollers 544 and to final rewind for collection thereof.

Of course, the system shown in FIG. 5 is for exemplary purposes only. Other system configurations and arrangements may be used to form any number core composite configurations in accordance with the present disclosure.

SAP-Free Lanes—Machine and/or Cross Direction

In some embodiments, one or more of the absorbent material layers include absorbent material free lanes (e.g., SAP-free lanes). While referred to as "lanes", such SAP-free areas may be of any number of shapes and arrangements, and may extend in the MD, CD, or any other direction or pattern. While referred to as "SAP-free", such lanes or areas may be free of any absorbent material, or at least free of SAP. In some aspects, the number of MD SAP-free lanes in the uppermost AM-layer is greater than the number of MD SAP-free lanes in the lower and/or lowermost AM-layer(s). In certain aspects, only the uppermost AM layer has MD SAP-free lanes. In certain aspects, only the uppermost AM layer has any SAP-free lanes. The incorporation of SAP-free lanes into an absorbent core composite improves the softness (increases compressibility) for users, increases the fluid intake rate, reduces run-off and overflow of fluid from the AM layer, and directs and distributes the fluid flow within the core.

With reference to FIG. 6A, a multi-layer absorbent core composite 610a is depicted having multiple absorbent core material layers, including a top SAP layer, AM1, with SAP-free lanes directed in the MD. The composite 610a also employs an air-through bulky non-woven as a top layer and an intermediate layer. An SMS nonwoven layer provides a base layer. While not being bound by theory, it is believed that having two or more SAP-free lanes, FL, in the MD enhances fluid distribution more than having a single SAP-free lane in the MD. In some aspects, as shown, only the upper AM layer (AM1) has SAP-free lanes, and the lower AM layer (AM2) has no SAP-free lanes, which may enhance fluid retention in the lower AM layer. In certain aspects, SAP-free lanes may be provided along the margins and/or edges of the AM layers to allow for sealing (adhering the AT layers above and below the AM layer).

In the construction of FIG. 6A, three contiguous deposits of SAP are spaced-apart to form two SAP-free lanes, FL. The lanes are elongated spaces or voids that are bounded by the depth profile of adjacent SAP-containing lanes. The term "lanes" are aptly used here, because such elongated voids (and even the elevated SAP deposit in some respect) resemble lanes in the machine direction on a conveyor during manufacturing. SAP-"free" may be used to refer to that portion of the substrate whereon the SAP are clearly not deposited but is bounded by elongated regions whereon absorbent material is contiguously deposited. It should be further noted that substrate upon which the SAP (and SAP-free lanes) are presented is typically the underlying NW or AT layer. The middle SAP deposit of AM1, SAP2, is of a width greater than that of the two outside SAP deposits (SAP1 and SAP3), primarily because the middle SAP deposit (SAP2) will probably be positioned coincident with the point of insult or initial receipt area (the target zone). The middle SAP deposit, SAP2, is sufficiently wide (or the SAP-free lane sufficiently narrow) so as to substantially accommodate the fluid intake. The SAP-free lanes, FL, are positioned close enough to this central target zone to receive significant fluid intake and assist the distribution of the receipt along the z-direction (against gravity) and toward and along more of the SAP which may not receive, at least initially, its share of fluid intake. Of course, the AT layer also acts to and assists in the acquisition and distribution of initial intake. The SAP-free lanes, FL, may also preferably be aligned with embossing or bonding lines and patterns to promote NW to NW bonding (without interfering with or interference from SAP). In FIG. 6A, the outside SAP lanes, SAP1 and SAP3, are also made at least about ⅓rd or ¼ narrower than the middle SAP deposit, SAP2, to provide SAP-free areas near the lateral margins. This aids in sealing and maintaining the side margins, such as during manufacturing and thereafter, in packaging and use. It is also believed that SAP-free lanes near the top layer enhances the softness and flexibility of the absorbent core. Noting that the absorbent core is curved slightly laterally, as well as upwardly, while worn, the SAP-free lanes near the top improve flexibility about longitudinal axes directed through the SAP-free lanes, for example. Many of the benefits to having SAP-free lanes in the top SAP layer are at least partially diminished in respect to the bottom SAP layer. In use, the core may concentrate distribution functions and mechanisms upstream to the top layers, or early in the points of insult and receipt. Thus, in one aspect, a bottom SAP layer may be provided of a single, uniform construction (i.e., no free lanes). This SAP layer receives fluid traveling through upper layers, including fluid traveling downward from the upper SAP-free lanes, and fluid escaping from SAP filled regions or saturated SAP regions.

In the embodiment illustrated in FIG. 6B, the multi-layer composite 610b employs a SAP layer with free lanes in the CD. AM1 includes multiple SAP-free lanes, FL. The SAP-free lanes and the SAP deposits or aggregates therebetween may be uniformly spaced and of the same width throughout the series of free lanes or SAP lanes. To deposit SAP in the CD, a screen or wire, or a vacuum drum, or SAP printing may be used.

In some aspects, MD and CD free lanes are combined within a single core composite and/or within a single AM layer to form patterns (e.g., grid patterns) of SAP and SAP-free areas, including complex patterns. FIGS. 7A-7G illustrate different configurations of AM-layers featuring AM-free lanes. Some constructions feature only free lanes in the CD (FIGS. 7B, 7F), while others are equipped with free lanes in the MD only (FIGS. 7C, 7D). Other constructions feature a combination of both CD and MD free lanes (FIGS. 7A, 7E). The configuration illustrated in FIG. 7G makes use of free lanes directed at an angle (neither longitudinally directed nor laterally directed). These variations also illustrate that the AM deposits or aggregates that share the AM layer with the free lanes are of different widths, length (and depth), and shapes as dictated by the free lanes that bound them. The corresponding use of SAP lanes also facilitates configuring a core composite, SAP layer and absorbent surface with varying properties (as a function of location and depth). Each absorbent material lane or aggregate, or regions of SAP, may be composed of absorbent material or blend of materials exhibiting target properties and improving certain fluid performance. For example, SAP of higher absorbency or with certain additive, or of higher raw material cost, may be concentrated in or limited to SAP lanes in the central portion of the core composite.

In each of the AM layer configurations, there is provided sufficient absorbent material situated in the region corresponding to the target zone or point insult. This ensures ready receipt and absorption of fluid intake. The CD free lanes in FIG. 7B also improves the flexibility of the core composite about longitudinal axes. In further embodiments, additional SAP aggregates or SAP lanes may be added near the lateral margins to cap the CD lanes, and may prevent a straight-line path to the side margins. Such a multi-layer core construction may be particularly adapted for use in some feminine napkin products and the like.

The configurations of FIGS. 7A and 7E make use of CD and MD free lanes to create a grid of free lanes. These grid configurations take advantage of the operational and structural benefits to using both types of structures, especially as an AM layer near the top of the composite. These include wider fluid distribution, greater flexibility and improved user comfort. The provision of multiple AM aggregates, especially in the case of FIG. 7E, where the aggregates are of varying shape and sizes, allows for the design of an absorbent surface with properties that vary across the expanse of the layer. Absorbent material with or without additives may be selected and concentrated in aggregates occupying specific target regions of the AM layer (and composite).

FIG. 7E also features MD free lanes provided with absorbent material at the end regions, at which the free lanes terminate. The aggregates of absorbent material deposited thereon act as fluid barriers to fluid movement along the free lanes; thereby, mitigating the risk of leakage. These strategically located aggregates also provide an absorbent material destination for such fluid movement in the free lanes. Depending on the absorbent article product and its purpose, these aggregates at the end regions may be sized differently and have a different constituency than other aggregate.

The grid or pattern of absorbent material aggregates shown in FIG. 7G is not restricted to use of CD and MD free lanes. In certain variations, the free lanes or free regions are linear pathways and thus resemble lanes, especially in the manufacturing process. An objective of the grid pattern in FIG. 7G is to efficiently and effectively distribute fluid intake to the absorbent materiel (preferably, not in serial fashion). In this design, the pathways cover more area. The pathway along the y-direction is provided by two main free lanes, which are wider and longer than other free lanes. Additional arteries of SAP-free lanes are provided to extend fluid movement to other areas of absorbent material without the need of turns in the free lanes. The result is more comprehensive coverage, i.e., more fluid is directed straight to more absorbent material utilizing momentum in the fluid intake (e.g., not relying as much on capillary action or flows). As well, the absorbent aggregates remain as a contiguous deposit, where fluid has, in most regions, a continuous two- and three-dimensional pathway and access to neighboring, preferably unsaturated, absorbent material (e.g., SAP particle to SAP particle). The grid configuration of FIG. 7G and other configurations lend themselves to SAP printing techniques. Such techniques will also allow for more constituency control and well as specific and accurate placement of absorbent material deposits and patterns. The grid may be formed as well by use of a movable obstruction, suction aid, specific target placement, and the like.

In some aspects, SAP is applied onto nonwoven layers using a particle scattering method, such as a gravure roll, a needle roll, or by feeding the SAP onto a declined vibratory channel. MD lanes of SAP may be formed by closing off sections of the SAP scattering means, such that the SAP scatter apparatus is not fully open across an entirety of the potential application area on the nonwoven. Closing off sections of the SAP scatter apparatus may be permanent and/or fixed. In some aspects, the SAP scatter apparatus is selectively openable and closable, such as via an aperture that opens and closes. Opening and closing of the SAP scatter apparatus allows the length of the MD SAP lane to be non-continuous and intermittent.

CD SAP-free lanes may be formed by intermittently turning the SAP applicator on and off. When the SAP applicator is on, a CD SAP-containing lane is formed from side to side of the nonwoven substrate material. When the SAP applicator is off, a CD SAP-free lane is formed from side to side of the nonwoven substrate material. In some aspects, CD SAP-free lanes are formed via the opening and closing of an aperture, wherein the closure is across the entire width or a substantial part of the width of the SAP applicator.

In some aspects, SAP may be applied continuously to a patterned shell under vacuum (e.g., onto a nonwoven substrate positioned above the patterned shell). Sections of the patterned shell may be not under vacuum, or the vacuum suction may blocked or interrupted in such sections such that SAP does not stick to the patterned shell (or nonwoven thereon) at such sections. While some fine particles of SAP may be lost in the vacuum, the application method may provide a well-defined SAP pattern.

SAP-Free Lanes—Selectively Arranged in the Upper Layers to Channel Fluid

In some aspects, at least one absorbent material layer of the absorbent core composites disclosed herein include includes SAP-free lanes and at least another absorbent material layer of the absorbent core composite does not include SAP-free lanes. In some aspects, it is advantageous to include SAP-free lanes in the uppermost, bodyside absorbent material layer, and to include no SAP-free lanes in the lowermost absorbent material layer of the absorbent core composite. Such an arrangement of SAP and SAP-free lanes may facilitate fast fluid absorption of the absorbent core composite by fluid channeling the flow of fluid from the upper layers of the core to the lower layers of the core.

SAP-Free Lanes—Variations Between Lanes

In some aspects, the SAP-containing lanes may vary in at least one respect. For example, the SAP-containing lanes may vary in: the size of SAP particles contained therein; the type and/or composition of the SAP particles contained therein; the concentration of SAP particles contained therein (e.g., amount of SAP per unit surface area of nonwoven substrate); the addition or lack thereof of non-SAP particles; the width, length, and/or height of the SAP-containing lane (in the x-, y-, and z-directions); and the type and/or state of the nonwoven substrate supporting the SAP in the SAP-containing lane (e.g., NW, BNW, BBNW, slitted NW). In some aspects, the SAP-free and SAP-containing lanes may be selectively arranged on the nonwoven substrate to provide for faster absorbing SAP at the side margins of the absorbent core composite and slower absorbing SAP in the center/crotch region of the absorbent core composite.

In some aspects, the SAP-free lanes are empty other than the nonwoven substrate that forms the SAP-free lane. In other aspects, at least one of the SAP-free lanes contains non-absorbent material particles and/or fibers.

SAP-Free Lanes—Combinations of Different SAP Layers

In some aspects, different absorbent material layers containing MD SAP-free lanes and CD SAP-free lanes may be arranged within a single absorbent core composite. For example, an absorbent core composite may include at least three absorbent material layers, with an uppermost (bodyside) top absorbent material layer having MD SAP-free lanes, an intermediate absorbent material layer having CD SAP-free lanes, and a lowermost absorbent material layer having a uniform SAP layer with no SAP-free lanes.

The AM layers shown in FIGS. 6A, 6B, and 7A-7G may be used as any of the AM layers in any of the absorbent core composites disclosed herein.

SAP-Free Lanes in Multiple Different Layers

FIG. 8 depicts a combination of SAP layers, one with CD free lanes FL, AM1, and the other with MD free lanes FL, AM2. In some embodiments, the top SAP layer, AM1, will feature SAP free lanes in the MD so as to quickly disperse the initial, larger volume of fluid intake to other parts of the core with available SAP. The lower SAP layer, AM2, may also be equipped with MD SAP-free lanes for the same reason. But, in a further variation, the lower SAP layer may be equipped with CD SAP free lanes for other reasons. In some applications, the absorbent core composite may have top most layers and ADL layers that serve well to readily distribute the initial fluid intake in the z-direction. The lower SAP layer, in this case, may then serve to distribute the received fluid that flows into the lower levels in the y- and x-directions. It is contemplated, in this case, that such fluid volume may not be as large and may not be concentrated in the central region. Furthermore, the CD free lanes in the bottom layers will add some flexibility about the longitudinal axes (i.e., the lateral margins can more readily rotate to conform to the user's body during wear). As shown, core 810 includes an uppermost airthrough nonwoven, a lowermost SMS layer, and an intermediate nonwoven layer that is a slitted nonwoven. The slitted nonwovens disclosed herein may be the same or substantially similar to those disclosed in U.S. Pat. No. 8,785,715, the entirety of which is incorporated herein by reference.

SAP-Free Lanes Aligned with Embossing Lines

FIG. 9 depicts a core 910 including embossing lines, EL, that couple (e.g., adhere) adjacent nonwoven layers. Core 910 includes uppermost airthrough layer, AT, embossed with intermediate airthrough layer, AT, with AM1 sandwiched therebetween. AM1 includes SAP-containing lanes and SAP-free lanes. Core 910 also includes lowermost nonwoven, SMS, with AM2 sandwiched therebetween. The SAP-free lanes, FL, of AM1 are aligned with the embossing lines (EL) of the uppermost and intermediate AT layers, such that the uppermost and intermediate AT layers are embossed and adhered together without applying adhesive to the SAP, which would stiffen the SAP and possibly reduce the absorbency of the SAP. That is, the uppermost AT layer is only embossed with the intermediate AT layer at locations corresponding with the FL lanes of AM1. The alignment of SAP-free lanes with embossing lines also provides for bend or fold lines in core 910, facilitating fit when worn by a user by promoting flexibility of the core.

With the embossing lines coincident with the SAP-free lanes, core 910 is capable of bending/folding without disrupting the absolute and relative position of the SAP, and without disrupting the absorption properties of the SAP (e.g., by forcing SAP particles closer together). The embossing/fold/bend lines, thus, allow core 910 to move from a flat configuration into a folded and/or bunched configuration when worn by a user. As shown, the embossing/fold/bend lines, EL, extend parallel with the longitudinal extension of core 910. In some embodiments, at least one embossing/fold/bend line is coincident with the longitudinal centerline of core 910.

FIG. 9A depicts a simplified schematic of core 910 in a flat configuration, and FIG. 9B depicts a simplified schematic of core 910 in a bent or folded configuration, with the lateral side edges 913 encouraged upwards, bending at locations 912 along the core that are coincident with the EL of core 910.

When absorbent core 910, incorporated within an absorbent article, is worn by a user, forces imparted onto absorbent core 910 from the user's body may cause a bunching and/or folding of absorbent core 910. EL lines provide for or promote a controlled bunching of absorbent core 910. EL lines define pivoting lines, 912, during folding of absorbent core 910. For example, with absorbent core 910 positioned between a user's thighs, the user's thighs may exert forces upon absorbent core 910 that have a force component that is directed parallel to the lateral centerline of absorbent core 910, a force component that is directed in the z-direction, or combinations thereof. Such forces may result in a folding and or bunching of absorbent core 910 about and along EL lines, particularly in the central crotch region 915 of absorbent core 910. Such bunching and/or folding of absorbent core 910 may be confined to or at least concentrated at the central crotch region.

The particular shape into which core 910 is encouraged when worn may vary depending on, for example, the number of EL lines, the spacing between EL lines, the lateral width of EL lines, the spacing and width of SAP-free lanes and SAP-containing lanes, and the number of EL lines, SAP-free lanes, and SAP-containing lanes. Absorbent core 910 is not limited to folding into the shape shown in FIG. 9A.

In use, the EL lines of core 910 allow core 910 to dynamically respond to the dynamically changing forces that are imparted upon core 910 when worn by a user. For example, as a user walks, the forces imparted upon the core 910 vary with movement of the user's legs. The EL lines allow for the core 910 to at least partially fold and at least partially unfold dynamically in response to the variations in force imparted thereto. As shown in FIG. 9B, when folded or bent, core 910 may define a trough 917, with lateral sections 913 angled upwards relative to central section 915. Trough 917 may function to discourage leakage from the lateral side edges of core 910. That is, for fluid to flow past the lateral side edges of core 910, the fluid must flow upwards, against gravity, along the "wings" formed by lateral sections 913.

Slitting or Apertures

Figure 10:
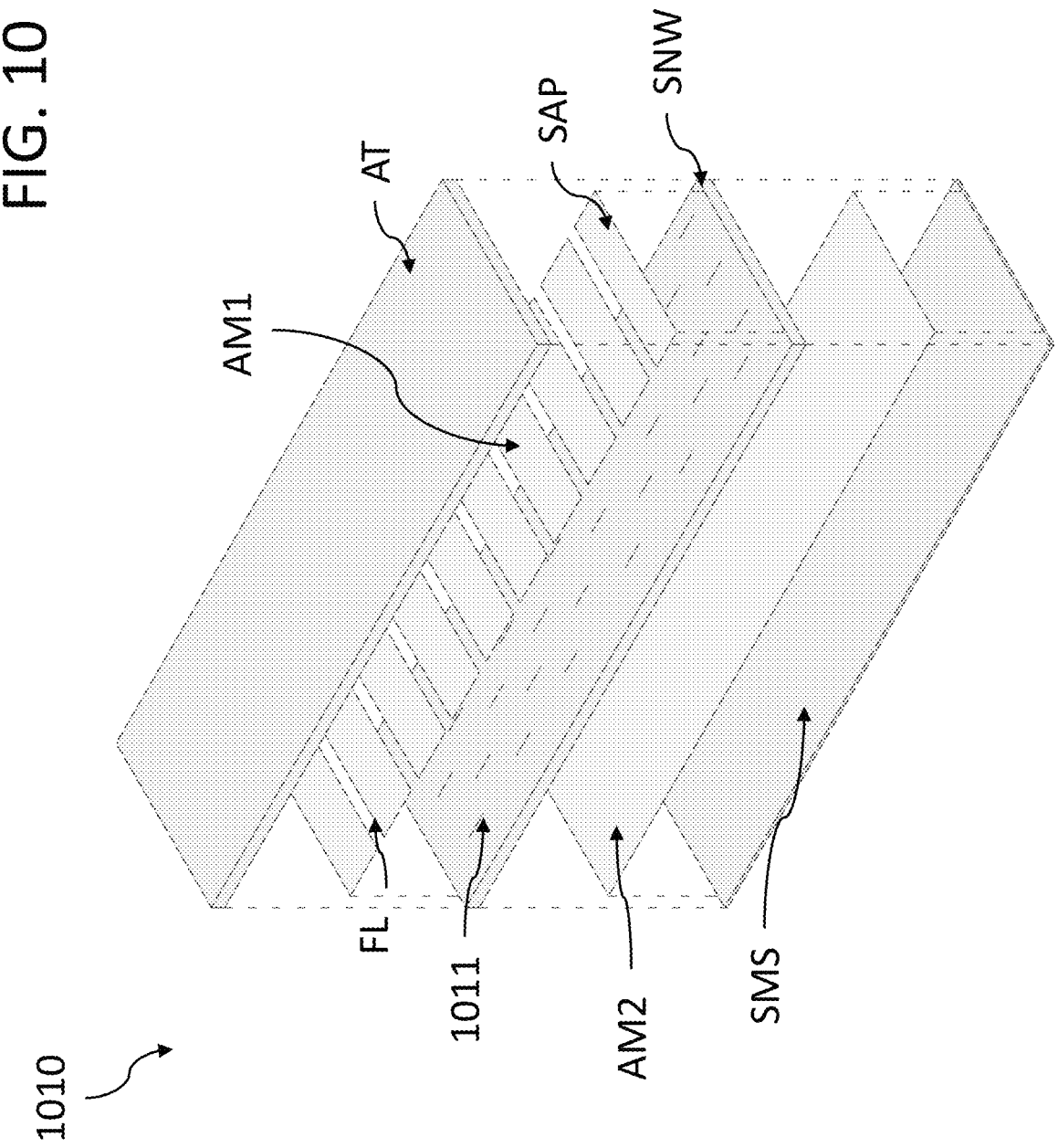
FIG. 10 is a perspective, exploded view of a multi-layer absorbent core composite or construction, including a slitted non-woven layer positioned in alignment with, adjacent, and downstream of an absorbent material layer featuring absorbent material-free lanes in the CD, which is suitable for incorporation into a disposable absorbent core composite.

FIG. 10 is a perspective, exploded view of a multi-layer absorbent core composite, MLC 1010, including a slitted non-woven layer, SNW, positioned in alignment with, and adjacent and downstream of an absorbent material layer, AM1, featuring absorbent material-free lanes FL in the CD. Initial fluid insult first impacts the uppermost nonwoven layer, AT, which distributes fluid flow to the uppermost absorbent material layer, AM1. The absorbent material-free lanes, FL, of AM1 facilitate distribution of the fluid intake to the lateral end margins of MLC 1010 by directed fluid laterally within MLC 1010. The slitted layer of nonwoven, SNW, includes a plurality of slits 1011. As shown in FIG. 10, slits 1011 are aligned and extend in the MD, perpendicular to the extension of the absorbent material-free lanes, FL, that are aligned and extend in the CD. However, the absorbent cores disclosed herein are not limited to this configuration and may include slits that are not aligned with one another, slits that extend in the CD, slits that extend orthogonal to the both the CD and MD, or slits that extend in parallel alignment with adjacent absorbent material-free lanes.

Slits 1011, positioned beneath SAP of AM1 layer, facilitate transport of fluid from AM1, through SNW, to another SAP-containing layer, AM2, which is positioned beneath SNW. As with other previously described composites, the bottom SAP-containing layer, AM2, provides additional storage capacity for residual fluid not absorbed by the top SAP layer, AM1.

Slitted nonwoven layers, such as SNW, may include any nonwoven, including NW, BNW, and BBNW, having one or more slits extending partially or fully therethrough. A slitted nonwoven may form the top sheet, back sheet, and/or any intermediate sheet of any of the absorbent core composites disclosed herein. The slits may extend only through (partially or fully) the nonwoven layer, without extending through other adjacent layers or through absorbent material (e.g., SAP particles), which can cause wear to slitting blades that form the slits. In certain aspects, the slits are concentrated or are only positioned in areas of the nonwoven layer that area aligned with the crotch region, where fluid flow is expected to be highest. The slits may be arranged and positioned such that the slits are spaced apart from embossing points and lines on the absorbent core composite, as embossing over a slit may reduce the size of the slit.

Slits—Interaction with SAP

In some aspects, when a slitted nonwoven layer is positioned above or below an absorbent material layer, at least some of the absorbent material (e.g., SAP) settles into or is otherwise positioned at least partially within the slits. In certain aspects, when vacuum force is used to apply and/or position the absorbent material onto the nonwoven layers, the vacuum force forces at least some of the absorbent material at least partially into the slits. In other embodiments, the slits are free of absorbent material.

In some aspects, if a slit is open and extends entirely through the nonwoven layer, from the bodyside surface to the opposite surface of the nonwoven layer, then at least some of the absorbent material is transported from a position above the slit (e.g., in an upper absorbent material layer), through the slit, and to a position below the slit (e.g., in a lower absorbent material layer). Thus, the slits may provide for transport of absorbent material from one absorbent material layer, such as AM1, to another absorbent material layer, such as AM2. In other aspects, the slits are too narrow for absorbent material to pass therethrough.

Slits—Alignment Relative to SAP and SAP-Free Lanes

In some aspects, the slits on a slitted nonwoven are aligned with SAP-free lanes of an absorbent material layer, e.g., to avoid deposition of SAP into the slits. Having slits aligned with the SAP-free lanes or areas may improve the fluid flow rate to lower areas of the core. In other aspects, the slits are aligned with SAP-containing lanes, e.g., to promote deposition of SAP into slits. The slits may be aligned with both SAP-containing lanes and SAP-free lanes. However, in some aspects, having SAP positioned over or in a slit may decrease the fluid flow rate into lower layers.

Systems and Processes for Forming SAP-Free Zones

Figure 11:
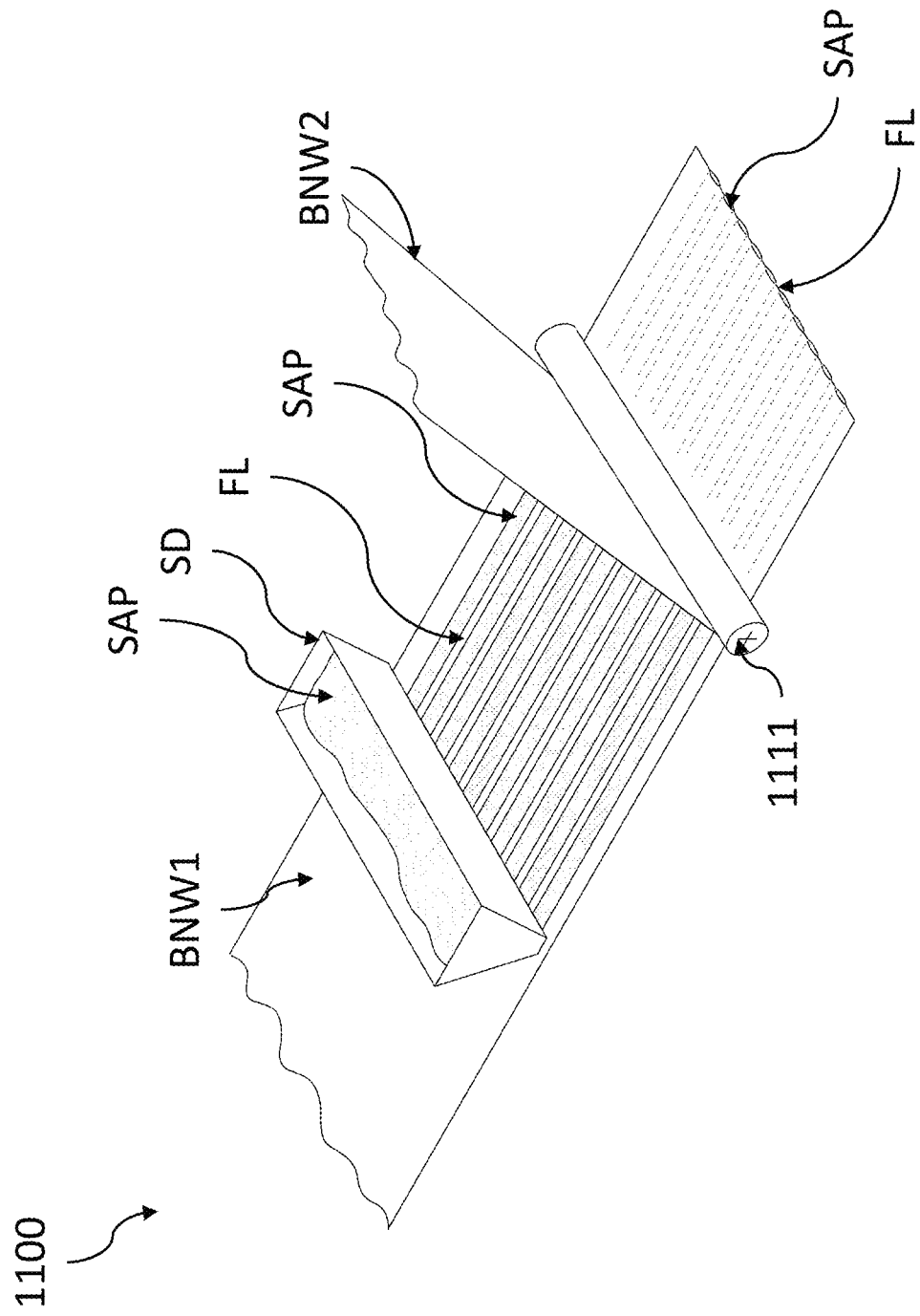
FIG. 11 is a simplified, perspective view of a system and a process for applying an absorbent material layer featuring absorbent material-free zones.

FIGS. 11 and 12 are simplified, perspective views of systems and processes for applying an absorbent core material layer featuring absorbent material-free zones, according to the disclosure. With reference to FIG. 11, system 1100 includes a SAP dispenser, SD, which may be a hopper with selectively positioned outlets (not visible in this view) that allow the SAP to be dispensed onto the bulky nonwoven (BNW1) in SAP lanes, with free lanes, FL, therebetween. System 1100 is configured to provide MD SAP lanes. Machine roller 1111 positions an additional bulky nonwoven (BNW2) over the deposited SAP; thereby, sandwiching the SAP between the two bulky nonwovens BNW1 and BNW2.

With reference to FIG. 12, system 1200 includes a SAP dispenser, SD, that deposits SAP onto bulky nonwoven BNW1 in SAP sections, with SAP-free lanes, FL, in both the CD and MD, such that a grid pattern is formed. The SD of FIG. 1100 may be adapted to have selectively openable and closable valves to open and close the outlet, allowing the SAP to be dispensed onto the bulky nonwoven BNW1 in SAP sections, with free lanes, FL, in the CD and MD. SD in FIG. 12 may apply an intermittent stream of SAP. This can be achieved by having an aperture on the SD that opens and closes. Alternatively, it can be accomplished by means of a gravure roll or a vibratory channel (with intermittent pulse of vibration).

In some aspects, SAP-free lanes are advantageous in areas which receive the highest flow volume/rate (i.e., at the target zone and closer to the top surface), because the SAP-free lanes provide void volume that allow more free flow toward the rest of the diaper in the z-, x- and y-directions. The SAP can absorb at a normal rate, but the excess liquid can bypass the SAP and reach other areas in the diaper via the SAP-free lanes, where the excess liquid can be absorbed and locked in by other SAP. Hence, a preferred embodiment of arranging the SAP-free areas would have the SAP-free lanes in the first or first several layers of absorbent material, optionally without any SAP-free lanes in the bottom SAP layer.

In some aspects, SAP properties are the same for all SAP layers or lanes in the composite. In other aspects, the properties of the SAP used in each layer or lane is controlled and varied to provide faster fluid acquisition, distribution, and more efficient utilization of the absorbent core. The SAP layer closest to the fluid discharge will have high fluid permeability to maximize fluid flow to the interior (z-direction flow) and lateral distribution (x-, y-direction flow). SAP-free lanes are advantageous in the top layers to provide the same functionality. A SAP with slower absorption rate may also be advantageously utilized in the top layers, as such SAP may provide for more fluid bypass during the high flow rate period of the fluid insult. The SAP layers may be progressively faster towards the bottom of the core. In some aspects, it is advantageous to match the particle size of the SAP to the BNW density for optimal particle immobilization therein. It may be possible to control the bulkifying process of the NW to obtain the desired density for optimal immobilization of a SAP particle size range, such as by manipulating the mechanical brushing process conditions (discussed in more detail below).

Online Fiber Scattering/Looses Fiber Layers

In certain aspects, multilayer absorbent core composites disclosed herein include at least one layer of "loose" fibers. As used herein, "loose fibers" refers to a population of a plurality of individual fibers that are not bonded to one another, such as in a web (e.g., the fibers do not form a nonwoven web or a woven web). Thus, each individual fiber of the loose fibers is separable from and movable relative to other individual fibers of the loose fibers.

FIGS. 13A-13C are diagrammatic, elevation views of multi-layer absorbent core composites or constructions, MLC 1300a, MLC 1300b, and MLC 1300c, each including a loose fiber layer 1301a or 1301b. The fiber layers 1301a and 1301b provide acute acquisition and distribution functions, and are strategically located in an upstream or more intermediate position adjacent a SAP layer. In FIGS. 13A and 13B, fiber layers 1301a and 1301b, respectively, are positioned between two SAP layers 1310a and 1310b, and facilitate the channeling of fluid intake not absorbed by the first SAP layer, 1310a, to additional SAP material in the second SAP layer, 1310b. Unlike other BNW layers, fibers of fiber layers 1301a and 1301b (also referred to a fiber network layers) are unbonded and facilitate more fluid flow between the two adjacent SAP layers, 1310a and 1310b. Without being bound by theory, it is believed that unbonded fibers allow for more control of the application of fiber layers 1301a and 1301b. The amount and constituency of fiber layers 1301a and 1301b may be varied, in the x-, y-, and/or z-directions. The unbonded fibers of fiber layers 1301a and 1301b are unrestrained, and may be manipulated to align or conglomerate to achieve a desired effect, where desired.

With reference to FIG. 13A, one exemplary absorbent composite, MLC 1300a, is depicted, including a single layer of scattered loose fibers, loos fiber layer 1301a. Loose fiber layer 1301a is shown as positioned between two absorbent material layers 1310a and 1310b. One skilled in the art would understand that such loose fibers may also be positioned between two nonwoven layers, or between a nonwoven layer and an absorbent material layer. The fibers may be scattered directly onto SAP and/or nonwoven. The scattered, loose fibers of loose fiber layer 1301a provide a layer of open void space within the MLC 1300a, which facilitates faster liquid acquisition within and through the MLC 1300a. In some aspects, SAP is applied onto the scattered, loose fibers of loos fiber layer 1301a, and is mixed therein. MLC 1300a also includes a bodyside nonwoven layer 1320a positioned above the first SAP layer 1310a, nonwoven layer 1320b positioned below second SAP layer 1310b, and third SAP layer 1310c positioned below nonwoven layer 1320b. Each nonwoven layer of a composite that includes scattered, loose fibers may be any nonwoven disclosed herein, including BNW and BBNW layers and slitted nonwoven layers. Each absorbent material layer of a composite that includes scattered, loose fibers may be any absorbent material layer disclosed herein, including those having SAP-containing lanes and SAP-free lanes.

The fibers of loose fiber layer 1301a may be arranged in a scattered, random configuration, as shown in FIG. 13A. In other aspects, the fibers of the loose fiber layer are arranged in an ordered configuration. For example, with reference to FIG. 13B, the fibers of loose fiber layer 1301b are aligned in the z-direction. The fibers may be aligned in other ordered configuration and or directions, such as in the x-direction or y-direction. The fibers of loose fiber layer 1301b may be aligned using electrostatic force (flocking). For example, the fibers may be of a composition that is capable of holding an electric charge (e.g., polyester fibers). In such aspects, an electric field applied to the fibers causes the fibers to align in one direction (MD, CD, or any desired direction). As the fibers are not bonded or otherwise attached to one another, the fibers are separable from one another, allowing the fibers to move into alignment in response to the electric field. After the desired alignment is attained, the application of the electric charge may be ceased.

Some fibers suitable for use as scattered fibers include, but are not limited to, cellulose fibers (e.g., wood pulp fibers, viscose fibers, rayon fibers), synthetic fibers (e.g., polypropylene fibers, polyethylene fibers, polyester fibers), or combinations thereof. In certain aspects, the fibers include multicomponent (e.g., bicomponent) fibers. As used herein, a "bicomponent" fiber is a fiber composed of two materials having different chemical and/or physical properties. For example, a bicomponent fiber may be a fiber composed of two different polymers. Bicomponent fibers may have a core/shell morphology.

In some aspects, all fibers within loose fiber layer are the identical or substantially identical in shape, size, composition, chemical properties, mechanical properties, and any other physical properties. In other aspects, fibers having a mixture of shapes, sizes, composition, chemical properties, mechanical properties, and/or any other physical properties are used within a loose fiber layer.

The properties of the loose fiber layer may be varied by varying any number of parameters including, but not limited to: the number and/or mass of fibers within the loose fiber layer, the composition of the fibers, the mixture of the fibers (e.g., mixtures of more than one fiber type), the density of the fibers, the thickness of the fibers, the length and/or width of the fibers, the chemical functionalities of the fibers (e.g., grafted fibers), as well as the placement, arrangement, and directionality of the fibers. The fibers may be positioned within SAP-containing lanes, within SAP-free lanes, within slits, on or within BBNW sections of a nonwoven, on or within non-bulkified sections of BNW, or combinations thereof.

In some aspects, a needle roll scatterer is used to scatter the fibers onto a layer of the absorbent core composite. In other aspects, flocking is used to deposit the fibers, where an electric field is applied to the web and the scattered fibers.

FIG. 13C depicts an alternative arrangement of layers of an absorbent composite that combines BNW, sectional BBNW, SAP-Free lanes, SAP-Containing lanes, loose fibers, and slitted nonwovens. MLC 1300c includes an uppermost, bodyside slitted nonwoven layer 1321, with a loose fiber layer 1301a positioned there below and deposited onto of an uppermost absorbent material layer 1311. The absorbent material layer 1311 includes SAP-Containing lanes 1311a and SAP-Free lanes 1311b. Below the absorbent material layer 1311 is positioned a sectionally bulkified bulky nonwoven layer 1323, including BBNW sections 1323a that are aligned with the SAP-containing lanes 1311a and non-bulkified sections 1323b that are aligned with the SAP-free lanes 1311b. Below the sectionally bulkified bulky nonwoven layer 1323 is positioned a SAP layer 1312 without SAP-free lanes, and below the SAP layer 1312 is positioned a BNW layer 1325 without any bulkified sections. Upon insult, the slitted nonwoven 1321 promotes fluid distribution towards the loose fiber layer 1301a, and the fibers of the loose fiber layer 1301a promote fluid distribution to both the SAP-free lanes 1311b and the SAP-containing lanes 1311a. The SAP in the SAP-containing lanes 1311a may be supported on or within the bulkified sections 1323a, which may promote wicking to the SAP layer 1312. The fibers un-bulkified sections 1323b may promote wicking of fluid from the SAP-free lanes 1311b to the SAP layer 1312. The SAP of the SAP layer 1312 may be supported on the fibers of the BNW layer 1325, which may promote wicking from one portion of the SAP layer 1312 to another portion of the SAP layer 1312.

In use, the fibers of the loose fiber layers disclosed herein may promote wicking, fluid distribution, and increase compressibility as well as comfort for the user. The fibers of the loose fiber layers may also direct the fluid flow within the core composite, particularly when the fibers are aligned, such as via an electric field.

Systems and Processes for Depositing Loose Fiber Layers

Figure 14A:
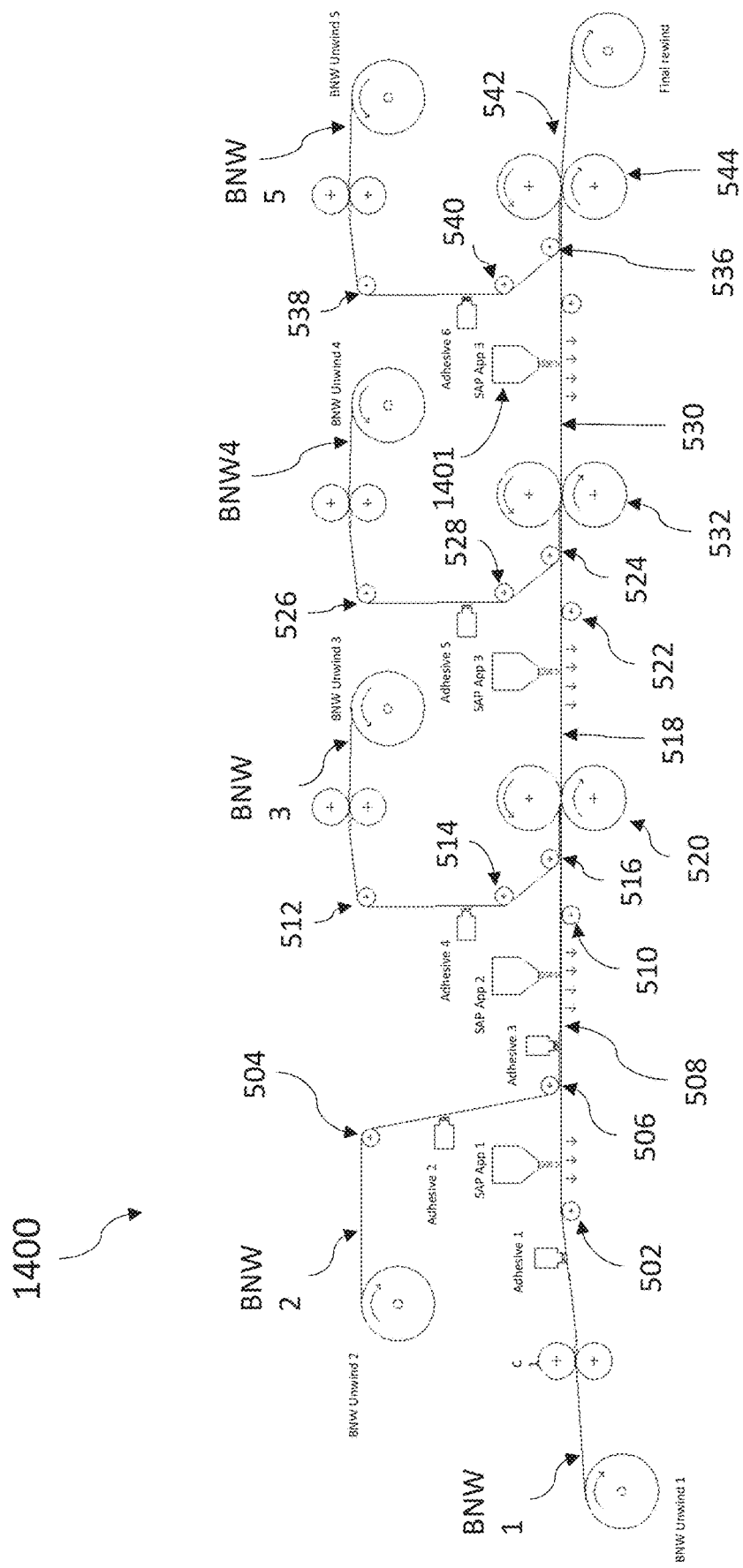
FIG. 14A is a schematic of a system and process for providing a loose fiber layer.

FIG. 14A depicts system 1400 for forming an absorbent core composite that includes a loose fiber layer. FIG. 14A is identical to FIG. 5, with the exception that "SAP App 5" is replaced with fiber applicator 1401. Fiber applicator 1401 is an apparatus that scatters or otherwise deposits fibers on the laminate of nonwoven fabric and/or absorbent material passing thereunder to form a loose fiber layer thereon. While the fiber applicator is shown in one position within the manufacturing process, the fiber applicator may be positioned at a different location in the manufacturing process, such that the loose fiber layer is at a different position within the absorbent core composite. Additionally, in some aspects, absorbent core composites having multiple loose fiber layers are formed.

Figure 14B:
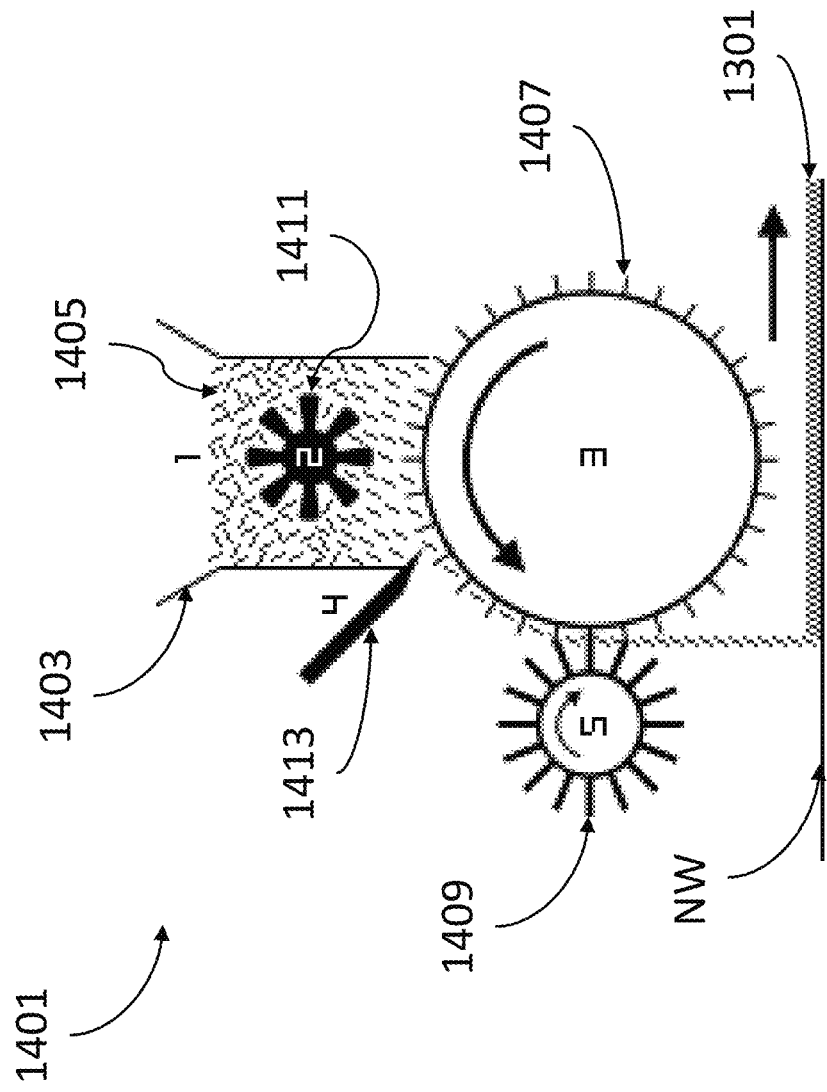
FIG. 14B is a schematic of a loose fiber applicator.

FIG. 14B depicts a detail view of one exemplary fiber applicator 1401. Fiber applicator 1401 may include hopper 1403 containing loose fibers 1405. Dispensing roller 1407, in conjunction roller 1409, may operate (e.g., rotate) to dispense discrete portions of loose fiber 1405 from hopper 1403 onto a nonwoven, NW, passing thereunder, forming loose fiber layer 1301 thereon. Fiber applicator 1401 also includes agitator 1411 for agitating fibers 1405, and dispensing regulator 1413 for regulating the dispensing of the fibers 1405.

In some embodiments, after the loose fibers are deposited (e.g., scattered) the loose fibers remain loose and unbonded within the absorbent core. In other embodiments, the loose fibers do not remain loose and unbonded within the absorbent core. For example, in some such embodiments, after the loose fibers are deposited onto a nonwoven, an adhesive or other bonding agent is applied on top of the loose fibers. In other such embodiments, the adhesive or other bonding agent is applied to the surface of the nonwoven prior to depositing the loose fibers on that surface. In some embodiments, the adhesive or other bonding agent is applied before or after SAP application on top of the loose fibers. When the adhesive or other bonding agent is applied after the SAP application, the adhesive or bonding agent may, in addition to securing the loose fibers, secure the SAP via bonding the SAP to the loose fibers, underlining nonwoven, or combinations thereof. The adhesive or bonding agent may be or include hot melt adhesive (HMA), which may be applied via a spray application or via applying particles that are subsequently activated by heat downstream (subsequent) in the process. Bonding may also be accomplished by using including at least some thermoplastic fibers within the mixture of loose fibers that are applied onto the nonwoven. Such thermoplastic fibers may be subsequently heated and thermally fused at the points where the loose fibers intersect one another, such that the loose fibers are bonded to form a web. Thus, the loose fibers may be applied loose, but may be subsequently bonded together within a web or web-like structure; thereby, forming a nonwoven web in situ. The thusly formed web, or loose fibers when not bonded, may contain SAP particles in some embodiments. In other embodiments, the formed web, or loose fibers when not bonded, is free of SAP particles and/or free of other absorbent material.

Bulkification—Opening of Bulky Nonwoven

In some aspects, at least one nonwoven layer of the absorbent core composite is subjected to "bulkifying" such that the nonwoven is "bulkified".

Bulkification—Pre- and Post Bulkification

Figure 15C:
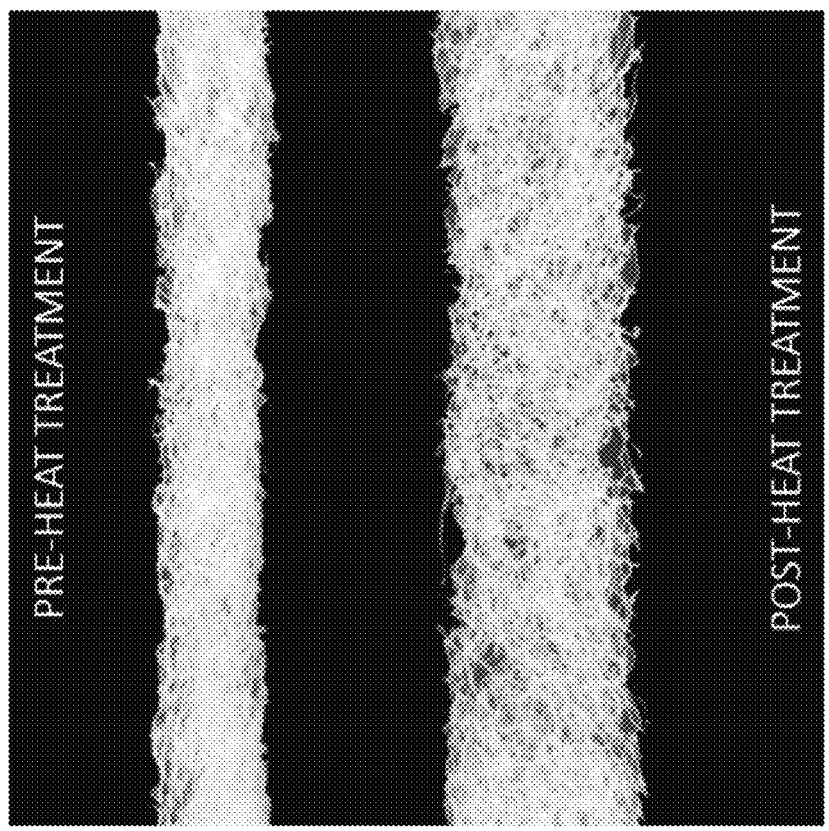
FIG. 15C is a photograph of a bulky nonwoven before and after bulkification.

With reference to FIGS. 15A, 15B, and 15C, a nonwoven is shown prior to and subsequent to bulkifying, respectively, is shown. Prior to being bulkified, the nonwoven has a first width, a depth, and a height. After being bulkified, the nonwoven has width, depth, and a height, at least one of which is greater than the prior width depth and height. Thus, the constituent fibers of the nonwoven occupy a greater volume after bulkification. As such, the nonwoven has a first bulk density prior to bulkification, and a second bulk density after bulkification, with the second bulk density being less than the first bulk density. As used herein, "bulk density" refers to the total mass of the nonwoven divided by the total volume the nonwoven occupies. As used herein, "bulk density" may be determined by any number of methods and techniques well known to those skilled in the art, including those disclosed in the Examples discussed with reference to FIGS. 22A and 22B.

Furthermore, bulkification of nonwoven increases the distance between adjacent fibers within nonwoven, thus increasing the overall void volume of nonwoven. As used herein, "void volume" refers to the volume occupied by nonwoven that is not occupied by solids (i.e., fibers), but is occupied by void (i.e., air space between fibers). As used herein, "void volume" may be determined by any number of methods and techniques well known to those skilled in the art, including those disclosed in the Examples discussed with reference to FIGS. 22A and 22B.

For the purposes of illustration, the increase in the volume of a single section of the total void volume of nonwoven is shown with reference to both FIGS. 15A and 15B. In FIG. 15A, prior to bulkification, a single section of nonwoven has a first void volume. After bulkification, that same single section of nonwoven has a second void volume that is greater than the first void volume. One skilled in the art would understand that the same volume increase of the void space of nonwoven would occur through nonwoven due to bulkification. Thus, the overall void volume of nonwoven increases due to bulkification.

In some aspects, an entire surface area of a nonwoven is bulkified. In other aspects, at least one section of a nonwoven is bulkified and at least one section of a nonwoven is not bulkified. In some aspects, only sections of nonwoven upon which SAP or other absorbent material is to be deposited are bulkified. For example, any of the bulkified nonwovens described herein may be include any of SAP-free lanes, as described elsewhere herein. The bulkified sections of the bulkified nonwovens may be aligned with the SAP-containing lanes, zones, or sections, such that SAP (or other absorbent material) is only or substantially only deposited onto the bulkified section of the nonwoven. In such aspects, the un-bulkified sections of the nonwoven (i.e., the sections of the nonwoven that have not be subjected to bulkification) are aligned with the SAP-free lanes. Thus, the bulkified sections may be applied to the nonwoven that corresponds with the pattern of SAP-free lanes, such that the non-bulkified sections are aligned with the SAP-free lanes. Bulkifying only certain selection sections or zones of a nonwoven and not bulkifying other selection sections or zones of the nonwoven allows for enhanced control over the capillarity of the nonwoven and associated absorbent material layer. In some embodiments, absorbent material is applied to only the bulkified sections of a sectionally BBNW.

Figure 16A:
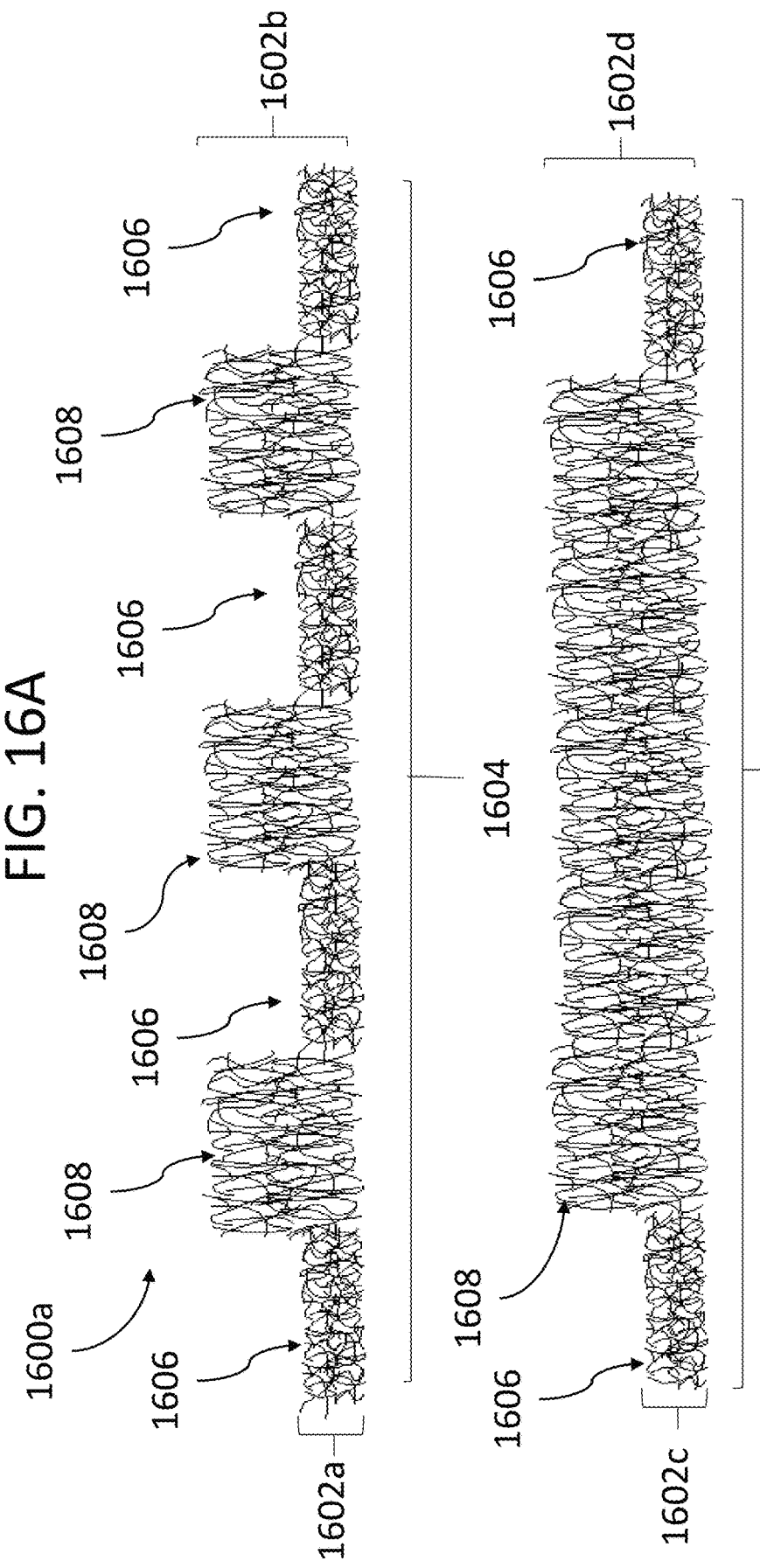
Figure 16B:
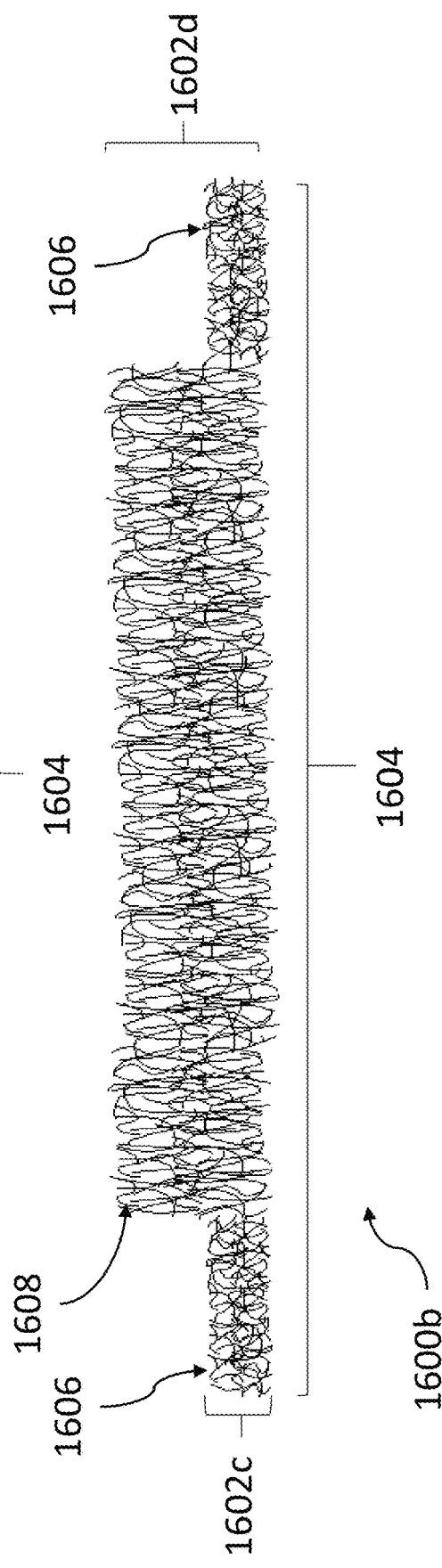

In some embodiments, absorbent material is applied to only the non-bulkified sections of a sectionally BBNW. In some embodiments, absorbent material is applied to both bulkified and non-bulkified sections of a sectionally BBNW. FIGS. 16A and 16B depicts cross-sectional views of nonwovens 1600*a* and 1600*b*, respectively. Nonwoven 1600*a* includes four non-bulkified lanes 1606, and three bulkified lanes 1608. Nonwoven 1600*b* includes two non-bulkified lanes 1606 along the side margins thereof, and a single bulkified section 1608 between the two non-bulkified lanes 1606.

With reference to FIG. 16C, in some aspects, bulkified bulky nonwoven layer 1600*c* includes longitudinal SAP-containing lanes 1650 formed adjacent bulkified lanes 1655. Bulky nonwoven 1660 can be selectively bulkified at bulkified sections 1665, and selectively not bulkified at unbulkified sections 1670. The bulkified sections 1665 will have a greater height in the y-direction, relative to the unbulkified sections 1670, forming the SAP-containing lanes 1650 within which SAP 1666 may be deposited and contained.

With reference to FIG. 16D, in some aspects, bulkified bulky nonwoven layer 1600*c* includes longitudinal SAP-free lanes 1650 formed adjacent bulkified lanes 1655. Bulky nonwoven 1660 can be selectively bulkified at bulkified sections 1665, and selectively not bulkified at unbulkified sections 1670. The bulkified sections 1665 will have a greater height in the y-direction, relative to the unbulkified sections 1670. SAP may be deposited in the bulkified lanes 1655 and not in the non-bulkified lanes 1650, such that the non-bulkified lanes 1650 form the SAP-free lanes. The SAP may be contained (e.g., entangled within the fibers of the bulkified sections 1655.

In use, the presence of fibers in the SAP-free lanes may help control the fluid compared to a completely empty channel. Although an empty channel has a higher void volume for fluid, it is essentially uncontrolled and may not wick along the channel. If the fiber network in the SAP-free lane has the proper capillarity, the liquid can wick and travel along the channel, supplying liquid to the SAP up to a height that the capillary structure of the NW can support. When the absorbent product is worn as a garment and is in a "U" shape, the areas raised relative to the insult point may have a capillary structure that supports wicking to its relative height for full utilization of the absorbent core. This can be achieved by selective bulkification around the insult point and, if needed, selective densification at the ends of the absorbent core.

In certain aspects, when SAP is applied to a BBNW, the SAP is in a dry state (and is not in the form of a wet slurry).

In certain aspects, a preferred absorbent core composite incorporating a BBNW includes: a top layer of an air-through nonwoven (ATNW); an intermediate, sectionally bulkified BBNW having two bulkified NW lanes with SAP contained therein; a lower ATNW layer; and a bottom SAP Layer. Alternating SAP and ATNW layers facilitates interlayer fluid distribution. The ATNW layers provide the bulk of the pathways for the liquid to spread within the core.

Bulkification—Absorbent Core Composite with Bulkified Nonwoven Layers

Figure 17:
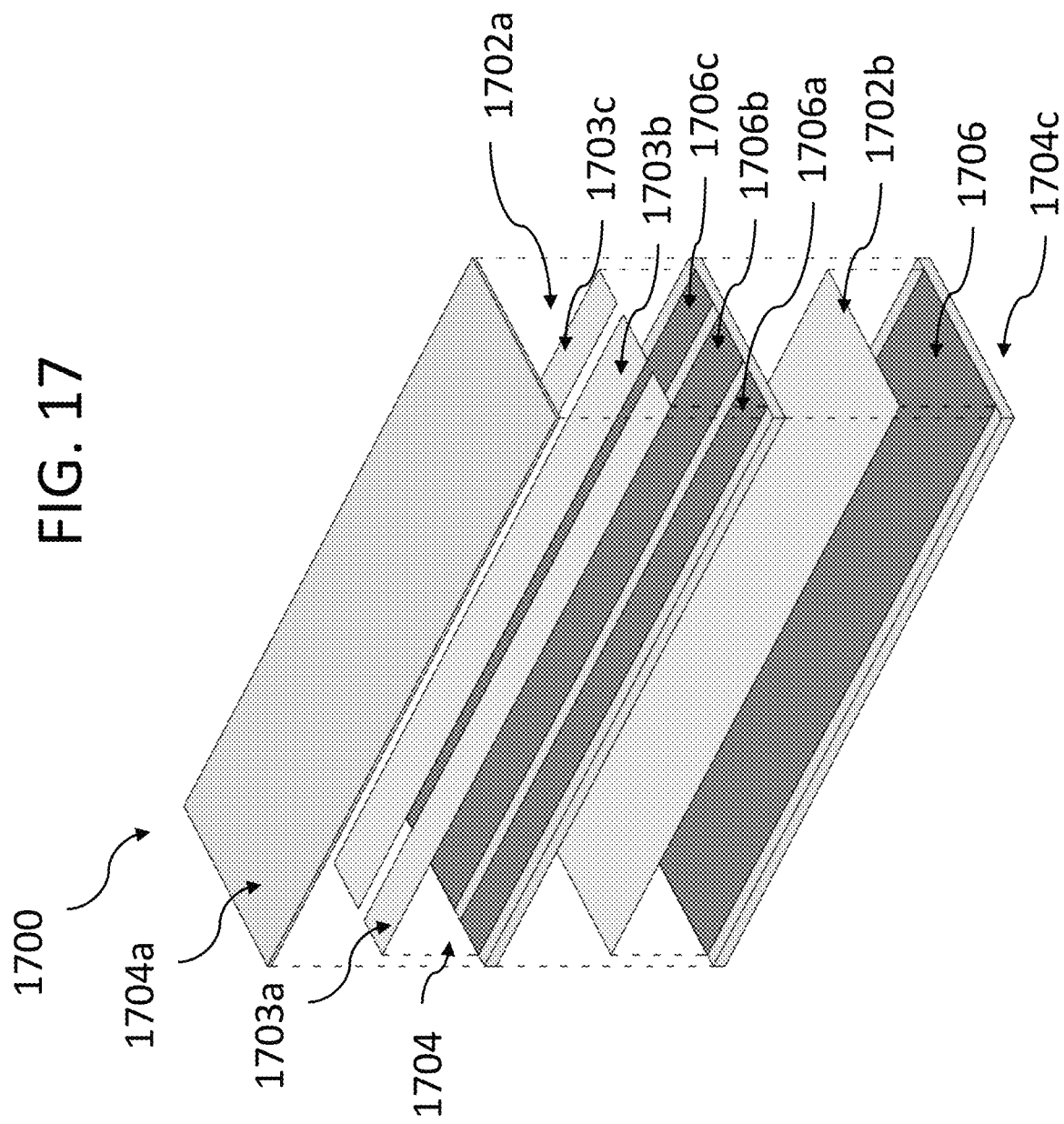
FIG. 17 is a perspective, exploded view of a multi-layer absorbent core composite or construction, including bulkified bulky nonwoven layers.

FIG. 17 depicts a perspective, exploded view of an absorbent core composite, MLC 1700, that includes multiple absorbent material layers 1702a and 1702b, and includes multiple nonwoven layers 1704a, 1704b, and 1704c.

In the embodiment shown in FIG. 17, a base or substrate nonwoven layer 1704c and an intermediate nonwoven layer 1704b are shown as having bulkified sections 1706, with the remaining sections being non-bulkified. A top or cover nonwoven layer 1704a does not include any bulkified sections. However, one skilled in the art would understand that absorbent core composites in accordance with the present disclosure may include bulkified sections 1706 or bulkified layers in arrangements that are different than is shown in FIG. 17. In some aspects, each nonwoven layer of an absorbent core composite includes at least one bulkified section or is an entirely bulkified layer. The base nonwoven layer, one or more intermediate nonwoven layers, the top nonwoven layer, or any combination thereof may include at least one bulkified section or may be an entirely bulkified layer. Also, while MLC 1700 is a multilayer composite, use of bulkified sections or layers of nonwoven is not limited to use with multilayer composites, and may be implemented in embodiments that include only one layer of nonwoven and/or only one layer of absorbent material.

Absorbent material layer 1702b is formed by depositing a plurality of SAP particles upon the bulkified section 1706 of base nonwoven layer 1704c. In some aspects, the SAP particles deposited onto the base nonwoven layer 1704c all have an identical set of properties. In other aspects, at least some of the SAP particles deposited onto the base nonwoven layer 1704c have at least one different property from at least some other of the SAP particles deposited onto the base nonwoven layer 1704c. The properties of SAP particles, which may be the same or different, include, but are not limited to, particle size, material composition, saturation and swell characteristics, treatments (e.g., whether and to what degree the SAP has been subjected to crosslinking), and other properties. For example, a first plurality of SAP particles may be positioned on the base nonwoven layer 1704c at a primary target region of the absorbent core composite 1700 (e.g., the expected area of insult) having a first set of properties, and at least one other plurality of SAP particles may be positioned on the base nonwoven layer 1704c at other regions of the absorbent core composite 1700. The position of SAP particles having varying properties within the absorbent core composite 1700 may be arranged to optimize fluid flow and distribution within the absorbent core composite 1700.

The intermediate nonwoven layer 1704b is positioned above the absorbent material layer 1702b, such that the absorbent material layer 1702b is sandwiched between the intermediate nonwoven layer 1704b and the base nonwoven layer 1704c. In some aspects, the intermediate nonwoven layer 1704b is bonded to the base nonwoven layer 1704c, such as by bond sites, points or lines, as disclosed in U.S. Pat. Nos. 9,757,284 and 9,789,014.

Absorbent material layer 1702a is formed by depositing a plurality of SAP particles upon the bulkified sections 1706 of intermediate nonwoven layer 1704b. In the same manner described above with respect to absorbent material layer 1702b, the SAP particles deposited onto the intermediate nonwoven layer 1704b (or onto at least one bulkified section 1706 thereof) may all have an identical set of properties, or the SAP particles may have varying properties from one bulkified section 1706 to another or within a single bulkified section 1706. For example, a first plurality of SAP particles 1703b may be positioned on the intermediate nonwoven layer 1704b at a primary target region of the absorbent core composite 1700 (e.g., the expected area of insult) within the bulkified section 1706b having a first set of properties, and two additional pluralities of SAP particles 1703a and 1703c may be positioned on the intermediate nonwoven layer 1704b at bulkified sections 1706a and 1706c at or near the margins of the intermediate nonwoven layer 1704b.

The top nonwoven layer 1704a is positioned above the absorbent material layer 1702a, such that the absorbent material layer 1702a is sandwiched between the intermediate nonwoven layer 1704b and the top nonwoven layer 1704a. In some aspects, the intermediate nonwoven layer 1704b is bonded to the top nonwoven layer 1704a, such as by bond sites, points or lines, as disclosed in U.S. Pat. Nos. 9,757,284 and 9,789,014.

In the embodiment shown in FIG. 17, only the sections of the nonwoven layers that have SAP deposited thereon are bulkified, with the remaining portions of the nonwoven layers remaining bulkified. However, in other aspects, portions of the nonwoven layers where SAP is not deposited may also be bulkified.

In some aspects, the top nonwoven layer 1704a and the intermediate nonwoven layer 1704b are air-through nonwovens, and the base nonwoven layer 1704c is an SMS nonwoven. In certain aspects, the bulkified nonwoven layers (in this embodiment, the intermediate nonwoven layer 1704b and the base nonwoven layer 1704c) function as acquisition distribution layers within the absorbent core composite.

Core Constructions Including Bulkified Sections or Layers

FIGS. 18A-18F depict various absorbent core constructions in accordance with certain aspects of the present disclosure.

Absorbent core composite 1800a, depicted in FIG. 18A, includes a top sheet layer 1801 of a bulky nonwoven that includes bulkified sections 1801a and un-bulkified sections 1801b. Absorbent material layer 1802 is positioned beneath top sheet layer 1801, and includes SAP-containing lanes 1802a and SAP-free lanes 1802b. As shown the SAP-free lanes 1802b are positioned beneath the bulkified sections 1801a and the SAP-containing lanes 1802a are positioned beneath the un-bulkified sections 1801b, allowing for transport of fluid form the bulkified sections 1801a into the SAP-free lanes 1802b, optionally absorption into the SAP within the adjacent SAP-containing lanes 1802a. Thus, the bulkified sections 1801a and SAP-free lanes 1802b may synergistically provide for a wicking path or channel to move fluids within the absorbent core composite 1800a to SAP contained within the absorbent core composite 1800a. In some aspects, this arrangement of reversed, such that the SAP-free lanes 1802b are positioned beneath the un-bulkified sections 1801b and the SAP-containing lanes 1802a are positioned beneath the bulkified sections 1801a. Slitted nonwoven layer 1803 is positioned beneath absorbent material layer 1802. As shown, the slits 1803a are aligned with the SAP-free lanes 1802b, providing a wicking path for fluid within the SAP-free lanes 1802b to flow to the second absorbent material layer 1804. This arrangement may be reversed, such that the slits are aligned with the SAP-containing lanes 1802a. This may allow for fluid to flow from the SAP-containing lanes 1802a to the second absorbent material layer 1804, such as if the SAP in the absorbent material layer 1802 is saturated. The second absorbent material layer 1804 is positioned beneath the slitted nonwoven layer 1803, and includes SAP-free lanes 1804a at the margins thereof, and a SAP-containing central lane 1804b between the SAP-free lanes 1804a. The top absorbent material layer 1802 may operate to direct fluid flow via the SAP-free and SAP containing lanes, while the second absorbent material layer 1804 may act as a bulk fluid absorption zone. Back sheet layer 1805 is shown as a bulky nonwoven. In some aspects, the top sheet layer 1801 is a body side layer.

Absorbent core composite 1800b, depicted in FIG. 18B, includes a top sheet layer 1801 of a slitted nonwoven. Absorbent material layer 1802 is positioned beneath top sheet layer 1801, and includes SAP-containing lanes 1802a and SAP-free lanes 1802b. Sectionally bulkified nonwoven layer 1803 is positioned below absorbent material layer 1802, and includes bulkified sections 1803a and un-bulkified sections 1803. As shown the SAP-free lanes 1802b are positioned above the bulkified sections 1803a and the SAP-containing lanes 1802a are positioned above the un-bulkified sections 1803b, allowing for transport of fluid form the SAP-free lanes 1802b into the bulkified sections 1803a, and optionally absorption into the SAP within the adjacent SAP-containing lanes 1804b. In some aspects, this arrangement of reversed, such that the SAP-free lanes 1802b are positioned above the un-bulkified sections 1803b and the SAP-containing lanes 1802a are positioned above the bulkified sections 1803a. The second absorbent material layer 1804 is positioned beneath the layer 1803, and includes SAP-free lanes 1804a at the margins thereof, and a SAP-containing central lane 1804b between the SAP-free lanes 1804a. Back sheet layer 1805 is shown as a sectionally bulkified bulky nonwoven, including bulkified sections 1805 aligned with the SAP-free lanes 1804a, and optionally un-bulkified sections (not shown) aligned with the SAP-containing lane 1804b. In some aspects, the top sheet layer 1801 is a body side layer.

Figure 18C:
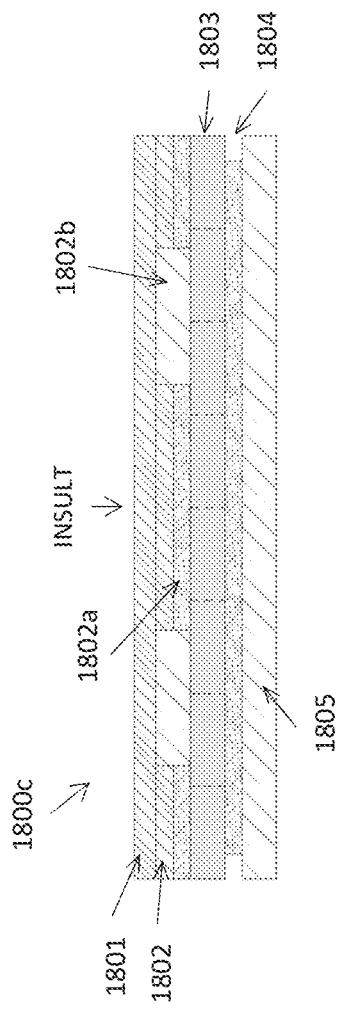

Absorbent core composite 1800c, depicted in FIG. 18C, includes a top sheet layer 1801 of a bulky nonwoven. Absorbent material layer 1802 is positioned beneath top sheet layer 1801, and includes SAP-containing lanes 1802a and SAP-free lanes 1802b. Absorbent material layer 1802 may be a layer the same or substantially similar to that shown in FIG. 16C, with SAP supported within un-bulkified sections of a bulky nonwoven and bulkified sections of the bulky nonwoven positioned therebetween. Slitted nonwoven layer 1803 is positioned below absorbent material layer 1802. Second absorbent material layer 1804 is positioned beneath slitted nonwoven layer 1803, and includes SAP and/or another absorbent material. Bulkified bulky nonwoven layer 1805 is positioned beneath second absorbent material layer 1804. Bulkified bulky nonwoven layer 1805 is not sectionally bulkified, but is entirely or substantially entirely bulkified over at least one surface thereof. In some aspects, the top sheet layer 1801 is a body side layer.

Figure 18D:
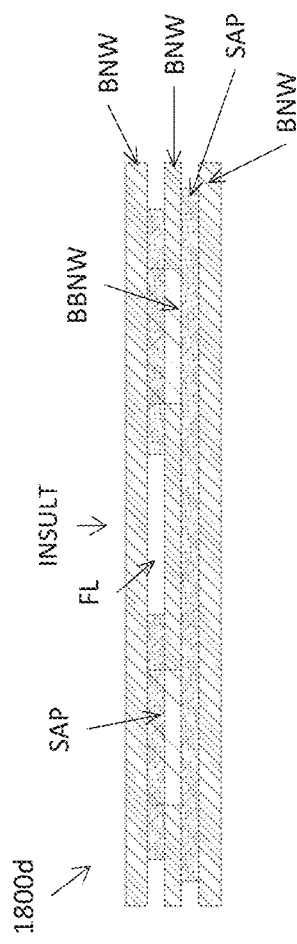

FIG. 18D depicts an alternative absorbent core construction 1800d. The top sheet layer, which is a NW, a BNW, and/or a BBNW, is the body side layer, and receives the insult, which passes through the top sheet layer into the first absorbent material layer, here shown as including both SAP-free lanes and SAP-containing lanes. At least some of the liquid from the top sheet layer flows into the SAP-containing lanes, and is absorbed into the SAP. Additionally, at least some of the liquid from the top sheet layer flows into the SAP-free lanes, where it may flow into the SAP of the SAP-containing lanes from the sides, or may flow down into the intermediate nonwoven layer. The intermediate nonwoven layer is shown here as a sectionally bulkified bulky nonwoven, including both bulky nonwoven sections, and bulkified bulky nonwoven sections. The BBNW sections are aligned with the SAP-containing lanes of the above absorbent material layer. The fibers of the BBNW form a wicking path for liquid in the SAP-containing lanes to flow down into the SAP-containing lane of the second absorbent material layer, which is positioned beneath the intermediate nonwoven layer. For example, if the SAP in the upper SAP-containing lanes is saturated, the liquid may flow through the BBNW fibers into the lower SAP-containing lane. The second absorbent material layer is supported on a bulky nonwoven layer.

Figure 18E:
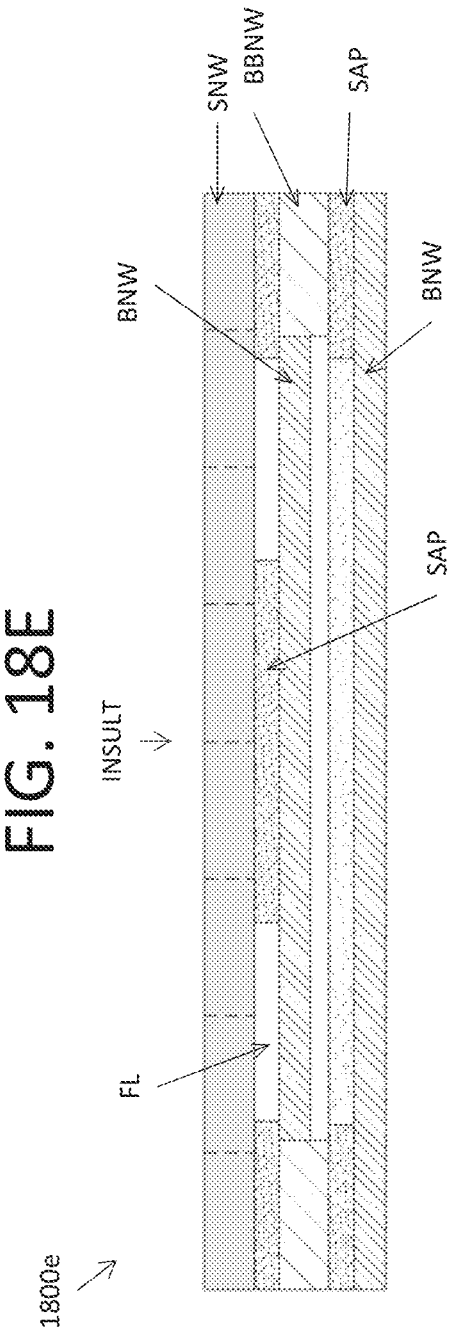

FIG. 18E depicts an alternative absorbent core construction 1800e. The top sheet layer, which is BNW with slits at least partially therethrough, is the body side layer, and receives the insult, which passes through the top sheet layer into the first absorbent material layer, here shown as including both SAP-free lanes and SAP-containing lanes. The slits of the top sheet layer are aligned with the SAP-free lanes, and direct fluid flow thereto. At least some of the liquid from the top sheet layer flows directly into the SAP-containing lanes and is absorbed into the SAP. Additionally, at least some of the liquid from the top sheet layer flows into the SAP-free lanes via the slits, where it may flow into the SAP of the SAP-containing lanes from the sides, or may flow down into the intermediate nonwoven layer. The intermediate nonwoven layer is shown here as a sectionally bulkified bulky nonwoven, including both bulky nonwoven sections, and a bulkified bulky nonwoven section. The BBNW section is aligned with both the SAP-containing lanes and the SAP-free lanes of the above absorbent material layer. The fibers of the BBNW form a wicking path for liquid in the SAP-free and SAP-containing lanes to flow down into the second absorbent material layer, which is positioned beneath the intermediate nonwoven layer. The second absorbent material layer includes a first SAP-containing lanes and a second SAP-containing lane. The second SAP-containing lane may contain SAP that is different from that in the first SAP-containing lane in at least one respect. For example, the second SAP-containing lane may contain SAP that is of a different type and/or material composition, a different size, or has different absorbent properties. In some aspects, the second SAP-containing lane is different from the first SAP-containing lane in that one of the lanes includes SAP mixed with non-SAP, and optionally non-absorbent, particles, such as spacing particles, inert particles, water-soluble particles, volatile particles, ion-exchange particles, or any combination thereof. The additive particles, such as ion-exchange particles, may be deposited in target areas. It is believed that ionic strength of urine as it passes through a bed of SAP materials (S) increases because of the SAP absorbing its water content. The introduction of ion exchange particles along the path of the liquid, including mixing such particles with the SAP, lowers the ionic strength of the liquid being absorbed there; thereby, maintaining the absorption capacity of the SAP. The second absorbent material layer is supported on a bulky nonwoven layer.

Figure 18F:
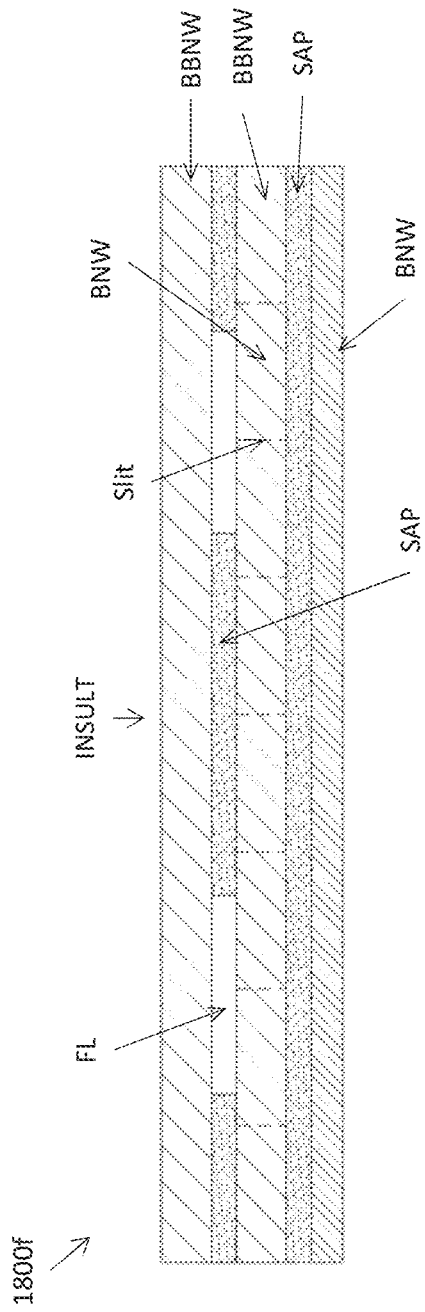

FIG. 18F depicts an alternative absorbent core construction 1800f. The top sheet layer, which is BBNW that is entirely bulkified on at least one surface thereof. The fibers of the BBNW layer receive the insult, which passes through the top sheet layer into the first absorbent material layer, here shown as including both SAP-free lanes and SAP-containing lanes. At least some of the liquid from the top sheet layer flows directly into the SAP-containing lanes and is absorbed into the SAP. Additionally, at least some of the liquid from the top sheet layer flows into the SAP-free lanes via the slits, where it may flow into the SAP of the SAP-containing lanes from the sides, or may flow down into the intermediate nonwoven layer. The intermediate nonwoven layer is shown here as a sectionally bulkified bulky nonwoven, including both bulky nonwoven sections, and a bulkified bulky nonwoven section. Optionally one or more sections of the intermediate BBNW layer may have slits therethrough. The bulkified section of the intermediate BBNW is aligned with a portion of the SAP-containing lanes and with both of the SAP-free lanes of the above absorbent material layer. The fibers of the BBNW form a wicking path for liquid in the SAP-free and SAP-containing lanes to flow down into the second absorbent material layer, which is positioned beneath the intermediate nonwoven layer. The second absorbent material layer is supported on a bulky nonwoven layer.

FIGS. 19A and 19B are cross-sectional views of an absorbent core composite including bulkified bulky nonwoven.

FIG. 19A depicts a cross-sectional view of an absorbent core composite 1680d. Absorbent core composite 1680d includes top sheet 1681, which may be a permeable layer, and back sheet 1682, which may be an impermeable layer. Sandwiched between top sheet 1681 and back sheet 1682 are multiple nonwoven layers and absorbent material layers. Below top sheet 1681, absorbent core composite 1680d includes slitted nonwoven 1683, having slits 1684 therethrough. Positioned below slitted nonwoven 1683 is bulkified bulky nonwoven layer 1685. Bulkified bulky nonwoven layer 1685 may be the same or substantially similar to layer 1600c, as shown in FIG. 16C, including an absorbent layer arranged in lanes of absorbent material 1686 (i.e., SAP-lanes) positioned in non-bulkified sections 1688 adjacent SAP-free lanes 1687 of bulkified nonwoven 1687. Positioned below bulkified bulky nonwoven layer 1685 is bulkified bulky nonwoven layer 1685b, which has a different pattern of bulkified and non-bulkified sections than does bulkified bulky nonwoven layer 1685. Bulkified bulky nonwoven layer 1685a includes side margins that are non-bulkified, 1688b and a central region that is bulkified, 1687b. In bulkified bulky nonwoven layer 1685a, the bulkified section 1687b contains SAP 1686b, and the non-bulkified 1688b is SAP-free. Bulkified bulky nonwoven layer 1685a is positioned above back sheet 1682. In some aspects, each layer of composite 1680d is adhered to adjacent layers. In certain aspects, only the nonwoven layers are adhered to each other, with the absorbent material entangled within the fibers of the nonwoven, but not adhered.

FIG. 19B depicts a cross-sectional view of a absorbent core composite 1690. Absorbent core composite 1690 includes top sheet 1691 and back sheet 1692. Sandwiched between top sheet 1691 and back sheet 1692 are multiple nonwoven layers and absorbent material layers. Below top sheet 1691, absorbent core composite 1690 includes nonwoven 1693. Positioned below nonwoven 1693 is bulkified bulky nonwoven layer 1694. Bulkified bulky nonwoven layer 1694 may include an arrangement of slits therethrough, and an arrangement SAP-lanes 1695 and SAP-free lanes 1698. Positioned below bulkified bulky nonwoven layer 1694 is absorbent material layer 1696, including SAP lanes 1695b and SAP-free lane 1698b. Absorbent material layer 1696 is positioned above nonwoven layer 1697.

In some aspects, depending on the fiber composition of the nonwoven being bulkified, application of heat after the bulkifying process may stabilize the low-density structure and the immobilization of the SAP. Most low-density nonwovens have bicomponent fibers in the fiber composition thereof. Such are fibers that have a low melting component that acts as a binder. Hence, reheating during the brushing/SAP deposition, and cooling immediately after, may cause some small percentage of re-bonding that could stabilize the structure of the bulkified nonwoven.

Forming discrete areas of controlled pore size or density in a nonwoven may be performed by densification (embossing) of the nonwoven, with the lowest density being dictated by the starting material nonwoven.

Forming discrete areas of controlled pore size or density in a nonwoven may also be performed by opening up ("bulkifying") the structure in discrete areas. In such aspects, the lowest density achievable is limited only by the process parameters. Combining the processes of discrete bulkifying and embossing may provide an even higher range (low to high) of densities that can be used for different applications.

In use, wicking in the y-direction (MD) is desirable. Bulking the NW close to the target area forms a pore structure with high void volume that can move fluid in a controlled fashion to supply the SAP that is in capillary contact therewith. The absorbent product is typically is in a "U" configuration, with an appreciable section needing to move fluid against gravity. Hence a structure that supports wicking flow is desirable. A fiber network structure with the appropriately-sized pores (i.e., web density) is desirable in such sections. This can be accomplished by building a pore gradient structure, with larger pores in the BNW at the target zone that transition to smaller pores towards the ends of the absorbent product. This variation in pore size can be achieved by bulkification, densification (embossing), or combinations thereof to achieve the desired pore gradient of large to small pores along the longitudinal (y-direction) of the absorbent product.

Bulkification—Mechanical Bulkifying Systems

FIG. 20 depicts bulkifying system 2000. Bulkifying system 2000 may be used to at least partially bulkify any of the nonwoven layers disclosed herein. Bulkifying system 2000 includes nonwoven supply or dispenser 2001, nonwoven manipulator 2003, and bulkified nonwoven collector 2005. Nonwoven supply 2001 provides densified, non-bulkified nonwoven 2004 to nonwoven manipulator 2003. For example, nonwoven supply 2001 may include spool 2002 from which nonwoven 2004 is unwound for input into nonwoven manipulator 2003.

Within nonwoven manipulator 2003, nonwoven 2004 is manipulated to form bulkified nonwoven 2018. Manipulation of nonwoven 2004 may include any of a variety of treatments or processes of nonwoven 2004 that result in the "bulkifying" of nonwoven 2004, such that nonwoven 2004 decreases in bulk density and increases in void volume; thereby, forming bulkified nonwoven 2018. The manipulation may include, but is not limited to, mechanical manipulation of the nonwoven 2004, thermal manipulation of the nonwoven 2004, or combinations thereof. During manipulation, the nonwoven is teased, brushed, fluffed, heated, and/or otherwise manipulated so as to "open" the fiber matrices of the nonwoven; thereby, decreasing the density and increasing the void volume of the nonwoven. In some aspects, both the body side surface of the nonwoven and the surface opposite the body side surface are "bulkified", such as by brushing both sides of the nonwoven and/or heating the nonwoven. In certain aspects, only the side of the NW that has SAP deposited thereon is bulkified. In such aspects, the un-brushed side of the NW will be denser and have less void volume than the brushed side, such that the non-brushed side will capture the SAP, reducing or preventing the filtering of the SAP through the NW layer.

When thermal manipulation is used to bulkify the nonwoven, heat may be applied to one or both sides. In some aspects, even when heat is applied to only one surface of the nonwoven, both surfaces of the nonwoven exhibit bulkification. In some aspects, only the surface of the nonwoven upon which SAP is applied is bulkified.

In the embodiment shown in FIG. 20, the manipulation is a mechanical manipulation that includes using brushes 2010a and 2010b (e.g., rotary brushes) to brush the surfaces of the nonwoven as the nonwoven passes through nonwoven manipulator 2003. The nonwoven is transmitted through the nonwoven manipulator 2003 such that surfaces of the nonwoven engage with bristles 2012 of the brushes 2010a and 2010b. For example, a series of machine rollers 2008, 2014, 2019, and 2020 may operatively engage the nonwoven, and roll to transmit the nonwoven through the nonwoven manipulator 2003. As the bristles 2012 engage the surface of the nonwoven the bristles may brush and/or tease the fibers of the nonwoven to pull the fibers relative to one another, resulting in the bulkification of the nonwoven. As the fibers are brushed, the fibers are displaced relative to each other due to the brushing action, resulting in more void space between fibers being created. As such, the sheet thickness of the nonwoven increases and the density of the nonwoven decreases. As arranged in FIG. 20, the brushes 2010a and 2010b engage and manipulate both, opposing surfaces of the nonwoven. However, in some aspects, only one surface of the nonwoven is manipulated. Furthermore, while each surface of the nonwoven is depicted as being manipulated by a single brushing apparatus, in some aspects, multiple brushes arranged in series engage with and manipulate one or more of the surfaces of the nonwoven. In some aspects, multiple brushes are arranged in parallel, with each of the brushes arranged to engage and manipulate a selected section of the nonwoven.

Bulkification—Brush Configurations

With reference to FIG. 20A, a brushing apparatus 2010c is shown, which includes a central brushing region 2012 that includes bristles attached to a machine roller or brush axle 2015, and two non-brushing regions 2013 on either side of the brushing region 2012. When passing by a brush, such as brush 2010c, sections of a nonwoven that are aligned with and engage the central brushing region that includes 2012 will be bulkified, while the portions of the nonwoven that are aligned with the two non-brushing regions 2013 will remain un-bulkified (densified).

With reference to FIG. 20B, a brushing apparatus 2010d configured to provide a nonwoven with lanes of bulkified sections and lanes of un-bulkified sections is depicted. Brushing apparatus 2010d includes brushing region that include bristles 2012 attached to a machine roller or brush axle 2015, and non-brushing regions 2013 adjacent to the brushing regions 2012. When passing by a brush, such as brush 2010c, sections of a nonwoven that are aligned with and engage the central brushing region that includes 2012 will be bulkified, while the portions of the nonwoven that are aligned with the two non-brushing regions 2013 will remain un-bulkified (densified). Thus, the arrangement of multiple brushes and the arrangement of the bristled on each brush may be configured and arranged to provide a selected pattern of bulkified and un-bulkified sections on a nonwoven. The pressure with which the bristles 2012 of each brushing apparatus 2010 and the rate at which the bristles 2012 of each brushing apparatus 2010 move relative to the surface of the nonwoven (e.g., the speed at which the roller axle 2015 rotates) may be varied to, thus, vary the presence and/or degree of bulkification of the nonwoven. As shown, the rotary brushes 2010a and 2010b rotate counter to the movement of the nonwoven. The bristles 2012 in this, and in any other of the embodiments disclosed herein, may be nylon bristles, or any other type of bristle. While the mechanical manipulator is shown and described herein as including brushes, the mechanical manipulator may be any structure, machine, system, or apparatus configured to manipulate, tease, and/or encourage the nonwoven to bulkify.

With reference to FIG. 20C, an alternative brush 2010c is depicted. Brush 2010e includes bristles that extend from axle 2015 at a first distance y1, and bristles that extend from axle 2015 at a second distance y2. The second distance y2 is greater than the first distance y1, because the bristles that extend distance y2 are longer than those that extend distance y1. From the bristles that extend distance y1 to the bristles that extend distance y2 are bristles that extend distances that are intermediate of distances y1 and y2, such that the bristles 2012 on axle 2015 progressively and continually (or continuously) decrease in length from the central bristle region 2017a to the margins 2017b along the x-direction.

With reference to FIG. 20D, an alternative brush 2010d is depicted. Brush 2010d includes different regions of bristles 2012, including region 2044a and regions 2044b. Each region of bristles varies in at least one aspect. For example, the bristles 2012 between regions 2044a and 2044b may vary in: length of bristles, width of bristles, density of the packing of bristles (i.e., number of bristles unit of surface area of the axle surface), bristle composition, and bristle stiffness.

Figure 21:
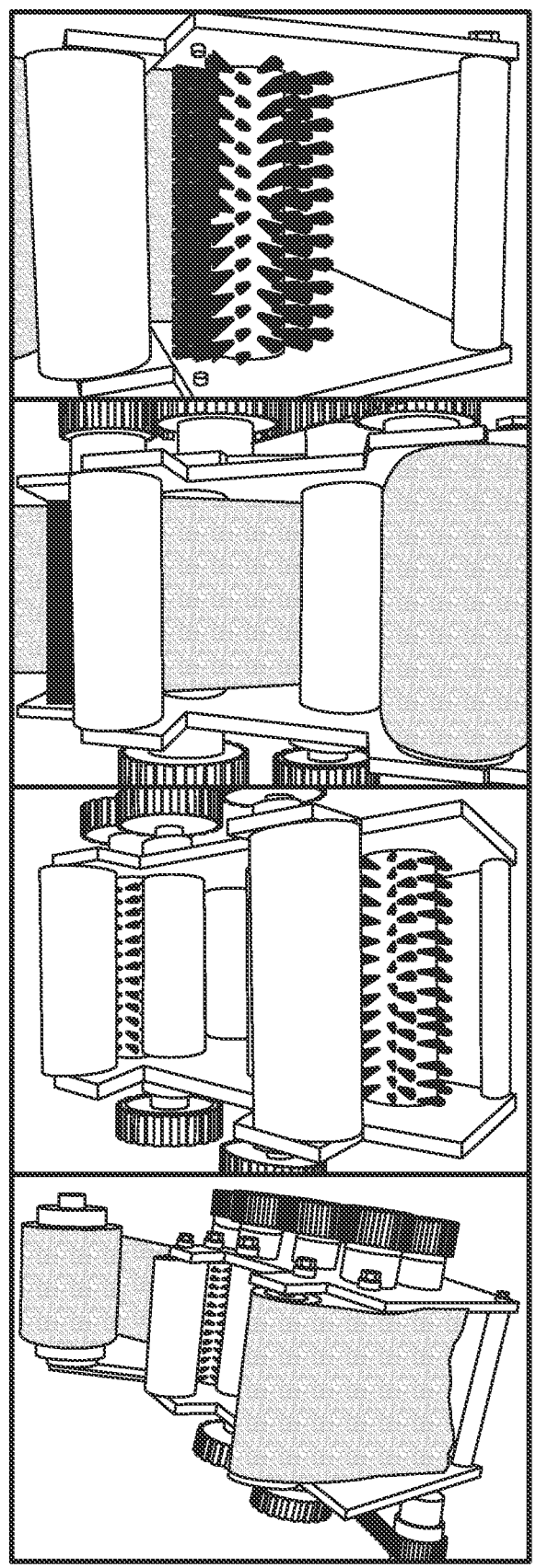
FIG. 21 is a photograph of an exemplary bulkifying system including brushes.

Referring again to FIG. 20, in operation nonwoven 2004 is unwound from spool 2002 and fed into nonwoven manipulator 2003. Within nonwoven manipulator 2003, nonwoven 2004 is operatively engaged with first roller 2008, which feeds nonwoven 2004 to second roller 2014. While moving over second roller 2014, bristles 2012 of brushing apparatus 2010a engage with and manipulate nonwoven 2004. As shown, axle 2015 rotates in a first direction and second roller 2014 rotates in a section, opposite direction. Rotation of axle 2015 causes bristles 2012 to rotate in a direction opposite of the movement of nonwoven about second roller 2014. Bristles 2012, thus, at least partially bulkify nonwoven 2004 in at least selected locations. At least partially bulkified nonwoven 2016 is then transmitted from second roller 2014 to third roller 2019. While moving over third roller 2019, bristles 2012 of brushing apparatus 2010b engage with and manipulate nonwoven 2004. As shown, axle 2015 rotates in the second direction and third roller 2019 rotates in the first, opposite direction. Rotation of axle 2015 causes bristles 2012 to rotate in a direction opposite of the movement of nonwoven 2016 about third roller 2019. Bristles 2012, thus, further bulkify nonwoven 2016 in at least selected locations, forming bulkified nonwoven 2018. As shown, the bristles 2012 of the second brush 2010b engage with and contact a first surface of the nonwoven, while the bristles 2012 of the first brush 2010a engage with and contact the surface of the nonwoven opposite the first surface. From the third roller 2019, the bulkified nonwoven 2018 is fed to fourth roller 2020, where the bulkified nonwoven 2018 exits the nonwoven manipulator 2003. From the fourth roller 2020, the bulkified nonwoven 2018 is fed to a spool 2022 for collection thereon. In some aspects, the bulkified nonwoven 2018 is fed directly from the nonwoven manipulator 2003 into a system or apparatus for forming an absorbent core composite. For example, the bulkified nonwoven 2018 may be fed to an apparatus for depositing absorbent material therein and/or for bonding other nonwovens thereto. FIG. 21 is a photograph depicts an exemplary bulkifying system.

Bulkification—Mechanical and Thermal Bulkifying Systems

Figure 23:
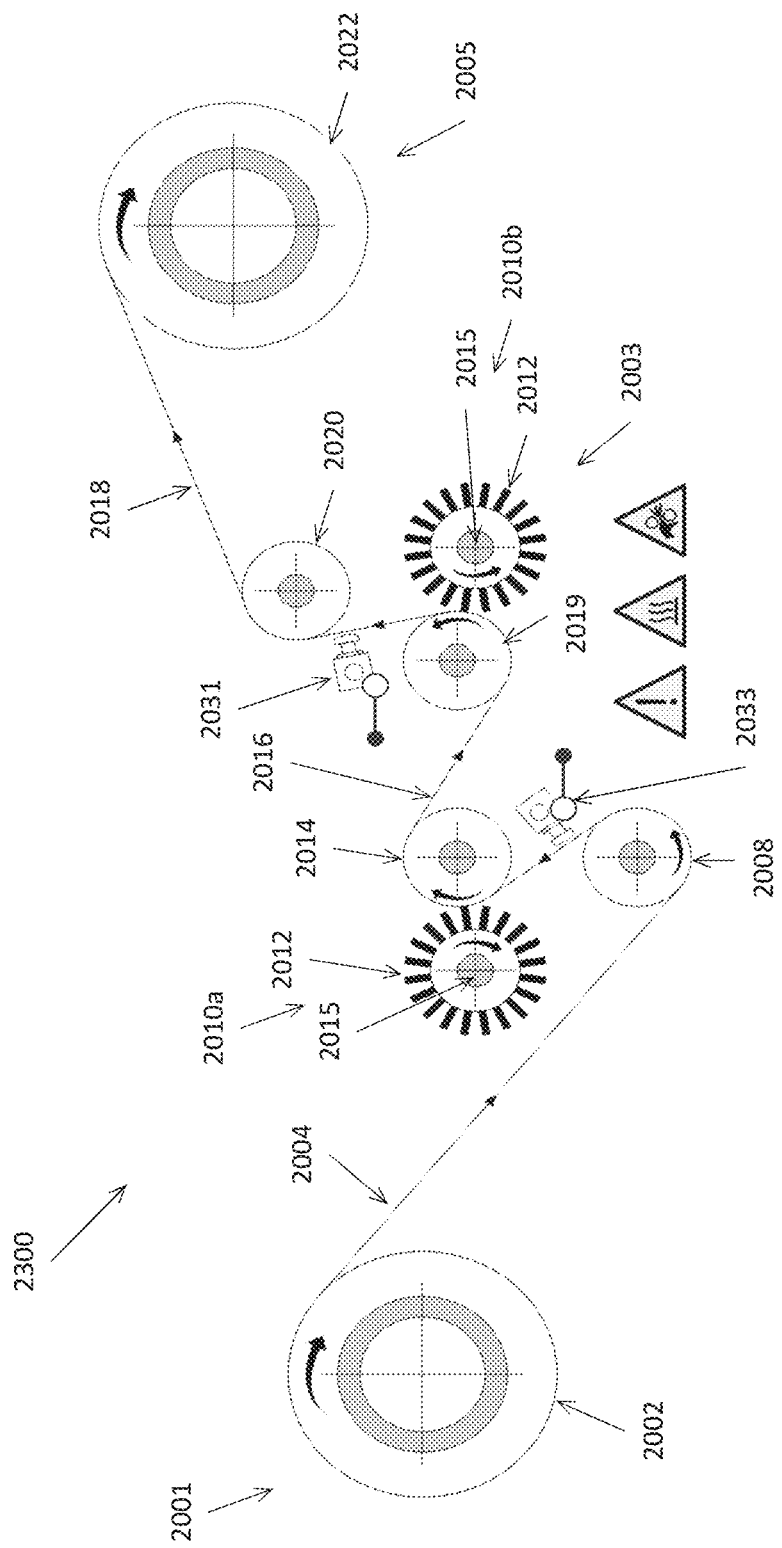
FIG. 23 is a schematic of a system and process for bulkifying a nonwoven substrate, including both thermal and mechanical manipulation.

FIG. 23 depicts an alternative bulkifying system 2300. Bulkifying system 2300 is substantially similar to bulkifying system 2000, as shown in FIG. 20, with like reference numeral identifying like parts. In addition to the mechanical manipulation, as shown and described with reference to FIG. 20, bulkifying system 2300 includes thermal treatment of the nonwoven to promote bulkificaiton thereof. In the embodiment shown in FIG. 23, the thermal treatment is accomplished using a hot air nozzle 2033 and a cold air nozzle 2031. However, any number of structures may be used to thermally treat the nonwoven to increase and/or decrease the temperature thereof, and encourage bulkification thereof. As shown, hot air nozzle 2033 is incorporated into nonwoven manipulator 2003, and is interposed between first roller 2008 and first brush 2010a. Hot air nozzle 2033 imparts a stream of heated air onto the nonwoven 2004 prior to the nonwoven being mechanically manipulated by first brush 2010a. The heated air may be at a temperature above ambient temperature, such as at 80° C. or above. Heating the nonwoven 2004 may cause the fibers of the nonwoven 2004 to become more pliable, relative to the nonwoven 2004 prior to heating. As such, brushing of a heated nonwoven may result in a greater degree of bulkification (i.e., a greater decrease in bulk density and a greater increase in void volume) of the nonwoven, at least in part because the fibers are more pliable for manipulation by the bristles 2012. As shown, cold air nozzle 2031 is incorporated into nonwoven manipulator 2003, and is interposed between third roller 2019 and fourth roller 2020, after second brush 2010b. Cold air nozzle 2031 imparts a stream of cold air onto the bulkified nonwoven 2018 after the nonwoven has been mechanically manipulated by first brush 2010a and second brush 2010b. The cold air is at a temperature below that of the heated air nozzle 2031, and may be below ambient temperature. The cold air functions to cool the nonwoven prior to further processing thereof. In some aspects, focused IR may be used to selectively heat sections of the NW web, allowing for selective bulkification of sections of the NW webs.

In some aspects, bulky nonwovens may be "printed" via thermal and/or mechanical means to have a desired pattern of bulkified and non-bulkified sections. The thermal and/or mechanical means may continuously or intermittently bulkify the nonwovens.

While shown in FIGS. 20 and 23 as providing bulkified sections in the machine direction, in some aspects, bulkified sections or lanes may be provided in the cross direction. For example, the brush apparatus may have sections in the cross direction that does not have bristled such that, or the brush apparatus may intermittently engaged with the nonwoven with bristles such that some cross directional portions of the nonwoven are bulkified and some are not.

In some aspects, one or more parameters of the system and or process for bulkifying the nonwoven may be varied to vary one or more aspects of the bulkification. For example, the aspects of the bulkification that may be varied include, but are not limited to, the position of the bulkification in the x-, y-, and/or z-directions; the degree of the bulkification (i.e., the degree to which the bulk density is decreased and the degree to which the void volume is increased). Aspects of the bulkification system or process that may be varied include, but are not limited to, the speed at which the brush moves relative to the nonwoven, the thickness of the bristles of the brush, the length of the bristles of the brush, the material of the bristles of the brush, the spacing between the bristles of the brush, the spacing between bristles of the brush and the nonwoven, the pattern of the bristles of the brush, the number of brushes used during bulkification, the temperature of the heated air from the hot air nozzle, the velocity of the heated area from the hot air nozzle, the distance between the hot air nozzle and the nonwoven, and the number of hot air nozzles used during bulkification.

Bulkification—Increased Loft and SAP Retention

Bulkification of the nonwoven may result in an increase in the loft of the nonwoven. Furthermore, bulkification "opens" up the nonwoven web of fibers by decreasing the bulk density and increasing the void volume; thereby, increasing the distances between each of the individual fibers of the nonwoven web of fibers. Such opening of the web of fibers increases the softness and compressibility of the nonwoven, relative to the nonwoven prior to opening.

Such opening of the nonwoven web allows for an increased amount of absorbent material (e.g., SAP) to be contained within the nonwoven, relative to the amount of SAP that may be contained within the nonwoven prior to bulkification, as more SAP can penetrate into and fit within the more open fiber matrix of the nonwoven. This allowed the SAP to become more thoroughly mixed with the fibers of the nonwoven relative to the nonwoven prior to opening. As such, more SAP is entangled with the nonwoven fibers than would be if the nonwoven were not subjected to such opening. The SAP is at least partially immobilized due to the entanglement within the fibers of the nonwoven. In some aspects, the opening of the nonwoven increases the degree and/or amount of such SAP immobilization within the fiber web. As such, the amount of adhesive, such as hot melt adhesive (HMA), required from immobilization of SAP within the nonwoven may be reduced or eliminated. For example, the amount of HMA may be reduced by from 10 to 50 wt. % relative to the amount required without bulkification. With the increased SAP retention within the open nonwoven, the absorbent core composite may exhibit an increased rate of fluid intake, at least at the regions of the absorbent core composite where bulkified sections of the nonwoven contain SAP.

In some aspects, bulkification of a nonwoven results in a decrease in the bulk density of the nonwoven by from 5% to 50%, or from 10% to 40%, or from 15% to 30%, or from 18% to 25%, relative to the bulk density of the nonwoven prior to the bulkification. In certain aspects, bulkification of a nonwoven results in a decrease in the bulk density of the nonwoven of at least 5%, or at least 10%, or at least 15%, or at least 18%, or at least 20%, or at least 25%, or about 24% or about 27%, relative to the bulk density of the nonwoven prior to the bulkification.

In some aspects, bulkification of a nonwoven results in an increase in the void volume of the nonwoven by from 5% to 75%, or from 10% to 60%, or from 15% to 50%, or from 20% to 40%, or 25% to 35%, relative to the void volume of the nonwoven prior to the bulkification. In certain aspects, bulkification of a nonwoven results in an increase in the void volume of the nonwoven of at least 5%, or at least 10%, or at least 20%, or at least 30%, or at least 40%, or at least 45%, or about 37% or about 45%, relative to the void of the nonwoven prior to the bulkification.

In some aspects, after bulkification, the nonwoven is subsequently, at least partially compressed, which reduces or eliminates the bulkification. In some such aspects, the SAP is applied to the bulkified bulky nonwoven prior to compression thereof, such as immediately after the bulkification thereof. After bulkification, subsequent processing of the BBNW, associated absorbent core composite, associated absorbent article (e.g., diaper), or associated final packaging thereof may at least partially compress the BBNW, absorbent core composite, and/or absorbent article, such that the bulk density of the BBNW is at least partially increased and the void volume of the BBNW is at least partially decreased. In certain aspects, the BBNW, even after such subsequent processing, has a lower density and higher void volume relative to the BNW prior to bulkification. As such, at least some of the bulkification remains in the final product, aiding the product performance. Regardless of whether or not any of the bulkification remains in the final product, the bulkification allows for increased entanglement of SAP within the fibers of the BNW during production of the absorbent core composite.

Bulkification—Examples—Brushing of Two Nonwovens

Figure 22A:
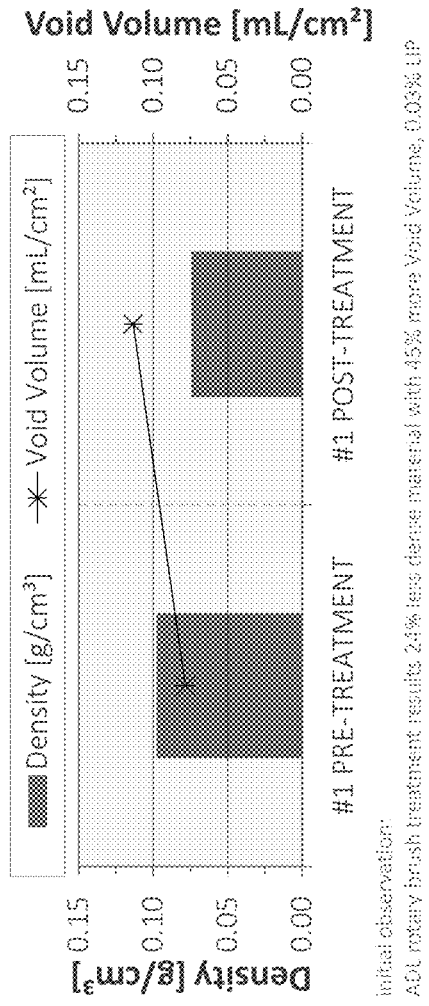
FIGS. 22A and 22B are bar graphs showing data collected during the bulkification examples described herein.
Figure 22B:
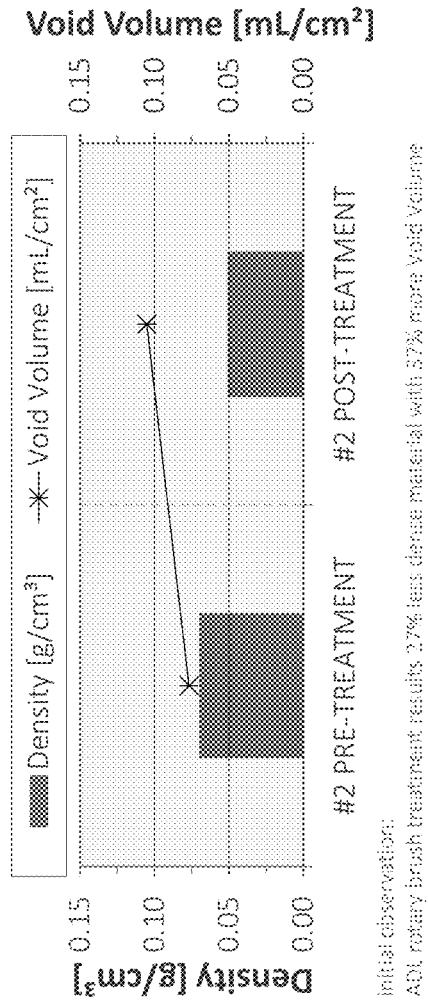

With reference to FIGS. 22A and 22B, two air-through bonded nonwovens were subjected to brushing in a system in accordance with FIG. 20 and FIG. 21.

Experimental Processing Parameters—In these Examples, the material processing was performed under ambient conditions, without use of external heating (or material wetting ambient conditions, at a temperature of 16° C. and 40% relative humidity (RH). All materials were acclimated to the ambient conditions prior to testing. The processing parameters used in the examples included: (1) a nonwoven web feed at 30 gear; (2) a brush treatment at 24 gear; (3) a ratio of nonwoven web to brush treatment of 4:5 (i.e., 24:30); and (4) an operation speed of about 5 m/min (manually driven). The sample nonwoven used in the first example was ADL30 Hua Yi ADL30/PPT 30 g/m², and the sample nonwoven used in the first example was ADL50 Hua Yi ADL50/PPT 50 g/m².

Determination of Web Density and Basis Weight—An example on how to determine thickness for bulky nonwoven can be found in WSP120.2.R4 (EDANA). An example on how to determine basis weight for a bulky nonwoven can be found in WSP130.1.R4 (EDANA). The density of each sample was determined as follows: (1) the sample was cut using a whole punch to have a specific sample area [A], using a Hanolex 3295ø50 mm, A 19.63 cm²; (2) the sample thickness [H] was determined using a digital indicator with presser foot, using a Mitutoyo 543-470B, with Käfer Ø35 mm presser foot; (3) the sample mass [M] was determined by weighing on an analytical balance using Radwag AS220/C/2; (4) the sample web density [$\rho$] was calculated in accordance with the formula: $\rho = M/(A*H)$, where $\rho$ is sample density [g/cm3], A is sample area [cm²], M is sample mass [g], and H is sample thickness [cm]. The sample punches were Ø50 mm, with an A of 19.63 cm², where $\rho$ unit g/cm³=g/cc. The web basis weight was determined in accordance with the formula: $MA = M/A*10^6$, where MA is the sample mass area [g/m²], A is the sample area [cm²], and M is the sample mass [g].

Determination of Void Volume—Void volume (VV) or Porosity ($\varphi$) is directly proportional to density ($\rho$); therefore, reducing the bulk density will increase the Void Volume. Web porosity (void volume) may be determined in accordance with the formula: $\varphi = M_2 - M_1$, where $\varphi$ is the sample porosity or void volume [g]; $M_1$ is the sample mass [g], and $M_2$ is the sample mass with filed void volume [g].

In a first example, a first acquisition distribution layer (ADL) having a basis weight (weight per unit area) of 50 g/m², ADL50, was subjected to brushing. Prior to brushing, ADL50 had a bulk density of less than 0.10 g/cm³ but greater than 0.09 g/cm³ (about 0.099 g/cm³), and a void volume of less than 0.10 mL/cm² but greater than 0.09 mL/cm² (about 0.099 mL/cm²), as is evidenced by the "#1 PRE-TREATMENT" data plotted in FIG. 22A. After subjection to the brushing treatment, the bulk density and void volume were again determined. After brushing, ADL50 had a bulk density of about 0.075 g/cm³ and a void volume of about 0.075 mL/cm², as is evidenced by the "#1 POST-TREATMENT" data plotted in FIG. 22A. Thus, subjection to the brushing resulted in an about 24% decrease in the bulk density of ADL50 and an about 45% increase in the void volume of ADL50. In the first example there was a 0.03% loss in process (LIP). That is, 0.03% of the fibers were lost from the NW during bulkification.

In a second example, a second acquisition distribution layer (ADL) having a basis weight (weight per unit area) of 30 g/m², ADL30, was subjected to brushing. Prior to brushing, ADL30 had a bulk density of less than 0.08 g/cm³ but greater than 0.06 g/cm³ (about 0.07 g/cm³), and a void volume of less than 0.08 mL/cm² but greater than 0.06 mL/cm² (about 0.07 mL/cm²), as is evidenced by the "#2 PRE-TREATMENT" data plotted in FIG. 22B. After subjection to the brushing treatment, the bulk density and void volume were again determined. After brushing, ADL30 had a bulk density of less than 0.06 g/cm³ but greater than 0.05 g/cm³, and a void volume of less than 0.06 mL/cm² but greater than 0.05 mL/cm², as is evidenced by the "#2 PRE-TREATMENT" data plotted in FIG. 22B. Thus, subjection to the brushing resulted in an about 27% decrease in the bulk density of ADL30 and an about 37% increase in the void volume of ADL30.

Figure 22C:
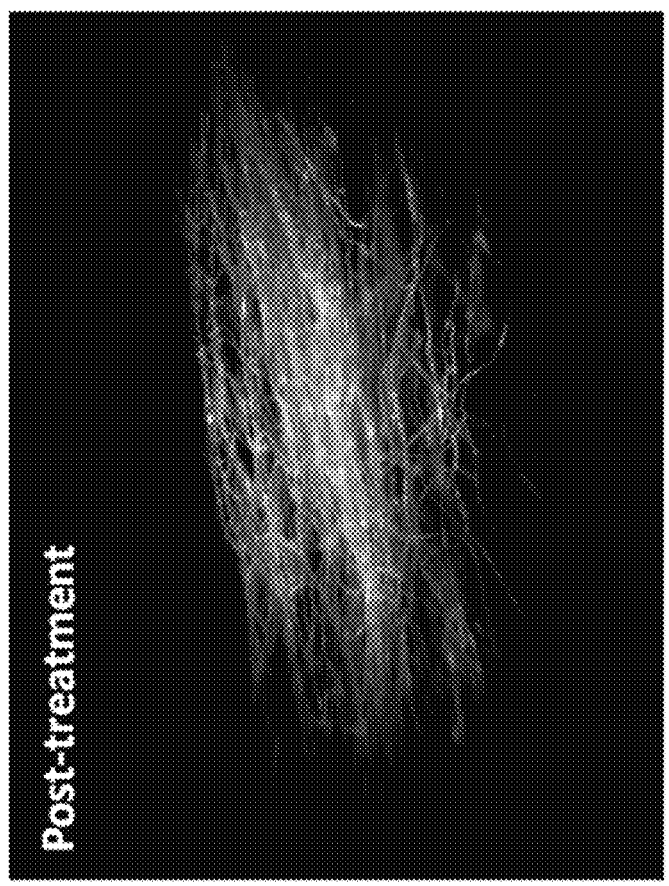
FIGS. 22C and 22D are scanning electron microscopy (SEM) images of fibers before and after bulkification taken during the bulkification examples described herein.
Figure 22D:
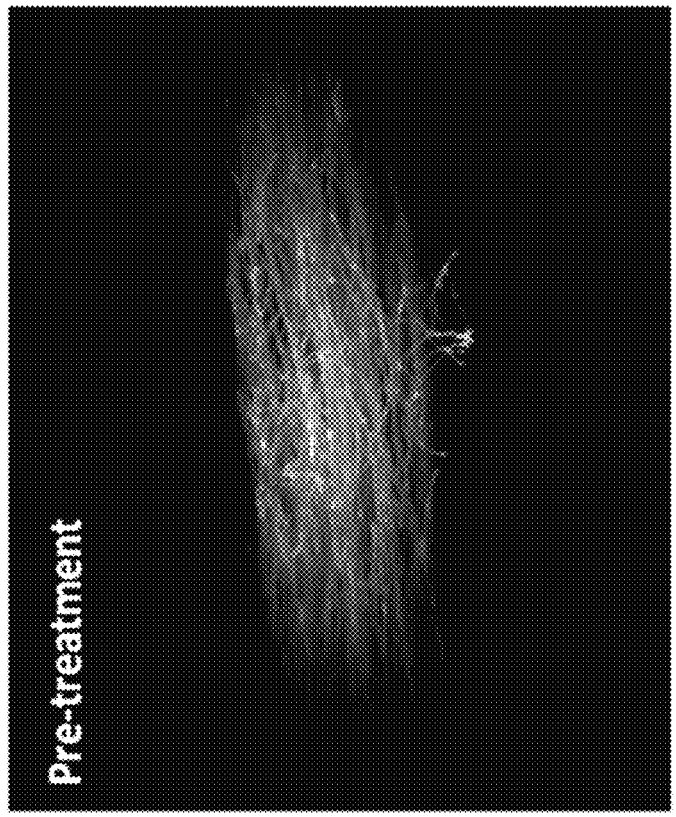

FIGS. 22C and 22D are scanning electron microscope (SEM) images of an ATNW before and after bulkification, respectively. It is evident from FIGS. 22C and 22D that the nonwoven increases in void volume and decreases in bulk density.

The measurements of density and void volume were determined in accordance with the standards set forth by EDANA. The thickness of the nonwoven sheets were measured using a digital micrometer that applies a standard amount of pressure to the material. The basis weights are measured by a cutting sample of the nonwovens to a standard size (100 mm diameter circle) using a sample cutter and then weighing that sample.

Bulkification—Alternative Systems

FIG. 23A depicts an alternative system 2300a for bulkifying nonwovens, with like reference numerals denoting like elements with respect to FIGS. 20 and 23. In system 2300a, nonwoven 2004 is subjected to simultaneous brushing on a top and bottom surface thereof via brushes 2010a and 2010b. Brushes 2010a and 2010b rotate in opposite directions. Brushes 2010a and 2010b may be configured to rotate at the same rate or at different rates.

Figure 23B:
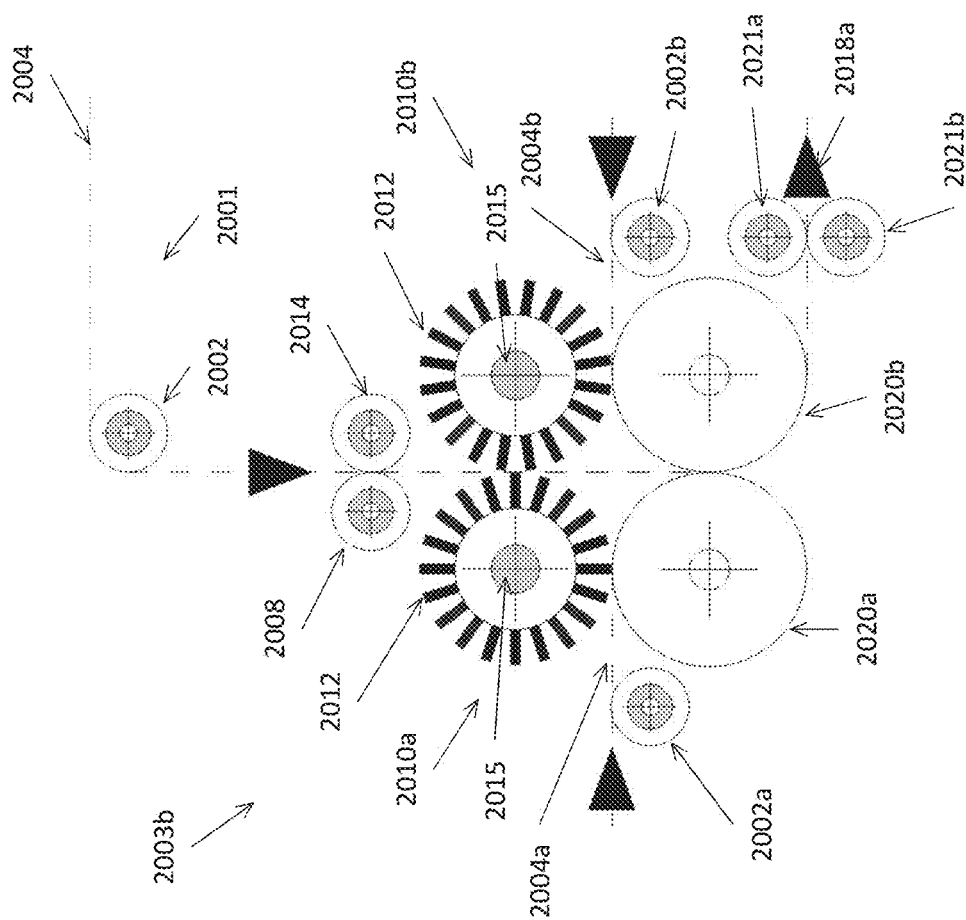

FIG. 23B depicts an alternative system 2300b for bulkifying nonwovens, with like reference numerals denoting like elements with respect to FIGS. 20, 23, and 23A. In system 2300b, a first nonwoven 2004 is subjected to simultaneous brushing on a top and bottom surface thereof via brushes 2010a and 2010b. Brushes 2010a and 2010b may rotate in opposite directions or the same direction. Brushes 2010a and 2010b may be configured to rotate at the same rate or at different rates. A second nonwoven 2004a is fed via roller 2002a to roller 2020a, and is brushed via brush 2010a on only one surface thereof. A third nonwoven 2004b is fed via roller 2002b to roller 2020b, and is brushed via brush 2010b on only one surface thereof. After brushing, nonwoven 2004 is fed to rollers 2020a and 2020b, where it is combined with nonwovens 2004a and 2004b, forming a composite of at least partially bulkified bulky nonwovens, 2018a.

Figure 23C:
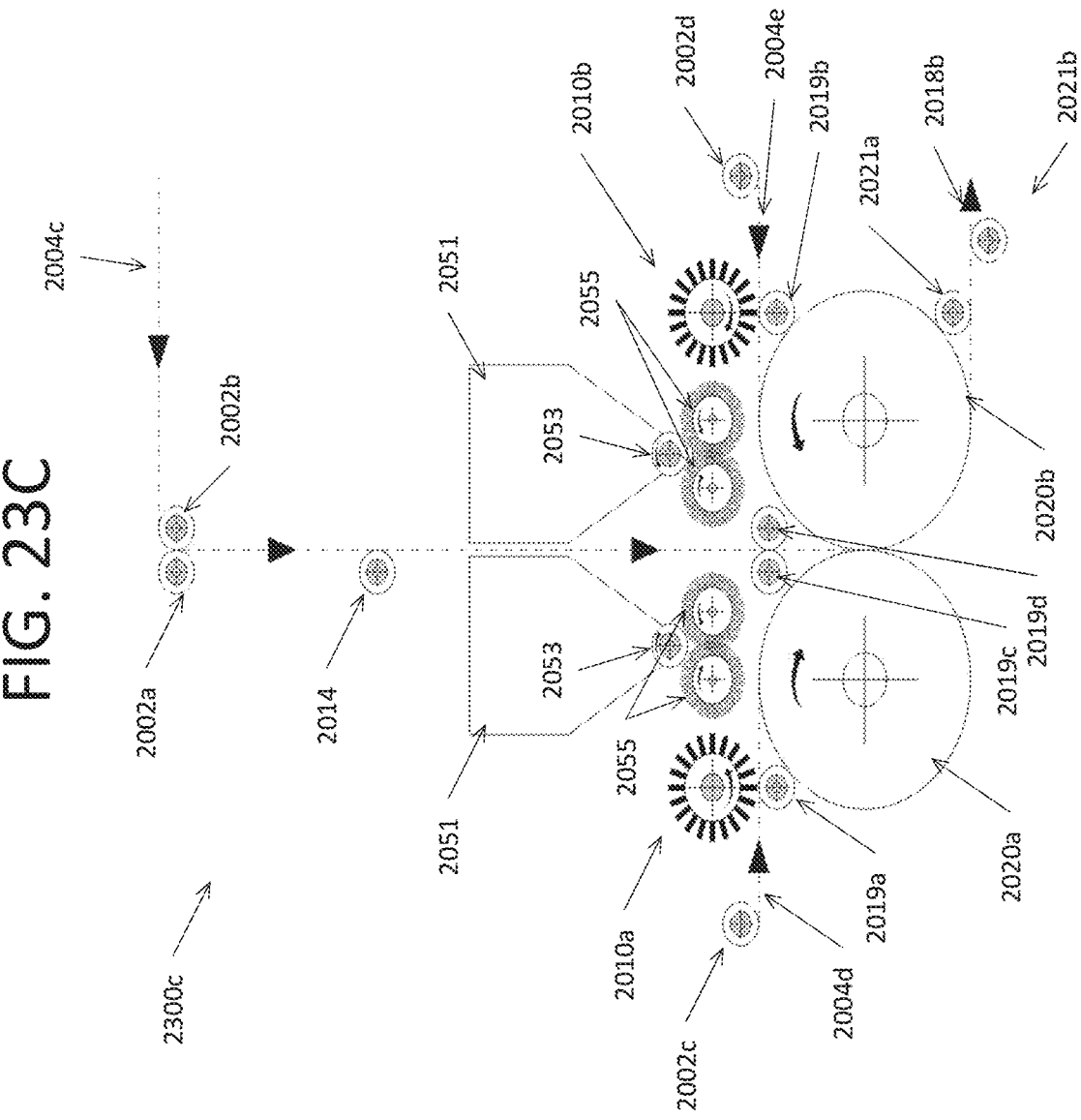

FIG. 23C depicts an alternative system 2300c for bulkifying nonwovens, with like reference numerals denoting like elements with respect to FIGS. 20, 23, 23A, and 23B. In system 2300c, nonwoven 2004c is fed to rollers 2020a and 2020b via rollers 2002a and 2002b and rollers 2019c and 2019d. Nonwoven 2004d is fed to brush 2010a and roller 2019a via roller 2002c. After the surface of nonwoven 2004d is brushed via brush 2010a, the brushed nonwoven 2004d is fed to rollers 2020a and 2020b, where nonwoven 2004d is combined with nonwoven 2004c. Nonwoven 2004e is fed to brush 2010b and roller 2019b via roller 2002d. After the surface of nonwoven 2004e is brushed via brush 2010b, the brushed nonwoven 2004e is fed to rollers 2020a and 2020b, wherein nonwoven 2004e is combined with nonwoven 2004c and nonwoven 2004d. System 2300c includes absorbent material dispensers 2051 (e.g., SAP dispensers), which are positioned to dispense absorbent material onto the bulkified surfaces of both nonwoven 2004d and nonwoven 2004e, prior to combining nonwovens 2004d and 2004e with nonwoven 2004c. Absorbent material dispensers 2051 include dispensing apparatus 2053 and 2055 for dispensing the absorbent material from the hoppers of dispensers 2051 and onto the nonwovens 2004d and 2004e. Rollers 2020a and 2020b may operate to compress nonwovens 2004c, 2004d, and 2004e together, with the absorbent material contained therein, forming bulkified nonwoven composite 2018b.

Figure 23D:
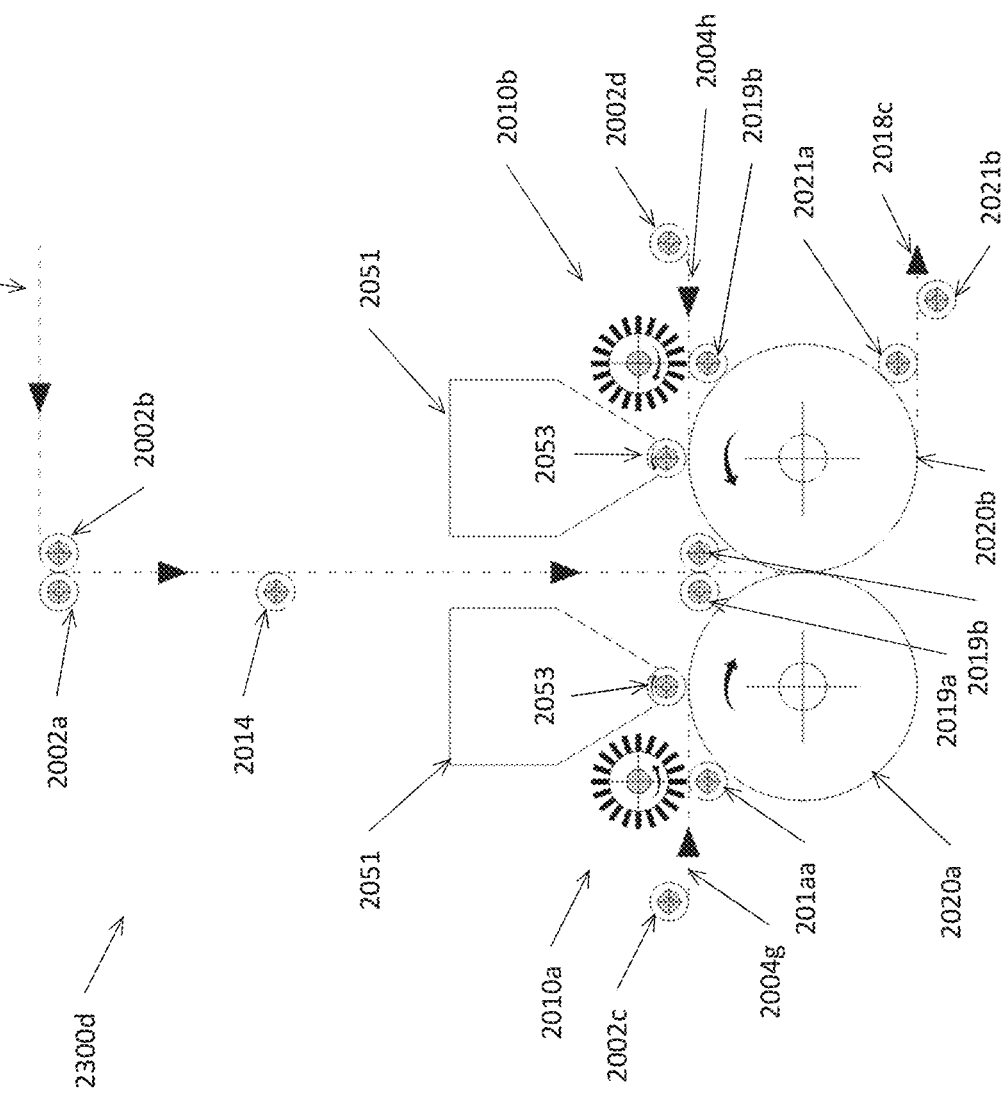

FIG. 23D depicts an alternative system 2300d for bulkifying nonwovens, with like reference numerals denoting like elements with respect to FIGS. 20, 23, 23A, 23B, and 23C. In system 2300d, nonwoven 2004f is fed to rollers 2020a and 2020b via rollers 2002a and 2002b and rollers 2019a and 2019b. Nonwoven 2004g is fed to brush 2010a and roller 2014a via roller 2002c. After the surface of nonwoven 2004g is brushed via brush 2010a, the brushed nonwoven 2004g is fed to rollers 2020a and 2020b, wherein nonwoven 2004g is combined with nonwoven 2004f. Nonwoven 2004h is fed to brush 2010b and roller 2014b via roller 2002d. After the surface of nonwoven 2004h is brushed via brush 2010b, the brushed nonwoven 2004h is fed to rollers 2020a and 2020b, where nonwoven 2004h is combined with nonwoven 2004f and nonwoven 2004g. System 2300d includes absorbent material dispensers 2051, which are positioned to dispense absorbent material onto the bulkified surfaces of both nonwoven 2004g and nonwoven 2004h, prior to combining nonwovens 2004g and 2004h with nonwoven 2004f. Rollers 2020a and 2020b may operate to compress nonwovens 2004f, 2004g, and 2004h together, with the absorbent material contained therein, forming bulkified nonwoven composite 2018c.

FIG. 23E depicts an alternative system 2300e for bulkifying nonwovens, with like reference numerals denoting like elements with respect to FIGS. 20, 23, 23A, 23B, 23C, and 23D. System 2300e is identical to the system 2300d shown in FIG. 23E, with the exception of the addition of brushes 2010c and 2010d positioned to brush and bulkify nonwoven 2004i prior to nonwoven 2004i being fed to rollers 2020a and 2020b for being combined with brushed nonwovens 2004j and 2004k, forming bulkified nonwoven composite 2018d. Thus, nonwoven 2004i is bulkified on both the top and bottom surfaces, with each of nonwovens 2004j and 2004k being bulkified only on one surface thereof.

While the SAP applicators are shown as including hoppers, in some aspects, intermittent 3D vibratory printing tubes, airstreams, or continuous vibratory feeds are used to deposit SAP onto nonwovens. While not shown, thermal treatment may be incorporated into any point in systems 2300a, 2300b, 2300c, 2300d, and 2300e, including upstream and/or downstream of any of the brushes in such systems. In some aspects, any of systems 2000, 2300, 2300a, 2300b, 2300c, 2300d, and 2300e may be incorporated into an existing system for forming absorbent core composites.

Figure 24:
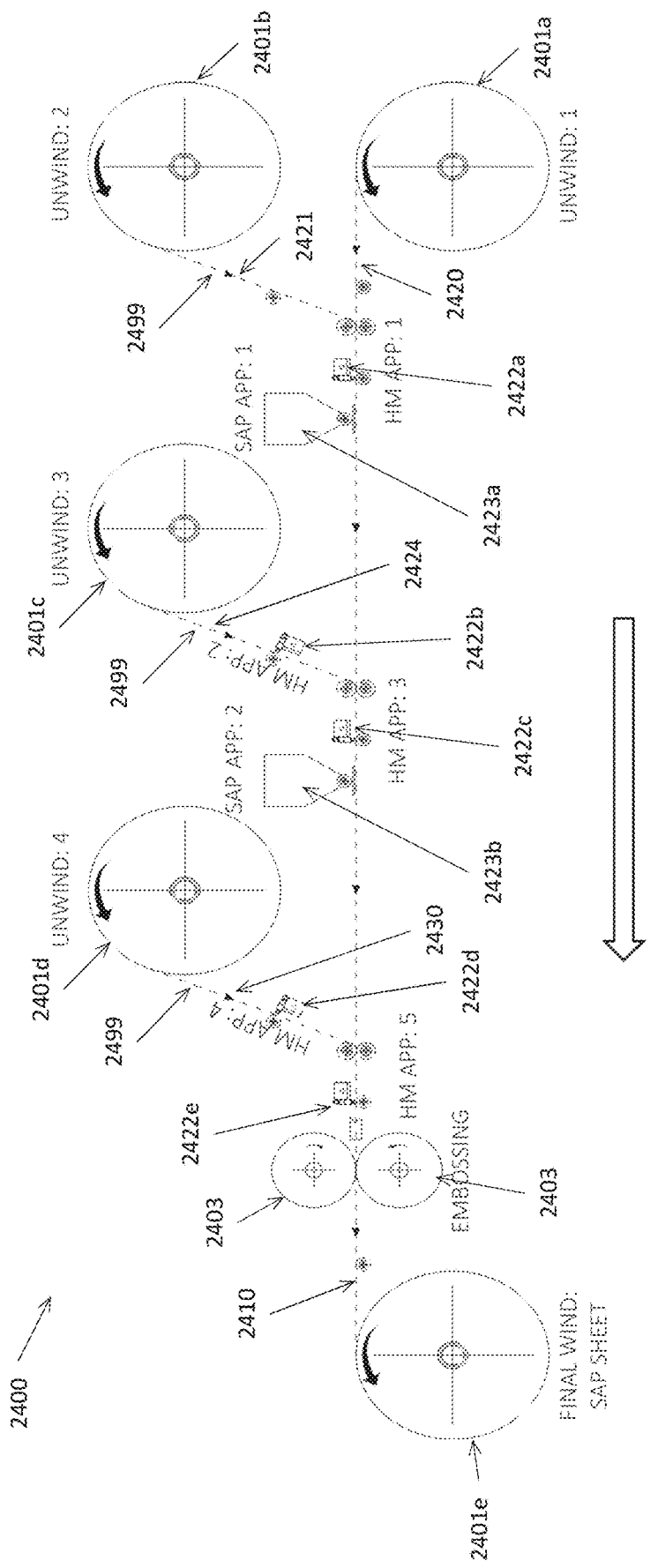
FIG. 24 is a schematic of a system and process for making a multi-layer absorbent core composite or construction, according to the disclosure, indicating where bulkification can be introduced.

Bulkification of nonwovens may be performed at any point in the production of the absorbent core composites disclosed herein, upstream of the location where the SAP is applied to the bulkified nonwoven, such as between the unwinding of the densified (un-bulkified) nonwoven and the SAP application. For example, with reference to FIG. 24, bulkification may occur at the points indicated by "2499". FIG. 24 depicts a system 2400 for forming absorbent core composites 2410. Nonwoven 2420 is unwound from spool or roller 2401a and combined with nonwoven 2421, which is unwound from spool or roller 2401b. Hot melt adhesive is applied at 2422a, and then SAP is applied at 2423a. An additional nonwoven 2499 is unwound from spool or roller 2401c, HMA is applied thereto at 2422b, and it is then applied on top of nonwoven 2424. This is followed by an application of HMA at 2422c, and an application of SAP at 2423b. An additional nonwoven layer 2430 is unwound from spool or roller 2401d, HMA is applied thereto at 2422d, and nonwoven layer 2430 is then combined with nonwoven 2424. HMA is then applied at 2422e, after-which an embossing pattern is applied to the composite layers to form the absorbent core composite 2410, which is collected on spool or roller 2401e.

In any of the bulkification processes described herein, after deposition of the SAP onto the bulkified nonwoven, the SAP is provided with a residence time to allow for the SAP to entangle within the fibers of the BBNW. Entanglement of the SAP within the fibers may be facilitated by: gravity alone (as the SAP is dropped from a height onto the NW web), mechanical means (vibration, vacuum), compression (at the risk of increasing the density of the BBNW), or combinations thereof.

In some aspects, bulkification is performed after the SAP is deposited onto a NW. For example, the SAP may be deposited onto a NW, followed by heating of the NW. In certain aspects, bulkification is performed prior to application of any adhesive to the NW and/or SAP, as adhesive may reduce or prevent the degree of "bulkification". Bulkification performed after SAP deposition may be performed using only heating, as brushing may risk removal of the deposited SAP. For example, SAP may be applied to a NW, followed by thermal bulkification of the NW, then followed by application of adhesive to the NW and/or SAP.

In some aspects, after deposition of SAP onto the BBNW and before or when the BBNW is incorporated into a chassis of an absorbent article, the BBNW is inverted. This may be performed, for example, to avoid having a SAP layer positioned directly beneath the top sheet. Turning over the uppermost BBNW will provide a layer of the BBNW between the topsheet and the first layer of SAP. Such an arrangement provides additional void volume and NW material between the first layer of SAP and the user, providing for faster absorption and a dryer feeling on the user's skin, and providing for increased comfort to the user, as the SAP particles can be hard and uncomfortable when positioned close to the skin.

Material Placement and Arrangement

In any of the embodiments of the absorbent core composites disclosed herein, the positions of the components of the absorbent core composite may be arranged to provide desired fluid handling properties and capabilities, such as fluid flow, fluid absorption, and fluid dispersion properties and capabilities to the absorbent core composite. The absolute and relative positions of the nonwoven layers and absorbent material layers within the absorbent core composite, the sections of within each respective nonwoven layers or absorbent material layer, and the sections within one layer relative to the sections within another layer may be arranged to provide such desired fluid handling properties and capabilities. The position of NW, BNW, BBNW, slitted NW, SAP-containing layers, SAP-containing lanes, and SAP-free lanes may selectively arranged within the absorbent core composite.

Material Placement and Arrangement—SAP Fluid Handling

For example, SAP containing layers or lanes may be positioned in the expected path or area of insult. For handling fluid flow in the z-direction (thickness of the absorbent core composite), the SAP within an absorbent material layer and/or from one absorbent material layer to another may vary such that the permeability of SAP within the absorbent core composite is the highest at the top, body side of the absorbent core composite, and reduces to the lowest level of permeability at the bottom, opposite the body side of the absorbent core composite. For example, with reference to FIG. 17, the SAP contained within absorbent material layer 1702a may have a permeability that is higher than the SAP contained within absorbent material layer 1702b. Also, within a single absorbent material layer, there may be a gradient of SAP having different properties, such that the SAP contained at the top, body side surface of the absorbent material layer (e.g., 1702a) has a permeability that is higher than the SAP contained within at the opposite side of the absorbent material layer (e.g., the bottom or back side of layer 1702a).

Similarly, for handling fluid flow in the z-direction, the SAP within an absorbent material layer and/or from one absorbent material layer to another may vary such that the absorption rate of SAP within the absorbent core composite is the lowest (slowest) at the top, body side of the absorbent core composite, and increases to the highest level of absorption rate (fastest) at the bottom, opposite the body side of the absorbent core composite. Also, the SAP within an absorbent material layer and/or from one absorbent material layer to another may vary such that the absorption capacity of SAP within the absorbent core composite is the lowest at the top, body side of the absorbent core composite, and increases to the highest level of absorption capacity at the bottom, opposite the body side of the absorbent core composite, providing for maximum absorbent efficiency.

Material Placement and Arrangement—Nonwoven Fluid Handling

For handling fluid flow in the z-direction of the absorbent core composites, the nonwoven layers of the absorbent core composites disclosed herein may be arranged such that the NW layers that are positioned in the path of insult have a higher void volume at or near the body side of the absorbent core composite, in comparison to the void volumes of the NW layers that are positioned opposite the body side. For example, with reference to FIG. 17, the nonwoven layer 1704a and/or 1704b may have higher void volume than the nonwoven layer 1704c. Higher void volumes in the nonwoven layers at the body side provide for fluid handling of the initial gush of fluid insult and fluid distribution the fluid within the nonwoven layer. The relative void volumes may be provided by selective arrangement of NW and BNW, and/or by selective bulkification of NW and/or BNW layers.

Material Placement and Arrangement—Profiling Capillarity of Nonwovens

Capillarity is a measure of the ability of a material to flow fluid through fine pores and channels (capillaries) in that material. Capillarity allows for fluid to flow in the x- and y-directions, sometimes referred to as wicking.

In certain aspects, the capillarity of the fiber network of the nonwoven layers may be profiled in the x-y plane thereof. Such profiling may provide a higher capillarity (relative to the fluid target area of insult) at the margins of the absorbent core composite. Such a profiled capillarity provides for fluid to continually flow (spread) towards the margin ends of the absorbent core composite for full utilization thereof. In some aspects, profiling of the capillarity may be accomplished by selective densification and/or bulkification and/or wettability enhancement of the nonwovens, such as via plasma treatment and/or corona treatment of the nonwovens. In certain aspects, higher capillarity nonwoven layers are arranged and/or positioned towards the bottom (opposite the body side) of the absorbent core composites, such as to support wicking flow of fluid into the SAP in the lower absorbent material layer and to enhance fluid spreading within the core relative to the fluid spreading that would occur in response only to gravity; thereby, providing for full core utilization during use of the absorbent core composite.

One example of a nonwoven having profiled capillarity is shown in FIG. 16C, wherein the bulkified sections 1665 have increased capillarity relative to the non-bulkified sections 1670. The non-bulkified sections 1670, however, have higher bulk density relative to the bulkified sections 1665, such that that non-bulkified sections 1670 can more readily prevent SAP particles from filtering through the nonwoven than can the bulkified sections 1665.

In use, SAP absorption is osmotic pressure driven, and slower than the more free flow of fluid in fibrous networks, which is capillarity or fluid momentum driven. A higher basis weight (or void volume) nonwoven will allow more fluid to flow and spread within the core composite.

Exemplary Absorbent Core Composite

With reference to FIG. 25, an exemplary absorbent core composite in accordance with the present disclosure is shown. Absorbent core composite, MLC 2500, has bodyside 2502 and backside 2054 opposite bodyside 2502. MLC 2500 includes three nonwoven layers, including nonwoven layer 2510, nonwoven layer 2512, nonwoven layer 2514, and nonwoven layer 2516; and one absorbent material layer 2520.

Nonwoven layer 2510 may be a spunbond nonwoven layer, a tissue, or an aperture nonwoven. In some embodiments, nonwoven layer 2510 is not and/or does not include SMS. Nonwoven layer 2510 may facilitate retention of SAP particles within MLC 2500. In certain embodiments, MLC 2500 does not include the uppermost nonwoven layer 2510.

Positioned below nonwoven layer 2510 is nonwoven layer 2512. Nonwoven layer 2512 may be or include a relatively high-density fiber layer of bicomponent fibers. In embodiments that do not include nonwoven layer 2510, nonwoven layer 2512 may form the uppermost layer of MLC 2500. In some embodiments, there is no layer (nonwoven or absorbent material) that is positioned between nonwoven layer 2510 and nonwoven layer 2512. Nonwoven layer 2510 may be adhered with nonwoven layer 2512. In some embodiments, nonwoven layer 2512 is a non-bulkified nonwoven or a densified air-through nonwoven.

Positioned below nonwoven layer 2512 is nonwoven layer 2514. Nonwoven layer 2514 may be or include a relatively low-density fiber layer of bicomponent fibers. That is, the bulk density of nonwoven layer 2514 may be lower than the bulk density of nonwoven layer 2412. The differential in density between nonwoven layers 2512 and 2514 may be the result of bulkification of nonwoven layer 2514, densification of nonwoven layer 2512, selection of nonwoven layers having different densities, or combinations thereof. In some embodiments, there is no layer (nonwoven or absorbent material) that is positioned between nonwoven layer 2512 and nonwoven layer 2514. Nonwoven layer 2512 may be adhered with nonwoven layer 2514. In some embodiments, nonwoven layers 2512 and 2514 are a single, unitary fiber layer. In some such embodiments, nonwoven layer 2512 is a selectively densified region of the single, unitary fiber layer. In some such embodiments, nonwoven layer 2514 is a selectively bulkified region of the single, unitary fiber layer.

Positioned below nonwoven layer 2514 is nonwoven layer 2516. Nonwoven layer 2516 may be or include an airlaid nonwoven, a tissue layer, an SMS nonwoven, a spunbond nonwoven, or an airthrough nonwoven. In certain embodiments, nonwoven layer 2516 is a relatively absorbent nonwoven, such as an airlaid. In some embodiments, there is no layer (nonwoven or absorbent material) that is positioned between nonwoven layer 2514 and nonwoven layer 2516. Nonwoven layer 2514 may be adhered with nonwoven layer 2516.

Absorbent material layer 2520 includes or consists of SAP particles. The SAP particles of absorbent material layer 2520 are embedded within nonwoven layer 2514. In some embodiments, absorbent material layer 2520 is adhered to fibers of nonwoven layer 2514. In other embodiments, absorbent material layer 2520 is adhesive free, and absorbent material layer 2520 particles are entangled within the fibers of nonwoven layer 2514. The particles of absorbent material layer 2520 are spaced apart within nonwoven layer 2514 and intermixed with the fibers thereof. As shown, MLC 2500 includes a SAP-free lane 2550 centered between the lateral edges of MLC 2500 and extending longitudinally along MLC 2500.

MLC 2500 may be made in the orientation as shown in FIG. 25, by: laying nonwoven layer 2516, laminating nonwoven 2514 onto nonwoven 2516, depositing SAP within nonwoven layer 2514, laminating nonwoven 2512 onto nonwoven 2514, and laminating nonwoven 2510 onto nonwoven 2512. In other embodiments, this sequence is reversed, such that the process includes: laying nonwoven 2510, laminating nonwoven 2512 to nonwoven 2510, laminating nonwoven 2514 to nonwoven 2512, depositing SAP within nonwoven 2514, and laminating nonwoven 2516 to nonwoven 2514.

In some embodiments, the bulky nonwovens of MLC 2500, nonwovens 2512 and 2514, are formed in-situ, such as on top of the airlaid nonwoven, nonwoven 2516 or on top of nonwoven 2510, depending on the order of production. For example, bicomponent fibers may be deposited onto airlaid nonwoven 2516 (or nonwoven 2510) to form a web of fibers. A higher density region of the bicomponent fibers will be formed at the bottom of the deposited web as a result of the fibers settling during the formation of the web, with a lower density population of the bicomponent fiber at a top of the deposited web. This density gradient of bicomponent fibers in the deposited web will form the relatively high-density bodyside bicomponent fiber layer (layer 2512) and the relatively low-density garment side bicomponent fiber layer (layer 2514). In some embodiments, the relatively high-density bodyside bicomponent fiber layer (layer 2512) is positioned adjacent the airlaid nonwoven 2516. In other embodiments, the relatively low-density bodyside bicomponent fiber layer (layer 2514) is positioned adjacent the airlaid nonwoven 2516.

Combinations of Differing Layers

Each of the various embodiments of the layers and arrangements thereof disclosed herein may be combined in various combinations to provide various absorbent core composites in accordance with the present disclosure. The absorbent core composites disclosed herein may include: one or more nonwoven layers have various thickness, widths, lengths, SAP contents, and SAP dispersion amongst various layers (e.g., as shown and described with reference to FIGS. 4 and 4A-4M); one or more absorbent material layers, with or without SAP-free lanes (e.g., as shown and described with reference to FIG. 6A to 9); one or more nonwoven layers having silts (e.g., as shown and described with reference to FIG. 10); one or more loose fiber layers (e.g., as shown and described with reference to FIGS. 13A-13C); one or more nonwoven layers either fully or sectionally bulkified (e.g., as shown and described with reference to FIG. 15A-19B); one ore more in-situ formed bulky nonwoven layers (e.g., as shown and described with reference to FIG. 25); or any combination thereof. Any such absorbent core composites may be incarnated into an absorbent article, such as those shown and describe with reference to FIGS. 1A to 1F.

Some embodiments relate to system and/or processes for forming any of the absorbent core composites or articles disclosed herein. Such systems and/or processes may incorporate: one or more of the features of the system shown in FIG. 5; one or more of the features of the system shown in FIG. 11; one or more of the features of the system shown in FIG. 12; one or more of the features of the system shown in FIG. 14; one or more of the features of the system shown in FIG. 20; one or more of the features of any of the apparatus shown in FIGS. 20A-20C; one or more of the features of the system shown in FIG. 21; one or more of the features of the system shown in FIG. 23; one or more of the features of any or all of the systems shown in FIGS. 23A-23E; one or more of the features of the system shown in FIG. 24; or any combination thereof.

An important benefit of the resultant structure of many of the absorbent core composites described herein is a composite with increased loftiness (i.e., which promotes comfort and softer regions) and void space out of an otherwise flat core and without significant void volume. The added void volume serves to provide a temporary fluid holding and fluid transporting space. This space provides the fluid a place within the confines of the core to temporarily reside during the few seconds it takes for the superabsorbent to activate and permanently lock up the fluid. The voids or spaces also act to channel fluid, and facilitate dispersal of fluid exudates.

The foregoing descriptions have been presented for purposes of illustration and description. These descriptions are not intended to limit the disclosure or aspects of the disclosure to the specific absorbent core composites and constructions or articles, apparatus and processes disclosed. Various aspects of the disclosure are intended for applications other than diapers and training pants. The absorbent core constructions described may also be incorporated into or with other garments, textiles, fabrics, and the like, or combinations thereof. The absorbent core constructions described may also incorporate different components. Further, the absorbent core composites described may refer to substrates (e.g., composite sheets) of such core composites prior to individualizing and incorporating such absorbent core composites (as discrete absorbent core composites) into disposable absorbent articles. These and other variations of the disclosure will become apparent to one generally skilled in the relevant consumer product art provided with the present disclosure. Consequently, variations and modifications commensurate with the above teachings, and the skill and knowledge of the relevant art, are within the scope of the present disclosure. The embodiments described and illustrated herein are further intended to explain the best modes for practicing the disclosure, and to enable others skilled in the art to utilize the disclosure and other embodiments and with various modifications required by the particular applications or uses of the present disclosure.

The invention claimed is:

1. A method of making an absorbent article, the method comprising:
    mechanically manipulating a first nonwoven such that a bulk density of the first nonwoven is decreased and a void volume of the first nonwoven is increased, wherein mechanically manipulating the first nonwoven comprises mechanically manipulating a first surface of the first nonwoven and mechanically manipulating a second surface of the first nonwoven;
    combining a second nonwoven with the first nonwoven;
    prior to combining the second nonwoven with the first nonwoven, depositing absorbent material onto one of the first and second nonwovens; and
    collecting the absorbent article, the absorbent article comprising the first nonwoven, the second nonwoven and the absorbent material
    wherein mechanically manipulating the first and second surfaces of the first nonwoven comprises brushing the first and second surfaces of the first nonwoven.

2. The method of claim 1, wherein the first surface is brushed with a first rotary brush and the second surface is brushed with a second rotary brush.

3. The method of claim 2, wherein the first and second rotary brushes rotate in opposite directions.

4. The method of claim 2, wherein the first and second rotary brushes rotate at different rates.

5. The method of claim 1, wherein the absorbent material is deposited onto the first surface of the first nonwoven.

6. The method of claim 5, wherein the absorbent material is deposited onto the first nonwoven after the mechanical manipulation of the first nonwoven.

7. The method of claim 1, wherein combining the first and second nonwovens comprises embossing the first nonwoven to the second nonwoven, wherein the embossing increases the bulk density of the first nonwoven and decreases the void volume of the first nonwoven at locations where the first nonwoven is embossed.

8. The method of claim 1, further comprising providing the first nonwoven with a gradient pore structure by:
    densifying a first section of the first nonwoven to increase the bulk density of the first nonwoven and decrease the void volume of the first nonwoven in the first section; and
    bulkyfing a second section of the first nonwoven by mechanically manipulating the second section to decrease the bulk density of the first nonwoven and increase the void volume of the first nonwoven in the second section.

9. The method of claim 1, wherein the mechanical manipulation of the first surface of the first nonwoven increases the void volume of the first surface of the first nonwoven by from 5% to 75% and decreases the bulk density of the first surface of the first nonwoven by from 5% to 50%.

10. The method of claim 1, wherein mechanically manipulating the first surface of the first nonwoven forms at least one bulkified lane on the first nonwoven, and wherein at least one non-bulkified lane on the first nonwoven is positioned adjacent the at least one bulkified lane.

11. The method of claim 10, wherein the absorbent material is deposited in the at least one bulkified lane.

12. The method of claim 10, wherein the first nonwoven has a plurality of the bulkified lanes and a plurality of the non-bulkified lanes, wherein depositing the absorbent material comprises depositing SAP in SAP-containing lanes on the first nonwoven that are coincident with the bulkified lanes, and wherein SAP-free lanes on the first nonwoven are coincident with the non-bulkified lanes.

13. The method of claim 1, wherein mechanically manipulating the first surface of the first nonwoven increases a thickness of the first nonwoven between the first surface and the second surface of the first nonwoven.

14. The method of claim 1, wherein mechanically manipulating the first surface of the first nonwoven increases a distance between fibers of the first nonwoven.

15. A method of making an absorbent article, the method comprising:
    mechanically manipulating a first nonwoven such that a bulk density of the first nonwoven is decreased and a void volume of the first nonwoven is increased, wherein mechanically manipulating the first nonwoven comprises brushing a first surface of the first nonwoven;
    combining a second nonwoven with the first nonwoven;
    prior to combining the second nonwoven with the first nonwoven, depositing absorbent material onto one of the first and second nonwovens;
    collecting the absorbent article, the absorbent article comprising the first nonwoven, the second nonwoven and the absorbent material;
    heating the first nonwoven during the brushing, prior to the brushing, or combinations thereof; and
    cooling the first nonwoven after the brushing, wherein the cooling initiates bonding between at least some fibers of the first nonwoven.

16. The method of claim 15, wherein the heating comprises imparting a stream of heated air onto the first nonwoven.

17. The method of claim 15, wherein the first nonwoven is heated prior to the brushing.

18. A method of making an absorbent article, the method comprising:
- mechanically manipulating a first nonwoven such that a bulk density of the first nonwoven is decreased and a void volume of the first nonwoven is increased;
- combining a second nonwoven with the first nonwoven;
- prior to combining the second nonwoven with the first nonwoven, depositing absorbent material onto one of the first and second nonwovens; and
- collecting the absorbent article, the absorbent article comprising the first nonwoven, the second nonwoven and the absorbent material;
- wherein mechanically manipulating the first surface of the first nonwoven forms at least one bulkified lane on the first nonwoven, wherein at least one non-bulkified lane on the first nonwoven is positioned adjacent the at least one bulkified lane, and wherein the absorbent material is deposited in the at least one non-bulkified lane.

19. The method of claim 18, wherein the first nonwoven has a plurality of the bulkified lanes and a plurality of the non-bulkified lanes, wherein depositing the absorbent material comprises depositing SAP in SAP-containing lanes on the first nonwoven that are coincident with the non-bulkified lanes, and wherein SAP-free lanes on the first nonwoven are coincident with the bulkified lanes.

20. A method of making an absorbent article, the method comprising:
- mechanically manipulating a first nonwoven such that a bulk density of the first nonwoven is decreased and a void volume of the first nonwoven is increased, wherein mechanically manipulating the first nonwoven comprises brushing a first surface of the first nonwoven;
- combining a second nonwoven with the first nonwoven;
- prior to combining the second nonwoven with the first nonwoven, depositing absorbent material onto one of the first and second nonwovens;
- collecting the absorbent article, the absorbent article comprising the first nonwoven, the second nonwoven and the absorbent material;
- wherein the first nonwoven is heated during the brushing.

21. A method of making an absorbent article, the method comprising:
- mechanically manipulating a first nonwoven such that a bulk density of the first nonwoven is decreased and a void volume of the first nonwoven is increased, wherein mechanically manipulating the first nonwoven comprises brushing a first surface of the first nonwoven;
- combining a second nonwoven with the first nonwoven;
- prior to combining the second nonwoven with the first nonwoven, depositing absorbent material onto one of the first and second nonwovens;
- collecting the absorbent article, the absorbent article comprising the first nonwoven, the second nonwoven and the absorbent material;
- heating the first nonwoven during the brushing, prior to the brushing, or combinations thereof;
- wherein the heating comprises imparting IR onto the first nonwoven.

22. A method of making an absorbent article, the method comprising:
- mechanically manipulating a first nonwoven such that a bulk density of the first nonwoven is decreased and a void volume of the first nonwoven is increased;
- combining a second nonwoven with the first nonwoven;
- prior to combining the second nonwoven with the first nonwoven, depositing absorbent material onto the second nonwoven; and
- collecting the absorbent article, the absorbent article comprising the first nonwoven, the second nonwoven and the absorbent material.

23. A method of making an absorbent article, the method comprising:
- mechanically manipulating a surface of a first nonwoven such that a bulk density of the first nonwoven is decreased and a void volume of the first nonwoven is increased;
- mechanically manipulating a surface of a second nonwoven such that a bulk density of the second nonwoven is decreased and a void volume of the second nonwoven is increased;
- depositing absorbent material onto at least one of the first and second nonwovens;
- combining the first nonwoven with the second nonwoven; and
- collecting the absorbent article, the absorbent article comprising the first nonwoven, the second nonwoven and the absorbent material.

24. The method of claim 23, wherein combining the first nonwoven with the second nonwoven comprises engaging the mechanically manipulated surface of the first nonwoven with the mechanically manipulated surface of the second nonwoven.

25. The method of claim 23, wherein mechanically manipulating the surfaces of the first and second nonwovens comprises brushing the surfaces of the first and second nonwovens.

26. The method of claim 25, wherein the brushing is performed with brushes having bristles.

27. The method of claim 26, wherein the brushes are rotary brushes.

28. The method of claim 27, further comprising varying a rate at which bristles of the rotary brushes rotate relative to the surfaces of the first and second nonwovens.

29. The method of claim 27, wherein the rotary brushes each comprise a brush axle with a plurality of the bristles extending therefrom, wherein a first section of each brush axle has bristles extending to a first height from the brush axle, wherein a second section of each brush axle has bristles extending to a second height from the brush axle, and wherein the first height is greater than the second height.

30. The method of claim 27, wherein the bristles of each brush vary in thickness.

31. The method of claim 27, further comprising intermittently engaging the rotary brushes with the surfaces of the first and second nonwovens to intermittently mechanically manipulate the first and second nonwovens.

32. The method of claim 27, wherein the bristles of each brush vary in packing density.

33. The method of claim 27, further comprising varying a pressure at which the bristles of the rotary brushes engage the first and second nonwovens.

* * * * *